(12) United States Patent
Ariav et al.

(10) Patent No.: US 11,627,749 B2
(45) Date of Patent: Apr. 18, 2023

(54) COMPOSITION AND/OR COMBINATION FOR AQUACULTURE

(71) Applicant: OmniGen Research, LLC, Corvallis, OR (US)

(72) Inventors: Ra'anan Ariav, Airport (IL); Neil E. Forsberg, Corvallis, OR (US); Steven B. Puntenney, Ione, OR (US)

(73) Assignee: Omnigen Research, LLC, Corvallis, OR (US)

( * ) Notice: Subject to any disclaimer, the term of this patent is extended or adjusted under 35 U.S.C. 154(b) by 0 days.

(21) Appl. No.: 17/150,254

(22) Filed: Jan. 15, 2021

(65) Prior Publication Data

US 2021/0368827 A1 Dec. 2, 2021

Related U.S. Application Data

(63) Continuation of application No. 15/914,543, filed on Mar. 7, 2018, now abandoned, which is a continuation-in-part of application No. PCT/US2016/051080, filed on Sep. 9, 2016.

(60) Provisional application No. 62/216,162, filed on Sep. 9, 2015, provisional application No. 62/216,153, filed on Sep. 9, 2015.

(51) Int. Cl.
| | | |
|---|---|---|
| *A23K 50/80* | (2016.01) | |
| *A23K 10/30* | (2016.01) | |
| *A23K 20/163* | (2016.01) | |
| *A23K 20/28* | (2016.01) | |
| *A23K 10/18* | (2016.01) | |
| *A23K 20/158* | (2016.01) | |
| *A23K 40/30* | (2016.01) | |
| *A23K 40/25* | (2016.01) | |
| *A61K 36/73* | (2006.01) | |
| *A61K 36/896* | (2006.01) | |
| *A61K 9/00* | (2006.01) | |
| *A61K 9/14* | (2006.01) | |
| *A61K 31/716* | (2006.01) | |
| *A61K 33/00* | (2006.01) | |
| *A61K 33/06* | (2006.01) | |
| *A61K 35/74* | (2015.01) | |
| *A61K 36/185* | (2006.01) | |
| *A61K 36/88* | (2006.01) | |
| *A61K 38/47* | (2006.01) | |
| *A23K 20/195* | (2016.01) | |
| *A23K 20/111* | (2016.01) | |
| *A23K 20/121* | (2016.01) | |

(52) U.S. Cl.
CPC .............. *A23K 50/80* (2016.05); *A23K 10/18* (2016.05); *A23K 10/30* (2016.05); *A23K 20/158* (2016.05); *A23K 20/163* (2016.05); *A23K 20/28* (2016.05); *A23K 40/25* (2016.05); *A23K 40/30* (2016.05); *A61K 9/0056* (2013.01); *A61K 9/148* (2013.01); *A61K 31/716* (2013.01); *A61K 33/00* (2013.01); *A61K 33/06* (2013.01); *A61K 35/74* (2013.01); *A61K 36/185* (2013.01); *A61K 36/73* (2013.01); *A61K 36/88* (2013.01); *A61K 36/896* (2013.01); *A61K 38/47* (2013.01); *C12Y 302/01006* (2013.01); *A23K 20/111* (2016.05); *A23K 20/121* (2016.05); *A23K 20/195* (2016.05); *Y02A 40/818* (2018.01)

(58) Field of Classification Search
CPC ........ A23K 50/80; A23K 10/18; A23K 10/30; A23K 20/158; A23K 20/163; A23K 20/28; A23K 40/25; A23K 40/30; A23K 20/111; A23K 20/121; A23K 20/195; A61K 9/0056; A61K 9/148; A61K 31/716; A61K 33/00; A61K 33/06; A61K 35/74; A61K 36/185; A61K 36/73; A61K 36/88; A61K 36/896; A61K 38/47; C12Y 302/01006; Y02A 40/818
See application file for complete search history.

(56) References Cited

U.S. PATENT DOCUMENTS

| | | | |
|---|---|---|---|
| 3,468,667 | A | 9/1969 | Chandler et al. |
| 3,692,529 | A | 9/1972 | Rychman |

(Continued)

FOREIGN PATENT DOCUMENTS

| | | |
|---|---|---|
| CN | 102178078 | 9/2011 |
| CN | 103892130 | 7/2014 |

(Continued)

OTHER PUBLICATIONS

William H. Karasov, et al, Ecological Physiology of Diet and Digestive Systems, 73 Annu. Rev. Physiol. 69 (Year: 2011).*
"2008-2009 Report on Advances in Fishery Science," China Association for Science and Technology, *Science and Technology of China Press*, p. 142, Apr. 2009.

(Continued)

*Primary Examiner* — Sean M Basquill
(74) *Attorney, Agent, or Firm* — Klarquist Sparkman, LLP

(57) ABSTRACT

Disclosed embodiments concern a composition and/or combination, and a method of administering the same as a feed, or to supplement the feed of, aquatic animals, particularly for aquaculture. Disclosed composition and/or combination embodiments may comprise glucan, silica, mineral clay, mannans, *yucca, quillaja*, a probiotic, and/or an adhesive agent. The adhesive agent may be selected particularly to facilitate administration to aquatic species. In certain embodiments the adhesive agent comprises an oil, such as soy oil, or a syrup, such as molasses, or combinations thereof. In some embodiments the composition and/or combination may further comprise polyphenol, an antimicrobial, and/or a vaccine. Also disclosed is a method for promoting growth and/or immune function in aquatic animals.

24 Claims, 60 Drawing Sheets

(56) References Cited

U.S. PATENT DOCUMENTS

| | | | |
|---|---|---|---|
| 3,939,275 A | 2/1976 | Baile et al. | |
| 3,943,250 A | 3/1976 | Richter et al. | |
| 4,138,479 A | 2/1979 | Truscheit et al. | |
| 4,729,902 A | 3/1988 | Urman et al. | |
| 4,759,932 A | 7/1988 | Laurent et al. | |
| 4,765,992 A | 8/1988 | Geneix et al. | |
| 4,857,512 A | 8/1989 | Wagner et al. | |
| 4,950,488 A | 8/1990 | Schweitzer et al. | |
| 5,032,401 A | 7/1991 | Jamas et al. | |
| 5,140,949 A * | 8/1992 | Chu | B01J 20/18 426/2 |
| 5,192,547 A | 3/1993 | Taylor | |
| 5,519,009 A | 5/1996 | Donzis | |
| 5,698,599 A | 12/1997 | Subbiah | |
| 5,871,966 A * | 2/1999 | Kofod | C11D 3/38645 435/74 |
| 5,876,990 A | 3/1999 | Reddy et al. | |
| 6,054,146 A | 4/2000 | Ballard et al. | |
| 6,306,453 B1 | 10/2001 | Kuerzinger | |
| 6,344,221 B1 | 2/2002 | Evans | |
| 6,444,448 B1 * | 9/2002 | Wheatcroft | A23L 29/271 424/234.1 |
| 8,142,798 B2 | 3/2012 | Forsberg et al. | |
| 8,236,303 B2 | 8/2012 | Forsberg et al. | |
| 8,431,133 B2 | 4/2013 | Forsberg et al. | |
| 8,568,715 B2 | 10/2013 | Puntenney et al. | |
| 8,663,644 B2 | 3/2014 | Forsberg et al. | |
| 8,828,402 B2 | 9/2014 | Forsberg et al. | |
| 8,834,868 B2 | 9/2014 | Forsberg et al. | |
| 9,173,926 B2 * | 11/2015 | Forsberg | A23K 20/189 |
| 2003/0235565 A1 | 12/2003 | Cheung | |
| 2004/0131730 A1 | 7/2004 | Dalzeil et al. | |
| 2005/0220846 A1 | 10/2005 | Puntenney et al. | |
| 2006/0115881 A1 | 6/2006 | Damude et al. | |
| 2006/0239992 A1 * | 10/2006 | Puntenney | A61K 35/02 424/94.61 |
| 2007/0253983 A1 | 11/2007 | Forsberg et al. | |
| 2011/0027387 A1 | 2/2011 | Olsen | |
| 2011/0195146 A1 | 8/2011 | Russi | |
| 2011/0293736 A1 | 12/2011 | Cannock | |
| 2013/0196021 A1 | 8/2013 | Miller et al. | |
| 2015/0209416 A1 | 7/2015 | Puntenney et al. | |
| 2017/0202244 A1 | 7/2017 | Calabotta et al. | |

FOREIGN PATENT DOCUMENTS

| | | | |
|---|---|---|---|
| DE | 19952360 | | 5/2001 |
| DE | 19952360 A1 * | 5/2001 | A23K 20/168 |
| EP | 0664961 * | 8/1995 | A23N 17/005 |
| EP | 0664961 A1 | 8/1995 | |
| EP | 2674397 A1 | 12/2013 | |
| GB | 1 567 846 | 5/1980 | |
| JP | 58-146243 A | 8/1983 | |
| JP | 7-107923 | 4/1995 | |
| JP | 07184595 A | 7/1995 | |
| JP | 8-131089 | 5/1996 | |
| JP | 2003-289814 * | 10/2003 | A23K 1/16 |
| WO | WO 95/30022 A1 | 11/1995 | |
| WO | WO 97/02356 A1 | 1/1997 | |
| WO | WO 2007/021262 | 2/2007 | |
| WO | WO 2013/037963 | 3/2013 | |
| WO | WO 2015/061755 | 4/2015 | |
| WO | WO 2015/107218 | 7/2015 | |
| WO | WO 2015/123456 | 8/2015 | |
| WO | WO 2015/179840 | 11/2015 | |
| WO | WO 2016/054338 | 4/2016 | |
| WO | WO 2016/070091 | 5/2016 | |

OTHER PUBLICATIONS

AOAC. Official Methods of Analysis of AOAC International. 16th Edition. vol. 1, Chapter 4, p. 4 (Jan. 4, 2010). AOAC Official Method 942.05 Ash of Animal Feed, 1997.

Aquatic Nutrition Inc., Chobi Soft Moist Food Mix, archived by the Internet Archive Wayback machine at https://web.archive.org/web/20130801043950/http://www.aquaticnutrition.com/chobi_moist_koi_food_mix.html, on Aug. 1, 2013, accessed Sep. 1, 2015.

Ashida et al., "Protection of Japanese Flounder *Paralichthys olivaceus* against Experimental Edwardsiellosis by Formalin-killed *Edwardsiella tarda* in Combination with Oral Administration of Immunostimulants," *Fisheries Science* 65(4):527-530, Aug. 1, 1999.

Booth, "Effects of Dietary and Free Bentonite on Ammonia Buildup in Aquarium Fish," *Australasian Journal of Ecotoxicology* 5:149-152, Jul. 1, 1999.

Casillas-Hernández et al., "Evaluación de NUTRIFITO™ como promotor natural en el alimento, para la producción comercial del camarón bianco del Pacifico *Litopenaeus vannamei*," Revista Latinoamericano de Recursos Naturales 5(2):174-179, 2009 with English language abstract.

Catalano et al., "Small bowel infarction by *Aspergillus*," *Haematologica* 82:182-183, Mar.-Apr. 1997, Mar. 1, 1997.

Derwent Publications Ltd., London, GB; XP002359382 & RU 2 115 421 C1 (Devichenskii V M) Jul. 20, 1998, abstract.

Derwent Publications Ltd., London, GB; XP002359383 & RU 2 093 162 C1 (AS SIBE Biochem Int) Oct. 20, 1997, abstract.

Dhabhar, "Enhancing versus Suppressive Effects of Stress on Immune Function: Implications for Immunoprotection and Immunopathology," *Neuroimmunomodulation* 16:300-317, published online Jun. 29, 2009.

Ellis et al., "Reduction of the bioavailability of 20 μm/kg aflatoxin in trout feed containing clay," *Aquaculture* 183(1-2):179-188, Mar. 1, 2000.

Fontaine et al., "Molecular Organization of the Alkali-insoluble Fraction of *Aspergillus fumigatus* Cell Wall," *J. Biol. Chem.* 275:27594-27607, Sep. 1, 2000.

Francis et al., "*Quillaja saponins*—a natural growth promoter for fish," *Animal Feed Science and Technology* 121(1-2): 147-157, Jun. 9, 2005.

Galon et al., "Gene profiling reveals unknown enhancing and suppressive actions of glucocorticoids on immune cells," *The FASEB Journal* 16:61-71, Jan. 2002.

Güroy et al., "Effect of dietary *Yucca schidigera* extract on growth, total ammonia-nitrogen excretion and haematological parameters of juvenile striped catfish *Pangasianodon hypophthalmus*," *Aquaculture Research* 45(4):647-654, Mar. 2014.

Hernández-Acosta et al., "The effects of *Yucca schidigera* and *Quillaja saponaria* on growth performance and enzymes activities of juvenile shrimp *Litopenaeus vannamei* cultured in low-salinity water," *Latin American Journal of Aquatic Research* 44(1):121-128, Mar. 1, 2016.

International Search Report dated Aug. 16, 2016 for PCT/US2015/015692, 6 pp.

International Search Report and Written Opinion dated Jan. 16, 2006 for PCT/US2005/028529, 9 pp.

International Search Report and Written Opinion dated Apr. 14, 2015 for PCT/US2015/015692, 9 pp.

Irianto et al., "Probiotics in aquaculture," *Journal of Fish Diseases* 25:1-10, Jan. 2002.

Kelly et al., "Effects of *Yucca shidigera* Extract on Growth, Nitrogen Retention, Ammonia Excretion, and Toxicity in Channel Catfish *Ictalurus punctatus* and Hybrid Tilapia *Oreochromis mossambicus* x *O. niloticus*," *Journal of the World Aquaculture Society* 34(2):156-161, Jun. 2003.

Kessler et al., "Glucomannan-protein complexes from cell walls of yeast," *Journal of Biological Chemistry* 234(9):2281-2285, Sep. 1959.

King et al., "A Targeted Glucocorticoid Receptor Antisense Transgene Increases Thymocyte Apoptosis and Alters Thymocyte Development," *Immunity* 3:647-656, Nov. 1, 1995.

Kumari et al., "Dietary β-1,3 glucan potentiates innate immunity and disease resistance in Asian catfish, *Clarias batrachus* (L.)," *Journal of Fish Diseases* 29:95-101,2006.

Lyons, "Biotechnology in the Feed Industry," Proceedings of Alltech's Eleventh Annual Symposium, edited by TP Lyons and KA Jacques, Nottingham University Press, pp. 1-29, Apr. 1995.

(56) References Cited

OTHER PUBLICATIONS

Mayer, "Cytokines and Immunoregulation," *Immunoregulation and Cytokines*, Immunology-Chapter Thirteen, pp. 1-5, updated Jul. 2010, downloaded from http://pathmicro.med.sc.edu/bowers/imm-reg-ver2.htm on Nov. 13, 2012.
Mostl et al., "Hormones as indicators of stress," *Domestic Animal Endocrinology* 23:67-74, Jul. 2002.
Omnigen AF Product Information at www.omnigenresearch.com/feed.php, accessed Jan. 27, 2008.
Peppler, "Production of Yeasts and Yeast Products," *Microbial Technology: Microbial Processes* 1(2):157-185, 1979.
Product Bulletin Cenzone Tech, Inc., Microbond, The Proven Micotoxin Adsorbent that Aids in the Binding and Diminishing the Adverse Effects of Mycotoxins, pp. 8-14, Dec. 9, 2005.
Product Bulletin, CIENDAX S.A. Pronady 500, 100% yeast cell wall (*Saccharomyces cerevisiae*), pp. 1-4, 2000.
Rea et al., "Glucocorticoids transform CD40-triggering of dendritic cells into an alternative activation pathway resulting in antigen-presenting cells that secrete IL-10," *Immunobiology* 95(10):3162-3167, May 15, 2000.
Santacruz-Reyes et al., "Efficacy of *Yucca schidigera* extract from ammonia reduction in fresh water: Effectiveness analysis and empirical modeling approach," *Aquaculture* 287:106-111, 2009.
Tangarone et al., "Purification and characterization of an endo-(1,3)-beta-D-glucanase from *Trichoderma longibrachiatum*," *Applied and Environmental Microbiology* 55(1):177-184, Jan. 1989.
"TLR-1:Toll-like Receptor 1," http://web.archive.org/web/20041210144234/http://www.invivogen.com/genedescription/ . . . , 2 pp., accessed Aug. 10, 2010.

Tort, "Stress and immune modulation in fish," *Developmental & Comparative Immunology* 35(12): 1366-1375, Dec. 31, 2011.
Travis, "Biologists Reveal the Proteins that First See Dangerous Microbes," *Science News* 160(10):152-158, Sep. 8, 2001.
U.S. Department of Health and Human Services Food and Drug Administration Center for Veterinary Medicine, Guidance for Industry, Dioxin in Anti-Caking Agent Used in Animal Feed and Feed Ingredients, Oct. 1999.
Valavanidis et al., "Molecular biomarkers of oxidative stress in aquatic organisms in relation to toxic environmental pollutants," *Ecotoxicology and Environmental Safety* 64(2): 178-189, Jun. 30, 2006.
Vetvicka, "β-Glucans as Immunomodulators," *JANA* 3(4):31-34, Winter 2001.
Wang et al., "Identification of the mechanisms by which Omnigen-AF, a nutritional supplement, augments immune function in ruminant livestock," *Proceedings, Western Section, American Society of Animal Sciences* 55:349-352, 2004.
Werling et al., "Differential Production of Cytokines, Reactive Oxygen and Nitrogen by Bovine Macrophages and Dendritic Cells Stimulated with Toll-like Receptor Agonists," *Immunology* 111:41-52, published online Dec. 15, 2003.
Xia et al., "The β-glucan-binding lectin site of mouse CR3 (CD11b/CD18) and its function in generating a primed state of the receptor that mediates cytotoxic activation in response to iC3b-opsonized target cells," *J. Immunol.* 162:2281, Feb. 15, 1999.
Zychowski et al., "The Effect of Aflatoxin-$B_1$ on Red Drum (*Sciaenops ocellatus*) and Assessment of Dietary Supplementation of NovaSil for the Prevention of Aflatoxicosis," *Toxins* 5:1555-1573, published online Sep. 16, 2013.

\* cited by examiner

| Culture stage | Feed type | Feed size (mm) | Feeding rate (%/BW/Day) | Dose of OM (mg Al/Kg BW/Day) | Dose of OM (mg/Kg feed) |
|---|---|---|---|---|---|
| Hatchery | Starter / Small feed | >0 - 1 / 1 - 2 | 10.0% | 100 | 1000 |

| Culture stage | Feed type | Feed size (mm) | Feeding rate (%/BW/Day) | Dose of OM (mg Al/Kg BW/Day) | Dose of OM (mg/Kg feed) |
|---|---|---|---|---|---|
| Nursery | Small pellets | 2 - 3 | 5.0% | 100 | 2000 |

| Culture stage | Feed type | Feed size (mm) | Feeding rate (%/BW/Day) | Dose of OM (mg Al/Kg BW/Day) | Dose of OM (mg/Kg feed) |
|---|---|---|---|---|---|
| Grow-out | Lg. Pellets | 3+ | 2.5% | 100 | 4000 |

| Example I: | Juveniles | At 10% feeding | Dose/Kg. Feed |
|---|---|---|---|
| | 1000 Kg. BW. | 100 Kg. feed | 1 Kg. feed |
| | 100 mg/Kg. BW/Day | | |
| | 100,000 mg./Day | 100000 mg | 1000 mg/Kg. feed |

| Example II: | Grow Out | At 2.5% feeding | Dose/Kg. Feed |
|---|---|---|---|
| | 1000 Kg. BW. | 25 Kg. feed | 1 Kg. feed |
| | 100 mg/Kg. BW/Day | | |
| | 100,000 mg./Day | 100000 mg | 4000 mg/Kg. feed |

FIG. 1

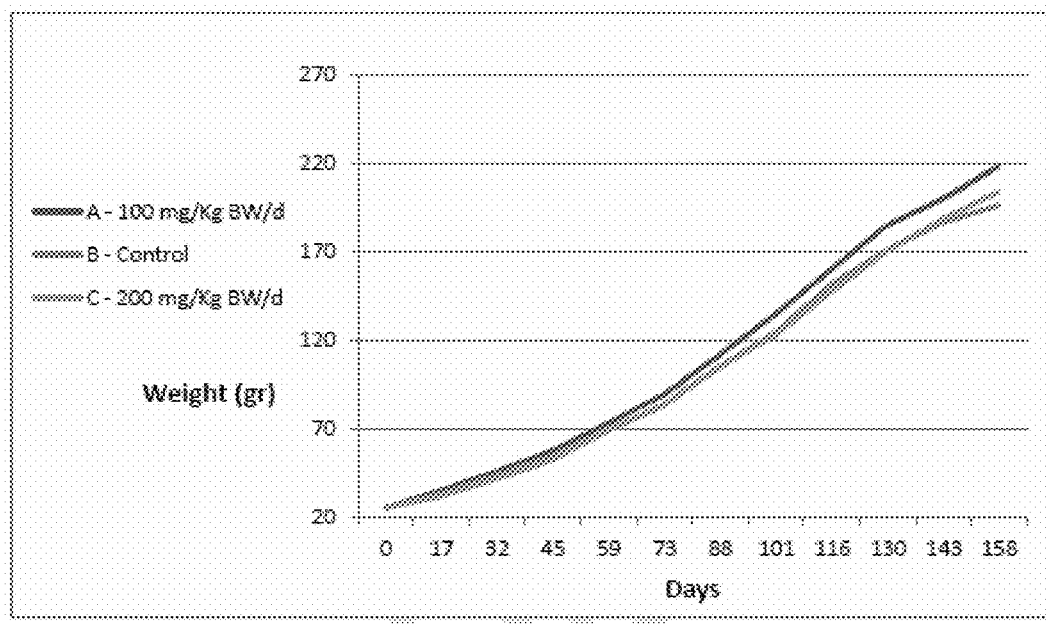

FIG. 2

| Day | Date | A | B | C |
|---|---|---|---|---|
| 0 | 27-06-14 | 26 | 26 | 26 |
| 17 | 14-07-14 | 36 | 34 | 33 |
| 32 | 29-07-14 | 46 | 45 | 42 |
| 45 | 11-08-14 | 58 | 55 | 53 |
| 59 | 25-08-14 | 74 | 70 | 70 |
| 73 | 08-09-14 | 90 | 84 | 84 |
| 88 | 23-09-14 | 112 | 105 | 106 |
| 101 | 06-10-14 | 135 | 125 | 123 |
| 116 | 21-10-14 | 160 | 152 | 148 |
| 130 | 04-11-14 | 185 | 171 | 171 |
| 143 | 17-11-14 | 200 | 187 | 189 |
| 158 | 02-12-14 | 218 | 196 | 204 |

FIG. 3

ANOVA: Single Factor A, B, C

SUMMARY

| Groups | Count | Sum | Average | Variance |
|---|---|---|---|---|
| Column 1 | 4 | 873.283 | 218.3208 | 66.59044 |
| Column 2 | 4 | 784.7163 | 196.1791 | 25.35359 |
| Column 3 | 4 | 815.2921 | 203.823 | 5.539316 |

ANOVA

| Source of Variation | SS | df | MS | F | P-value | F crit |
|---|---|---|---|---|---|---|
| Between Groups | 1011.824 | 2 | 505.9122 | 15.56919 | 0.001197 | 4.256495 |
| Within Groups | 292.45 | 9 | 32.49445 | | | |
| Total | 1304.274 | 11 | | | | |

FIG. 4

| FCR values per treatment and tanks | | |
|---|---|---|
| A | B | C |
| 1.51 | 1.62 | 1.50 |
| 1.54 | 1.64 | 1.61 |
| 1.58 | 1.76 | 1.49 |
| 1.50 | 1.56 | 1.56 |

| Average | 1.53 | 1.65 | 1.54 |
|---|---|---|---|

FIG. 5

| Date | Day | pH | Nitrite (ppm) | Ammonia (ppm) | Oxygen (ppm) | Temp (°C) | Total salinity (ppt) |
|---|---|---|---|---|---|---|---|
| 27-06-14 | 1 | 7.4 | 0.0 | 0.0 | 7.6 | 23.9 | 18.0 |
| 04-07-14 | 7 | 7.4 | 0.0 | 0.0 | 7.7 | 24.0 | 18.0 |
| 11-07-14 | 14 | 7.4 | 0.0 | 0.0 | 7.6 | 24.1 | 18.0 |
| 18-07-14 | 21 | 7.4 | 0.0 | 0.0 | 7.2 | 24.1 | 18.0 |
| 25-07-14 | 28 | 7.4 | 0.0 | 0.0 | 7.0 | 24.2 | 18.0 |
| 01-08-14 | 35 | 7.4 | 0.0 | 0.0 | 7.2 | 24.2 | 18.0 |
| 08-08-14 | 42 | 7.5 | 0.0 | 0.0 | 7.1 | 24.3 | 18.0 |
| 15-08-14 | 49 | 7.5 | 0.0 | 0.0 | 6.9 | 24.4 | 18.0 |
| 22-08-14 | 56 | 7.5 | 0.0 | 0.0 | 7.4 | 24.4 | 18.0 |
| 29-08-14 | 63 | 7.4 | 0.0 | 0.0 | 7.3 | 24.2 | 18.0 |
| 05-09-14 | 70 | 7.4 | 0.0 | 0.0 | 7.2 | 23.9 | 18.0 |
| 12-09-14 | 77 | 7.5 | 0.0 | 0.0 | 7.3 | 23.6 | 18.0 |
| 19-09-14 | 84 | 7.4 | 0.0 | 0.0 | 7.0 | 23.3 | 18.0 |
| 26-09-14 | 91 | 7.5 | 0.0 | 0.0 | 7.0 | 23.3 | 18.0 |
| 03-10-14 | 98 | 7.4 | 0.0 | 0.0 | 6.9 | 22.9 | 18.0 |
| 10-10-14 | 105 | 7.4 | 0.0 | 0.0 | 7.8 | 22.3 | 18.0 |
| 17-10-14 | 112 | 7.4 | 0.0 | 0.0 | 7.2 | 22.3 | 18.0 |
| 24-10-14 | 119 | 7.4 | 0.0 | 0.0 | 7.5 | 22.2 | 18.0 |
| 31-10-14 | 126 | 7.4 | 0.0 | 0.0 | 7.5 | 22.2 | 18.0 |
| 07-11-14 | 133 | 7.5 | 0.2 | 0.0 | 8.0 | 21.1 | 18.0 |
| 14-11-14 | 140 | 7.5 | 0.2 | 0.0 | 7.5 | 20.9 | 18.0 |
| 21-11-14 | 147 | 7.4 | 0.2 | 0.0 | 7.3 | 20.7 | 18.0 |
| 28-11-14 | 154 | 7.4 | 0.2 | 0.0 | 7.8 | 21.0 | 18.0 |

FIG. 6

| Fish weight (gr) | Feeding rate (%) for Sea bream by Temperature | | | | |
|---|---|---|---|---|---|
| | 17c | 19c | 21c | 23c | 25c |
| 1-3 | 2.8 | 4.1 | 5.4 | 5.8 | 5.9 |
| 3-8 | 2.2 | 3.2 | 4.2 | 4.5 | 4.6 |
| 8-15 | 1.7 | 2.5 | 3.3 | 3.5 | 3.6 |
| 15-30 | 1.5 | 2.2 | 2.9 | 3.1 | 3.2 |
| 30-50 | 1.3 | 1.9 | 2.5 | 2.7 | 2.7 |
| 50-100 | 1.1 | 1.7 | 2.2 | 2.4 | 2.4 |
| 100-150 | 0.9 | 1.4 | 1.8 | 2.0 | 2.0 |
| 150-200 | 0.8 | 1.2 | 1.6 | 1.7 | 1.7 |
| 200-300 | 0.7 | 1.0 | 1.3 | 1.4 | 1.4 |
| 300-400 | 0.6 | 0.9 | 1.2 | 1.2 | 1.2 |
| 400-500 | 0.5 | 0.7 | 1.0 | 1.0 | 1.0 |
| 500-600 | 0.5 | 0.7 | 0.9 | 0.9 | 1.0 |
| 600-700 | 0.4 | 0.6 | 0.8 | 0.8 | 0.9 |

| Day | Tank No<br>Treatment | 1<br>A | 2<br>A | 3<br>A | 4<br>A | 5<br>B | 6<br>B | 7<br>B | 8<br>B | 9<br>C | 10<br>C | 11<br>C | 12<br>C |
|---|---|---|---|---|---|---|---|---|---|---|---|---|---|
| 0 | 27-06-14 | 26 | 26 | 26 | 26 | 26 | 26 | 26 | 26 | 26 | 26 | 26 | 26 |
| 17 | 14-07-14 | 37 | 35 | 37 | 35 | 35 | 35 | 34 | 32 | 29 | 35 | 33 | 33 |
| 32 | 29-07-14 | 46 | 45 | 48 | 46 | 45 | 45 | 45 | 43 | 38 | 46 | 43 | 43 |
| 45 | 11-08-14 | 59 | 56 | 60 | 57 | 56 | 56 | 56 | 53 | 48 | 57 | 53 | 54 |
| 59 | 25-08-14 | 77 | 72 | 75 | 72 | 70 | 72 | 71 | 67 | 72 | 71 | 67 | 69 |
| 73 | 08-09-14 | 92 | 86 | 91 | 90 | 83 | 87 | 84 | 83 | 85 | 88 | 80 | 83 |
| 88 | 23-09-14 | 115 | 106 | 115 | 112 | 103 | 110 | 103 | 104 | 107 | 109 | 101 | 105 |
| 101 | 06-10-14 | 140 | 128 | 137 | 135 | 122 | 129 | 123 | 125 | 128 | 121 | 120 | 124 |
| 116 | 21-10-14 | 166 | 153 | 159 | 163 | 147 | 158 | 152 | 150 | 152 | 146 | 144 | 148 |
| 130 | 04-11-14 | 193 | 176 | 183 | 188 | 169 | 173 | 172 | 171 | 175 | 169 | 165 | 173 |
| 143 | 17-11-14 | 203 | 191 | 199 | 208 | 187 | 187 | 186 | 187 | 195 | 186 | 183 | 191 |
| 158 | 02-12-14 | 225 | 212 | 211 | 225 | 193 | 199 | 191 | 202 | 206 | 202 | 202 | 205 |

FIG. 9

ANOVA: Single Factor A, B, C - day 18

SUMMARY

| Groups | Count | Sum | Average | Variance |
|---|---|---|---|---|
| 37.03704 | 3 | 106.1818 | 35.39394 | 1.356391 |
| 34.54545 | 3 | 101.6715 | 33.89048 | 2.131385 |
| 29.09091 | 3 | 101.1938 | 33.73128 | 1.137893 |

ANOVA

| Source of Variation | SS | df | MS | F | P-value | F crit |
|---|---|---|---|---|---|---|
| Between Groups | 5.050179 | 2 | 2.52509 | 1.634126 | 0.271307 | 5.143253 |
| Within Groups | 9.271339 | 6 | 1.545223 | | | |
| Total | 14.32152 | 8 | | | | |

FIG. 10A

ANOVA: Single Factor A, B, C - day 33

SUMMARY

| Groups | Count | Sum | Average | Variance |
|---|---|---|---|---|
| 157.1429 | 5 | 786.0084 | 157.2017 | 19.82522 |
| 155.8824 | 5 | 752.8571 | 150.5714 | 17.95918 |
| 147.1429 | 5 | 754.2017 | 150.8403 | 11.99421 |

ANOVA

| Source of Variation | SS | df | MS | F | P-value | F crit |
|---|---|---|---|---|---|---|
| Between Groups | 140.8321 | 2 | 70.41605 | 4.243753 | 0.040379 | 3.885294 |
| Within Groups | 199.1145 | 12 | 16.59287 | | | |
| Total | 339.9466 | 14 | | | | |

FIG. 10B

ANOVA: Single Factor A, B, C - day 46

SUMMARY

| Groups | Count | Sum | Average | Variance |
|---|---|---|---|---|
| 59.24528 | 3 | 173.0909 | 57.69697 | 2.953168 |
| 55.63636 | 3 | 164.8804 | 54.96013 | 2.631564 |
| 47.63636 | 3 | 164.3725 | 54.79084 | 4.155444 |

ANOVA

| Source of Variation | SS | df | MS | F | P-value | F crit |
|---|---|---|---|---|---|---|
| Between Groups | 15.96453 | 2 | 7.982266 | 2.458559 | 0.166008 | 5.143253 |
| Within Groups | 19.48035 | 6 | 3.246725 | | | |
| Total | 35.44488 | 8 | | | | |

FIG. 10C

ANOVA: Single Factor A, B, C - day 60

SUMMARY

| Groups | Count | Sum | Average | Variance |
|---|---|---|---|---|
| Column 1 | 4 | 294.7856 | 73.6964 | 5.431746 |
| Column 2 | 4 | 279.2408 | 69.81021 | 5.090004 |
| Column 3 | 4 | 281.1022 | 70.27555 | 8.808258 |

ANOVA

| Source of Variation | SS | df | MS | F | P-value | F crit |
|---|---|---|---|---|---|---|
| Between Groups | 36.02826 | 2 | 18.01413 | 2.795777 | 0.113667 | 4.256495 |
| Within Groups | 57.99002 | 9 | 6.443336 | | | |
| Total | 94.01828 | 11 | | | | |

FIG. 10D

ANOVA: Single Factor A, B, C - day 64

SUMMARY

| Groups | Count | Sum | Average | Variance |
|---|---|---|---|---|
| Column 1 | 4 | 359.3619 | 89.84048 | 8.351695 |
| Column 2 | 4 | 336.236 | 84.05901 | 2.808574 |
| Column 3 | 4 | 336.8891 | 84.22229 | 11.02519 |

ANOVA

| Source of Variation | SS | df | MS | F | P-value | F crit |
|---|---|---|---|---|---|---|
| Between Groups | 86.6882 | 2 | 43.3441 | 5.861149 | 0.023449 | 4.256495 |
| Within Groups | 66.55639 | 9 | 7.395154 | | | |
| Total | 153.2446 | 11 | | | | |

FIG. 10E

ANOVA: Single Factor A, B, C - day 89

SUMMARY

| Groups | Count | Sum | Average | Variance |
|---|---|---|---|---|
| Column 1 | 4 | 447.8216 | 111.9554 | 17.33775 |
| Column 2 | 4 | 420.6124 | 105.1531 | 9.967629 |
| Column 3 | 4 | 422.0678 | 105.517 | 12.62426 |

ANOVA

| Source of Variation | SS | df | MS | F | P-value | F crit |
|---|---|---|---|---|---|---|
| Between Groups | 117.1428 | 2 | 58.5714 | 4.400595 | 0.046459 | 4.256495 |
| Within Groups | 119.7889 | 9 | 13.30988 | | | |
| Total | 236.9317 | 11 | | | | |

FIG. 10F

ANOVA: Single Factor A, B, C - day 101

SUMMARY

| Groups | Count | Sum | Average | Variance |
|---|---|---|---|---|
| Column 1 | 4 | 539.6501 | 134.9125 | 28.70008 |
| Column 2 | 4 | 498.1673 | 124.5418 | 9.340095 |
| Column 3 | 4 | 493.3201 | 123.33 | 11.356 |

ANOVA

| Source of Variation | SS | df | MS | F | P-value | F crit |
|---|---|---|---|---|---|---|
| Between Groups | 324.232 | 2 | 162.116 | 9.845862 | 0.005422 | 4.256495 |
| Within Groups | 148.1885 | 9 | 16.46539 | | | |
| Total | 472.4205 | 11 | | | | |

FIG. 10G

| ANOVA: Single Factor A, B, C - day 116 | | | | | | |
|---|---|---|---|---|---|---|
| SUMMARY | | | | | | |
| Groups | Count | Sum | Average | Variance | | |
| Column 1 | 4 | 640.9605 | 160.2401 | 34.48941 | | |
| Column 2 | 4 | 606.6766 | 151.6691 | 23.45402 | | |
| Column 3 | 4 | 590.5701 | 147.6425 | 12.97135 | | |
| | | | | | | |
| ANOVA | | | | | | |
| Source of Variation | SS | df | MS | F | P-value | F crit |
| Between Groups | 331.1671 | 2 | 165.5836 | 7.004896 | 0.014638 | 4.256495 |
| Within Groups | 212.7444 | 9 | 23.63826 | | | |

FIG. 10H

| ANOVA: Single Factor A, B, C - day 130 | | | | | | |
|---|---|---|---|---|---|---|
| SUMMARY | | | | | | |
| Groups | Count | Sum | Average | Variance | | |
| Column 1 | 4 | 740.4666 | 185.1166 | 50.51005 | | |
| Column 2 | 4 | 684.1446 | 171.0362 | 2.830353 | | |
| Column 3 | 4 | 682.4245 | 170.6061 | 17.91724 | | |
| | | | | | | |
| ANOVA | | | | | | |
| Source of Variation | SS | df | MS | F | P-value | F crit |
| Between Groups | 545.3334 | 2 | 272.6667 | 11.47947 | 0.003338 | 4.256495 |
| Within Groups | 213.7729 | 9 | 23.75255 | | | |
| | | | | | | |
| Total | 759.1063 | 11 | | | | |

FIG. 10I

| ANOVA: Single Factor A, B, C - day 143 | | | | | | |
|---|---|---|---|---|---|---|
| SUMMARY | | | | | | |
| Groups | Count | Sum | Average | Variance | | |
| Column 1 | 4 | 800.4734 | 200.1184 | 52.60595 | | |
| Column 2 | 4 | 746.8006 | 186.7002 | 0.166877 | | |
| Column 3 | 4 | 755.0425 | 188.7606 | 29.08882 | | |
| ANOVA | | | | | | |
| Source of Variation | SS | df | MS | F | P-value | F crit |
| Between Groups | 417.7219 | 2 | 208.861 | 7.654168 | 0.011434 | 4.256495 |
| Within Groups | 245.585 | 9 | 27.28722 | | | |
| Total | 663.3069 | 11 | | | | |

FIG. 10J

| Tank | Initial Av (gr) | Initial No of fish | Initial Biomass (gr) | Final No of fish | Final Av (gr) | Final Biomass (gr) | Mortality (gr) | Gain (gr) | Fed (gr) | FCR | FCR by group |
|---|---|---|---|---|---|---|---|---|---|---|---|
| 1 | 26 | 55 | 1,430 | 54 | 225 | 12,165 | 52 | 10,787 | 16,288 | 1.51 | |
| 2 | 26 | 55 | 1,430 | 55 | 212 | 11,660 | | 10,230 | 15,773 | 1.54 | 1.53 |
| 3 | 26 | 55 | 1,430 | 55 | 211 | 11,580 | | 10,150 | 16,020 | 1.58 | |
| 4 | 26 | 55 | 1,430 | 55 | 225 | 12,400 | | 10,970 | 16,503 | 1.50 | |
| 5 | 26 | 55 | 1,430 | 55 | 193 | 10,600 | | 9,170 | 14,880 | 1.62 | |
| 6 | 26 | 55 | 1,430 | 55 | 199 | 10,940 | | 9,510 | 15,567 | 1.64 | 1.65 |
| 7 | 26 | 55 | 1,430 | 55 | 191 | 10,518 | | 9,088 | 15,996 | 1.76 | |
| 8 | 26 | 55 | 1,430 | 54 | 202 | 10,900 | 110 | 9,580 | 14,980 | 1.56 | |
| 9 | 26 | 55 | 1,430 | 54 | 206 | 11,146 | 128 | 9,844 | 14,786 | 1.50 | |
| 10 | 26 | 55 | 1,430 | 55 | 202 | 11,120 | | 9,690 | 15,578 | 1.61 | 1.54 |
| 11 | 26 | 55 | | | 202 | | | | 14,383 | 1.49 | |
| | | | 1,430 | 55 | | 11,083 | | 9,653 | | | |
| 12 | 26 | 55 | 1,430 | 54 | 205 | 11,080 | 40 | 9,690 | 15,161 | 1.56 | |
| Average | | | 1,430 | | | 11,266 | 83 | 9,919 | 15,493 | 1.57 | 1.57 |

FIG. 11

| Fish mortality per cage per treatment | | |
|---|---|---|
| A | B | C |
| 1 | 0 | 1 |
| 0 | 0 | 0 |
| 0 | 0 | 0 |
| 0 | 1 | 1 |

| | A | B | C |
|---|---|---|---|
| Total | 1 | 1 | 2 |
| Survival (%) | 99.5% | 99.5% | 99.1% |

FIG. 12A

| Day | Date | 1 | 2 | 3 | 4 | 5 | 6 | 7 | 8 | 9 | 10 | 11 | 12 |
|---|---|---|---|---|---|---|---|---|---|---|---|---|---|
| 0 | 27-06-14 | | | | | | | | | | | | |
| 1 | 28-06-14 | | | | | | | | | | | | |
| 2 | 29-06-14 | | | | | | | | | | | | |
| 3 | 30-06-14 | | | | | | | | | | | | |
| 32 | 29-07-14 | | | | | | | | | | | | |
| 33 | 30-07-14 | | | | | | | | | | | | |
| 34 | 31-07-14 | | | | | | | | | | | | | 1 |
| 35 | 01-08-14 | 1 | | | | | | | | | | | |
| 93 | 28-09-14 | | | | | | | | 1 | | | | |
| 94 | 29-09-14 | | | | | | | | | | | | |
| 95 | 30-09-14 | | | | | | | | | | | | |
| 96 | 01-10-14 | | | | | | | | | | | | |
| 97 | 02-10-14 | | | | | | | | | | | | |
| 98 | 03-10-14 | | | | | | | | | | | | |
| 99 | 04-10-14 | | | | | | | | | | | | |
| 100 | 05-10-14 | | | | | | | | | 1 | | | |
| 158 | 02-12-14 | | | | | | | | | | | | |
| End of trial | | 1 | 0 | 0 | 0 | 0 | 0 | 0 | 1 | 1 | 0 | 0 | 1 |

FIG. 12B

| Day | Date | A – 100 mg/Kg | B – Control | C – 200 mg/Kg | Reference |
|---|---|---|---|---|---|
| 0 | 09-06-14 | 95 | 95 | 95 | 95 |
| 16 | 25-06-14 | 126 | 124 | 122 | 123 |
| 30 | 09-07-14 | 157 | 151 | 150 | 152 |
| 44 | 23-07-14 | 197 | 187 | 186 | 186 |
| 58 | 06-08-14 | 245 | 238 | 236 | 223 |
| 72 | 20-08-14 | 288 | 283 | 281 | 260 |
| 86 | 03-09-14 | 333 | 315 | 321 | 304 |
| 100 | 17-09-14 | 389 | 363 | 360 | 352 |
| 114 | 01-10-14 | 431 | 398 | 390 | 390 |
| 128 | 22-10-14 | 483 | 451 | 445 | 415 |
| 149 | 05-11-14 | 502 | 461 | 457 | 435 |

FIG. 15

ANOVA: Single Factor A, B, C

SUMMARY

| Groups | Count | Sum | Average | Variance |
|---|---|---|---|---|
| Column 1 | 6 | 3011.026 | 501.8377 | 576.4098 |
| Column 2 | 6 | 2765.023 | 460.8372 | 583.5461 |
| Column 3 | 6 | 2740.008 | 456.6679 | 229.9323 |

ANOVA

| Source of Variation | SS | df | MS | F | P-value | F crit |
|---|---|---|---|---|---|---|
| Between Groups | 7477.474 | 2 | 3738.737 | 8.069866 | 0.004177 | 3.68232 |
| Within Groups | 6949.441 | 15 | 463.2961 | | | |
| Total | 14426.92 | 17 | | | | |

FIG. 16

| FCR values per treatment and cages |||
|---|---|---|
| A – 100 mg/Kg | B – Control | C – 200 mg/Kg |
| 1.82 | 1.90 | 1.93 |
| 1.83 | 1.84 | 1.91 |
| 1.85 | 1.78 | 1.86 |
| 1.80 | 2.06 | 1.92 |
| 1.69 | 1.97 | 1.94 |
| 1.70 | 1.87 | 1.86 |
| Average | 1.78 | 1.90 | 1.91 |

FIG. 17

ANOVA: Single Factor FCR for A, B, C

SUMMARY

| Groups | Count | Sum | Average | Variance |
|---|---|---|---|---|
| Column 1 | 6 | 10.68655 | 1.781092 | 0.004939 |
| Column 2 | 6 | 11.42313 | 1.903855 | 0.009916 |
| Column 3 | 6 | 11.43043 | 1.905072 | 0.001272 |

ANOVA

| Source of Variation | SS | df | MS | F | P-value | F crit |
|---|---|---|---|---|---|---|
| Between Groups | 0.060886 | 2 | 0.030443 | 5.662922 | 0.014717 | 3.68232 |
| Within Groups | 0.080638 | 15 | 0.005376 | | | |
| Total | 0.141524 | 17 | | | | |

FIG. 18

| Date | Day | pH | Nitrite (ppm) | Ammonia (ppm) | Oxygen (ppm) | Temp (°C) |
|---|---|---|---|---|---|---|
| 09-06-14 | 1 | 7.6 | 0.4 | 0.1 | 6.4 | 27.5 |
| 16-06-14 | 7 | 7.6 | 1.0 | 0.2 | 6.1 | 27.5 |
| 23-06-14 | 14 | 7.6 | 1.0 | 0.5 | 6.0 | 27.0 |
| 30-06-14 | 21 | 7.6 | 0.8 | 0.4 | 5.8 | 27.0 |
| 07-07-14 | 28 | 7.6 | 1.0 | 0.4 | 5.5 | 27.5 |
| 14-07-14 | 35 | 7.6 | 1.0 | 0.3 | 5.5 | 27.0 |
| 21-07-14 | 42 | 7.6 | 0.5 | 0.1 | 5.6 | 27.5 |
| 28-07-14 | 49 | 7.5 | 0.5 | 0.1 | 5.5 | 27.5 |
| 04-08-14 | 56 | 7.6 | 0.3 | 0.1 | 5.8 | 27.0 |
| 11-08-14 | 63 | 7.6 | 0.2 | 0.1 | 6.0 | 27.0 |
| 18-08-14 | 70 | 7.6 | 0.3 | 0.1 | 6.0 | 27.8 |
| 25-08-14 | 77 | 7.6 | 0.3 | 0.1 | 6.0 | 28.0 |
| 01-09-14 | 84 | 7.5 | 0.4 | 0.1 | 6.5 | 26.7 |
| 08-09-14 | 91 | 7.5 | 0.5 | 0.2 | 6.5 | 26.2 |
| 15-09-14 | 98 | 7.6 | 0.8 | 0.5 | 6.5 | 25.5 |
| 22-09-14 | 105 | 7.7 | 0.5 | 0.2 | 6.5 | 25.1 |
| 29-09-14 | 112 | 7.6 | 0.2 | 0.2 | 6.4 | 25.6 |
| 06-10-14 | 119 | 7.5 | 0.2 | 0.2 | 6.4 | 24.0 |
| 13-10-14 | 126 | 7.5 | 0.2 | 0.2 | 6.6 | 24.5 |
| 20-10-14 | 133 | 7.6 | 0.3 | 0.3 | 6.7 | 22.8 |
| 27-10-14 | 140 | 7.5 | 0.4 | 0.3 | 6.7 | 23.2 |
| 03-11-14 | 147 | 7.5 | 0.4 | 0.3 | 6.5 | 22.8 |

FIG. 19

Feeding chart for Tilapia (Oreochromis niloticus) - Temperature 28c

| Day | Weight (gr) | Growth (gr/d) | FCR | Feed (gr/d) | Feed (%/d) | Day | Weight (gr) | Growth (gr/d) | FCR | Feed (gr/d) | Feed (%/d) |
|---|---|---|---|---|---|---|---|---|---|---|---|
| 1 | 0.10 | 0.01 | 1.21 | 0.01 | 12% | 46 | 2.63 | 0.16 | 1.26 | 0.20 | 7.7% |
| 2 | 0.11 | 0.01 | 1.21 | 0.01 | 12% | 47 | 2.79 | 0.17 | 1.26 | 0.21 | 7.6% |
| 3 | 0.12 | 0.01 | 1.21 | 0.01 | 12% | 48 | 2.96 | 0.18 | 1.26 | 0.22 | 7.5% |
| 4 | 0.13 | 0.01 | 1.21 | 0.02 | 12% | 49 | 3.14 | 0.19 | 1.26 | 0.23 | 7.4% |
| 5 | 0.15 | 0.01 | 1.21 | 0.02 | 11% | 50 | 3.32 | 0.19 | 1.26 | 0.24 | 7.4% |
| 6 | 0.16 | 0.01 | 1.21 | 0.02 | 11% | 51 | 3.52 | 0.20 | 1.27 | 0.26 | 7.3% |
| 7 | 0.17 | 0.02 | 1.22 | 0.02 | 11% | 52 | 3.72 | 0.21 | 1.27 | 0.27 | 7.2% |
| 8 | 0.19 | 0.02 | 1.22 | 0.02 | 11% | 53 | 3.93 | 0.22 | 1.27 | 0.28 | 7.2% |
| 9 | 0.21 | 0.02 | 1.22 | 0.02 | 9.8% | 54 | 4.15 | 0.23 | 1.27 | 0.29 | 7.1% |
| 10 | 0.22 | 0.02 | 1.22 | 0.02 | 9.8% | 55 | 4.38 | 0.24 | 1.27 | 0.31 | 7.0% |
| 11 | 0.24 | 0.02 | 1.22 | 0.02 | 9.5% | 56 | 4.62 | 0.25 | 1.27 | 0.32 | 6.9% |
| 12 | 0.26 | 0.02 | 1.22 | 0.02 | 9.3% | 57 | 4.87 | 0.26 | 1.27 | 0.33 | 6.8% |
| 13 | 0.28 | 0.02 | 1.22 | 0.03 | 9.2% | 58 | 5.13 | 0.27 | 1.27 | 0.34 | 6.7% |
| 14 | 0.30 | 0.02 | 1.22 | 0.03 | 9.2% | 59 | 5.41 | 0.28 | 1.28 | 0.36 | 6.7% |
| 15 | 0.32 | 0.02 | 1.22 | 0.03 | 9.2% | 60 | 5.69 | 0.29 | 1.28 | 0.38 | 6.6% |
| 16 | 0.35 | 0.03 | 1.22 | 0.03 | 9.2% | 61 | 5.98 | 0.31 | 1.28 | 0.39 | 6.5% |
| 17 | 0.37 | 0.03 | 1.23 | 0.03 | 9.1% | 62 | 6.29 | 0.32 | 1.28 | 0.41 | 6.5% |
| 18 | 0.40 | 0.03 | 1.23 | 0.04 | 9.1% | 63 | 6.60 | 0.33 | 1.28 | 0.42 | 6.4% |
| 19 | 0.43 | 0.03 | 1.23 | 0.04 | 9.1% | 64 | 6.94 | 0.34 | 1.28 | 0.44 | 6.3% |
| 20 | 0.46 | 0.03 | 1.23 | 0.04 | 9.1% | 65 | 7.28 | 0.36 | 1.28 | 0.46 | 6.3% |
| 21 | 0.50 | 0.04 | 1.23 | 0.04 | 9.0% | 66 | 7.64 | 0.37 | 1.28 | 0.48 | 6.2% |
| 22 | 0.53 | 0.04 | 1.23 | 0.05 | 9.0% | 67 | 8.01 | 0.39 | 1.29 | 0.50 | 6.2% |
| 23 | 0.57 | 0.04 | 1.23 | 0.05 | 9.0% | 68 | 8.39 | 0.40 | 1.29 | 0.52 | 6.1% |
| 24 | 0.61 | 0.04 | 1.23 | 0.06 | 9.0% | 69 | 8.79 | 0.41 | 1.29 | 0.53 | 6.1% |
| 25 | 0.66 | 0.05 | 1.23 | 0.06 | 8.9% | 70 | 9.21 | 0.43 | 1.29 | 0.55 | 6.0% |
| 26 | 0.71 | 0.05 | 1.24 | 0.06 | 8.9% | 71 | 9.64 | 0.44 | 1.29 | 0.57 | 5.9% |
| 27 | 0.76 | 0.05 | 1.24 | 0.07 | 8.9% | 72 | 10.08 | 0.46 | 1.29 | 0.59 | 5.9% |
| 28 | 0.81 | 0.06 | 1.24 | 0.07 | 8.9% | 73 | 10.54 | 0.48 | 1.30 | 0.62 | 5.9% |
| 29 | 0.87 | 0.06 | 1.24 | 0.08 | 8.8% | 74 | 11.02 | 0.49 | 1.30 | 0.64 | 5.8% |
| 30 | 0.93 | 0.07 | 1.24 | 0.08 | 8.8% | 75 | 11.51 | 0.51 | 1.30 | 0.66 | 5.7% |
| 31 | 1.00 | 0.07 | 1.24 | 0.09 | 8.8% | 76 | 12.01 | 0.52 | 1.30 | 0.68 | 5.7% |
| 32 | 1.07 | 0.08 | 1.24 | 0.09 | 8.8% | 77 | 12.54 | 0.54 | 1.30 | 0.70 | 5.6% |
| 33 | 1.14 | 0.08 | 1.24 | 0.10 | 8.7% | 78 | 13.08 | 0.56 | 1.31 | 0.73 | 5.6% |
| 34 | 1.22 | 0.09 | 1.24 | 0.11 | 8.6% | 79 | 13.64 | 0.57 | 1.31 | 0.75 | 5.5% |
| 35 | 1.31 | 0.09 | 1.25 | 0.11 | 8.6% | 80 | 14.21 | 0.59 | 1.31 | 0.77 | 5.4% |
| 36 | 1.40 | 0.10 | 1.25 | 0.12 | 8.5% | 81 | 14.80 | 0.61 | 1.31 | 0.80 | 5.4% |
| 37 | 1.50 | 0.10 | 1.25 | 0.13 | 8.4% | 82 | 15.41 | 0.63 | 1.32 | 0.83 | 5.4% |
| 38 | 1.60 | 0.11 | 1.25 | 0.13 | 8.4% | 83 | 16.03 | 0.64 | 1.32 | 0.85 | 5.3% |
| 39 | 1.70 | 0.11 | 1.25 | 0.14 | 8.3% | 84 | 16.68 | 0.66 | 1.32 | 0.87 | 5.2% |
| 40 | 1.82 | 0.12 | 1.25 | 0.15 | 8.2% | 85 | 17.34 | 0.68 | 1.33 | 0.90 | 5.2% |
| 41 | 1.93 | 0.13 | 1.25 | 0.16 | 8.1% | 86 | 18.02 | 0.70 | 1.33 | 0.92 | 5.1% |
| 42 | 2.06 | 0.13 | 1.25 | 0.16 | 8.0% | 87 | 18.73 | 0.71 | 1.33 | 0.95 | 5.1% |
| 43 | 2.19 | 0.14 | 1.26 | 0.17 | 8.0% | 88 | 19.82 | 0.73 | 1.33 | 0.97 | 5.0% |
| 44 | 2.33 | 0.15 | 1.26 | 0.18 | 7.9% | 89 | 20.15 | 0.75 | 1.33 | 0.99 | 4.9% |
| 45 | 2.48 | 0.15 | 1.26 | 0.19 | 7.8% | 90 | 20.90 | 0.77 | 1.33 | 1.02 | 4.9% |

FIG. 21

| Day | Cage | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| | Treatment | A | A | B | B | C | C | A | A | B | B | C | C | A | A | B | B | C | C |
| 0 | 09-06-14 | 95 | 95 | 95 | 95 | 95 | 95 | 95 | 95 | 95 | 95 | 95 | 95 | 95 | 95 | 95 | 95 | 95 | 95 |
| 16 | 25-06-14 | 129 | 119 | 129 | 137 | 123 | 124 | 131 | 136 | 116 | 129 | 130 | 129 | 129 | 121 | 135 | 131 | 117 | 119 |
| 30 | 09-07-14 | 157 | 153 | 156 | 154 | 147 | 153 | 163 | 157 | 146 | 156 | 147 | 154 | 160 | 153 | 149 | 149 | 147 | 153 |
| 44 | 23-07-14 | 183 | 184 | 184 | 179 | 180 | 184 | 200 | 224 | 206 | 187 | 180 | 194 | 206 | 184 | 183 | 184 | 185 | 194 |
| 58 | 06-08-14 | 239 | 237 | 238 | 240 | 219 | 231 | 251 | 252 | 234 | 243 | 234 | 250 | 261 | 231 | 239 | 234 | 232 | 249 |
| 72 | 20-08-14 | 280 | 273 | 269 | 284 | 261 | 279 | 294 | 294 | 274 | 290 | 279 | 294 | 309 | 279 | 286 | 298 | 276 | 299 |
| 86 | 03-09-14 | 337 | 313 | 320 | 320 | 302 | 327 | 322 | 348 | 315 | 302 | 320 | 320 | 350 | 328 | 315 | 317 | 323 | 333 |
| 100 | 17-09-14 | 388 | 355 | 367 | 366 | 347 | 360 | 378 | 393 | 372 | 335 | 358 | 343 | 431 | 385 | 358 | 378 | 368 | 382 |
| 114 | 01-10-14 | 438 | 413 | 398 | 410 | 381 | 400 | 420 | 412 | 400 | 382 | 397 | 373 | 464 | 442 | 383 | 417 | 403 | 388 |
| 135 | 22-10-14 | 480 | 439 | 448 | 452 | 423 | 445 | 500 | 473 | 448 | 440 | 448 | 431 | 507 | 500 | 433 | 483 | 448 | 473 |
| 149 | 05-11-14 | 490 | 471 | 458 | 471 | 434 | 458 | 488 | 503 | 488 | 425 | 469 | 453 | 538 | 520 | 442 | 481 | 450 | 477 |

FIG. 22

Anova: Single Factor A, B, C - day 16

SUMMARY

| Groups | Count | Sum | Average | Variance |
|---|---|---|---|---|
| Column 1 | 6 | 755.1429 | 125.8571 | 22.98776 |
| Column 2 | 6 | 745.8333 | 124.3056 | 26.15882 |
| Column 3 | 6 | 731.9748 | 121.9958 | 17.00851 |

ANOVA

| Source of Variation | SS | df | MS | F | P-value | F crit |
|---|---|---|---|---|---|---|
| Between Groups | 45.30477 | 2 | 22.65238 | 1.02724 | 0.381853 | 3.68232 |
| Within Groups | 330.7754 | 15 | 22.0517 | | | |
| Total | 376.0802 | 17 | | | | |

FIG. 23A

| ANOVA: Single Factor A, B, C - day 30 | | | | | | |
|---|---|---|---|---|---|---|
| SUMMARY | | | | | | |
| Groups | Count | Sum | Average | Variance | | |
| 157.1429 | 5 | 786.0084 | 157.2017 | 19.82522 | | |
| 155.8824 | 5 | 752.8571 | 150.5714 | 17.95918 | | |
| 147.1429 | 5 | 754.2017 | 150.8403 | 11.99421 | | |
| ANOVA | | | | | | |
| Source of Variation | SS | df | MS | F | P-value | F crit |
| Between Groups | 140.8321 | 2 | 70.41605 | 4.243753 | 0.040379 | 3.885294 |
| Within Groups | 199.1145 | 12 | 16.59287 | | | |
| Total | 339.9466 | 14 | | | | |

FIG. 23B

| ANOVA: Single Factor A, B, C - day 44 | | | | | | |
|---|---|---|---|---|---|---|
| SUMMARY | | | | | | |
| Groups | Count | Sum | Average | Variance | | |
| 182.8571 | 5 | 998.1614 | 199.6323 | 270.8914 | | |
| 183.8235 | 5 | 938.5714 | 187.7143 | 110.8163 | | |
| 180 | 5 | 937.9832 | 187.5966 | 40.31001 | | |
| ANOVA | | | | | | |
| Source of Variation | SS | df | MS | F | P-value | F crit |
| Between Groups | 478.1826 | 2 | 239.0913 | 1.69963 | 0.223918 | 3.885294 |
| Within Groups | 1688.071 | 12 | 140.6726 | | | |
| Total | 2166.254 | 14 | | | | |

FIG. 23C

ANOVA: Single Factor A, B, C - day 58

SUMMARY

| Groups | Count | Sum | Average | Variance |
|---|---|---|---|---|
| 238.5714 | 5 | 1232.121 | 246.4242 | 140.7747 |
| 238.2353 | 5 | 1190 | 238 | 13.87755 |
| 218.5714 | 5 | 1196.597 | 239.3193 | 83.75856 |

ANOVA

| Source of Variation | SS | df | MS | F | P-value | F crit |
|---|---|---|---|---|---|---|
| Between Groups | 205.3138 | 2 | 102.6569 | 1.291765 | 0.310393 | 3.885293835 |
| Within Groups | 953.6433 | 12 | 79.47028 | | | |
| Total | 1158.957 | 14 | | | | |

FIG. 23D

ANOVA: Single Factor A, B, C - day 72

SUMMARY

| Groups | Count | Sum | Average | Variance |
|---|---|---|---|---|
| 280 | 5 | 1449.585 | 289.917 | 201.0757 |
| 268.5714 | 5 | 1426.933 | 285.3866 | 49.63668 |
| 261.4286 | 5 | 1426.261 | 285.2521 | 105.3157 |

ANOVA

| Source of Variation | SS | df | MS | F | P-value | F crit |
|---|---|---|---|---|---|---|
| Between Groups | 70.5067 | 2 | 35.25335 | 0.297055 | 0.748311 | 3.885294 |
| Within Groups | 1424.112 | 12 | 118.676 | | | |
| Total | 1494.619 | 14 | | | | |

FIG. 23E

ANOVA: Single Factor A, B, C - day 86

SUMMARY

| Groups | Count | Sum | Average | Variance |
|---|---|---|---|---|
| Column 1 | 6 | 1998.333 | 333.0556 | 214.9074 |
| Column 2 | 6 | 1888.333 | 314.7222 | 46.01852 |
| Column 3 | 6 | 1925 | 320.8333 | 113.0556 |

ANOVA

| Source of Variation | SS | df | MS | F | P-value | F crit |
|---|---|---|---|---|---|---|
| Between Groups | 1045.679 | 2 | 522.8395 | 4.194107 | 0.035744 | 3.68232 |
| Within Groups | 1869.907 | 15 | 124.6605 | | | |
| Total | 2915.586 | 17 | | | | |

FIG. 23F

Anova: Single Factor A, B, C – day 100

SUMMARY

| Groups | Count | Sum | Average | Variance |
|---|---|---|---|---|
| Column 1 | 6 | 2331.034 | 388.5057 | 614.0864 |
| Column 2 | 6 | 2175.309 | 362.5515 | 225.6457 |
| Column 3 | 6 | 2157.95 | 359.6583 | 200.1136 |

ANOVA

| Source of Variation | SS | df | MS | F | P-value | F crit |
|---|---|---|---|---|---|---|
| Between Groups | 3028.344 | 2 | 1514.172 | 4.368451 | 0.031989 | 3.68232 |
| Within Groups | 5199.229 | 15 | 346.6152 | | | |
| Total | 8227.572 | 17 | | | | |

FIG. 23G

| ANOVA: Single Factor A, B, C - day 114 | | | | | | |
|---|---|---|---|---|---|---|
| SUMMARY | | | | | | |
| Groups | Count | Sum | Average | Variance | | |
| Column 1 | 6 | 2588.793 | 431.4655 | 409.7064 | | |
| Column 2 | 6 | 2389.199 | 398.1998 | 211.5964 | | |
| Column 3 | 6 | 2342.809 | 390.4681 | 136.6578 | | |
| | | | | | | |
| ANOVA | | | | | | |
| Source of Variation | SS | df | MS | F | P-value | F crit |
| Between Groups | 5694.345 | 2 | 2847.172 | 11.26908 | 0.001028 | 3.68232 |
| Within Groups | 3789.803 | 15 | 252.6535 | | | |
| Total | 9484.147 | 17 | | | | |

FIG. 23H

| ANOVA: Single Factor A, B, C - day 135 | | | | | | |
|---|---|---|---|---|---|---|
| SUMMARY | | | | | | |
| Groups | Count | Sum | Average | Variance | | |
| Column 1 | 6 | 2899.516 | 483.2526 | 632.4091 | | |
| Column 2 | 6 | 2704.537 | 450.7561 | 291.9072 | | |
| Column 3 | 6 | 2669.303 | 444.8838 | 298.9867 | | |
| | | | | | | |
| ANOVA | | | | | | |
| Source of Variation | SS | df | MS | F | P-value | F crit |
| Between Groups | 5125.35 | 2 | 2562.675 | 6.284645 | 0.010411 | 3.68232 |
| Within Groups | 6116.515 | 15 | 407.7677 | | | |
| Total | 11241.86 | 17 | | | | |

FIG. 23I

| Treatment | Cage No | Food intake (gr) | Number of fish | Initial weight (gr) | Initial biomass (gr) | Final weight (gr) | Final biomass (gr) | Neto biomass (gr) | FCR |
|---|---|---|---|---|---|---|---|---|---|
| A | 1 | 25,131 | 35 | 95 | 3,325 | 490 | 17,150 | 13,825 | 1.82 |
| A | 2 | 24,098 | 35 | 95 | 3,325 | 471 | 16,500 | 13,175 | 1.83 |
| B | 3 | 24,183 | 35 | 95 | 3,325 | 458 | 16,042 | 12,717 | 1.90 |
| B | 4 | 24,144 | 35 | 95 | 3,325 | 471 | 16,474 | 13,149 | 1.84 |
| C | 5 | 22,899 | 35 | 95 | 3,325 | 434 | 15,188 | 11,863 | 1.93 |
| C | 6 | 24,341 | 35 | 95 | 3,325 | 458 | 16,042 | 12,717 | 1.91 |
| A | 7 | 25,483 | 35 | 95 | 3,325 | 488 | 17,092 | 13,767 | 1.85 |
| A | 8 | 25,771 | 35 | 95 | 3,325 | 503 | 17,617 | 14,292 | 1.80 |
| B | 9 | 24,520 | 35 | 95 | 3,325 | 488 | 17,092 | 13,767 | 1.78 |
| B | 10 | 23,797 | 35 | 95 | 3,325 | 425 | 14,875 | 11,550 | 2.06 |
| C | 11 | 24,410 | 35 | 95 | 3,325 | 469 | 16,427 | 13,102 | 1.86 |
| C | 12 | 23,996 | 35 | 95 | 3,325 | 452 | 15,810 | 12,485 | 1.92 |
| A | 13 | 26,162 | 35 | 95 | 3,325 | 538 | 18,828 | 15,503 | 1.69 |
| A | 14 | 25,256 | 35 | 95 | 3,325 | 520 | 18,200 | 14,875 | 1.70 |
| B | 15 | 23,913 | 35 | 95 | 3,325 | 442 | 15,458 | 12,133 | 1.97 |
| B | 16 | 25,304 | 35 | 95 | 3,325 | 481 | 16,835 | 13,510 | 1.87 |
| C | 17 | 24,137 | 35 | 95 | 3,325 | 450 | 15,750 | 12,425 | 1.94 |
| C | 18 | 24,826 | 35 | 95 | 3,325 | 477 | 16,683 | 13,358 | 1.86 |

FIG. 24

| Day | Date | A<br>A - 100 mg/Kg | B<br>B - 200 mg/Kg | C<br>C - Control |
|---|---|---|---|---|
| 0 | 04-12-14 | 160 | 160 | 160 |
| 14 | 18-12-14 | 182 | 184 | 184 |
| 27 | 31-12-14 | 206 | 204 | 207 |
| 41 | 14-01-15 | 239 | 232 | 231 |
| 55 | 28-01-15 | 282 | 275 | 274 |
| 69 | 11-02-15 | 333 | 318 | 314 |
| 83 | 25-02-15 | 383 | 363 | 358 |

FIG. 27

ANOVA: Single Factor A, C

SUMMARY

| Groups | Count | Sum | Average | Variance |
|---|---|---|---|---|
| Column 1 | 6 | 2299 | 383.1667 | 112.1667 |
| Column 2 | 6 | 2148 | 358 | 390.4 |

ANOVA

| Source of Variation | SS | df | MS | F | P-value | F crit |
|---|---|---|---|---|---|---|
| Between Groups | 1900.083 | 1 | 1900.083 | 7.561518 | 0.020485 | 4.964603 |
| Within Groups | 2512.833 | 10 | 251.2833 | | | |
| Total | 4412.917 | 11 | | | | |

FIG. 28

| FCR by treatments by cages | | |
|---|---|---|
| A | B | C |
| 2.1 | 2.4 | 2.6 |
| 2.4 | 2.4 | 2.5 |
| 2.3 | 3.1 | 2.5 |
| 2.3 | 2.7 | 3.1 |
| 2.4 | 2.4 | 2.4 |
| 2.2 | 2.2 | 2.4 |

| Average | 2.29 | 2.53 | 2.58 |
|---|---|---|---|

FIG. 29

ANOVA Single Factor A, B, C

SUMMARY

| Groups | Count | Sum | Average | Variance |
|---|---|---|---|---|
| Column 1 | 6 | 13.76166 | 2.293609 | 0.009306 |
| Column 2 | 6 | 15.19569 | 2.532616 | 0.089552 |
| Column 3 | 6 | 15.50915 | 2.584859 | 0.072338 |

ANOVA

| Source of Variation | SS | df | MS | F | P-value | F crit |
|---|---|---|---|---|---|---|
| Between Groups | 0.289359 | 2 | 0.14468 | 2.535337 | 0.112582 | 3.68232 |
| Within Groups | 0.855978 | 15 | 0.057065 | | | |
| Total | 1.145337 | 17 | | | | |

FIG. 30

| Date | Day | pH | Nitrite (ppm) | Ammonia (ppm) | Oxygen (ppm) | Temp (Co) | Total salinity (ppm) |
|---|---|---|---|---|---|---|---|
| 04-12-14 | 0 | 7.7 | 0.8 | 0.1 | 6.6 | 19.5 | 2,300 |
| 09-12-14 | 5 | 7.7 | 0.8 | 0.1 | 6.4 | 21.0 | 2,300 |
| 14-12-14 | 10 | 7.7 | 0.8 | 0.1 | 6.5 | 21.0 | 2,300 |
| 19-12-14 | 15 | 7.7 | 0.8 | 0.1 | 6.4 | 20.0 | 2,300 |
| 24-12-14 | 20 | 7.7 | 0.9 | 0.1 | 6.6 | 21.0 | 2,300 |
| 29-12-14 | 25 | 7.6 | 0.9 | 0.2 | 7.0 | 20.8 | 2,300 |
| 03-01-15 | 30 | 7.6 | 0.9 | 0.2 | 6.7 | 20.2 | 2,300 |
| 08-01-15 | 35 | 7.8 | 0.9 | 0.2 | 8.0 | 18.5 | 2,300 |
| 13-01-15 | 40 | 7.8 | 0.9 | 0.3 | 7.6 | 16.2 | 2,300 |
| 18-01-15 | 45 | 7.8 | 0.8 | 0.3 | 7.7 | 17.4 | 2,300 |
| 23-01-15 | 50 | 7.9 | 0.8 | 0.3 | 6.8 | 19.5 | 2,300 |
| 28-01-15 | 55 | 7.6 | 0.8 | 0.4 | 7.1 | 20.3 | 2,300 |
| 02-02-15 | 60 | 7.6 | 0.8 | 0.4 | 5.5 | 20.1 | 2,300 |
| 07-02-15 | 65 | 7.7 | 0.9 | 0.4 | 6.2 | 20.2 | 2,300 |
| 12-02-15 | 70 | 7.7 | 0.9 | 0.5 | 7.4 | 19.4 | 2,300 |
| 17-02-15 | 75 | 7.7 | 1.0 | 0.6 | 6.9 | 18.5 | 2,300 |
| 22-02-15 | 80 | 7.7 | 1.0 | 0.6 | 6.5 | 17.7 | 2,300 |

FIG. 31

| Feeding rate (%) for Carp by temperature | | | |
|---|---|---|---|
| Fish weight (gr) | 20°C | 25°C | 30°C |
| 1-10 | 10.5 | 15.0 | 19.5 |
| 10-20 | 7.0 | 10.0 | 13.0 |
| 20-30 | 6.3 | 9.0 | 11.7 |
| 30-40 | 5.6 | 8.0 | 10.4 |
| 40-50 | 5.3 | 7.5 | 9.8 |
| 50-60 | 4.9 | 7.0 | 9.1 |
| 60-70 | 4.9 | 7.0 | 9.1 |
| 70-80 | 4.6 | 6.5 | 8.5 |
| 80-90 | 4.4 | 6.3 | 8.2 |
| 90-100 | 4.2 | 6.0 | 7.8 |
| 100-150 | 4.2 | 6.0 | 7.8 |
| 150-200 | 3.9 | 5.5 | 7.2 |
| 200-250 | 3.5 | 5.0 | 6.5 |
| 250-300 | 3.4 | 4.8 | 6.2 |
| 300-350 | 3.2 | 4.5 | 5.9 |
| 350-400 | 3.0 | 4.3 | 5.6 |
| 400-450 | 2.8 | 4.0 | 5.2 |
| 450-500 | 2.7 | 3.8 | 4.9 |
| 500-600 | 2.3 | 3.3 | 4.3 |
| 600-700 | 2.1 | 3.0 | 3.9 |
| 700-800 | 2.0 | 2.8 | 3.6 |
| 800-900 | 1.8 | 2.6 | 3.4 |
| 900-1,000 | 1.7 | 2.4 | 3.1 |
| 1,000-1,100 | 1.5 | 2.2 | 2.9 |
| 1,100-1,200 | 1.4 | 2.0 | 2.6 |

FIG. 33

| Day | Cage | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| | Treatment | A | A | C | C | B | B | A | A | C | C | B | B | A | A | C | C | B | B |
| 0 | 04-12-14 | 160 | 160 | 160 | 160 | 160 | 160 | 160 | 160 | 160 | 160 | 160 | 160 | 160 | 160 | 160 | 160 | 160 | 160 |
| 14 | 18-12-14 | 185 | 181 | 192 | 188 | 192 | 184 | 181 | 187 | 182 | 181 | 181 | 181 | 180 | 181 | 181 | 180 | 182 | 181 |
| 27 | 31-12-14 | 208 | 205 | 210 | 211 | 219 | 199 | 201 | 213 | 209 | 198 | 197 | 199 | 201 | 210 | 206 | 207 | 208 | 209 |
| 41 | 14-01-15 | 245 | 236 | 234 | 236 | 245 | 233 | 232 | 245 | 230 | 225 | 221 | 228 | 231 | 243 | 229 | 231 | 231 | 236 |
| 55 | 28-01-15 | 282 | 266 | 270 | 279 | 283 | 279 | 281 | 287 | 270 | 255 | 247 | 267 | 284 | 294 | 286 | 281 | 289 | 286 |
| 69 | 11-02-15 | 345 | 320 | 313 | 319 | 329 | 327 | 329 | 325 | 313 | 285 | 289 | 307 | 327 | 349 | 321 | 335 | 321 | 333 |
| 83 | 25-02-15 | 399 | 371 | 354 | 367 | 370 | 369 | 379 | 380 | 360 | 321 | 324 | 350 | 377 | 393 | 369 | 377 | 369 | 394 |

FIG. 34

ANOVA: Single Factor A, B, C - day 14

SUMMARY

| Groups | Count | Sum | Average | Variance |
|---|---|---|---|---|
| Column 1 | 6 | 1093 | 182.1667 | 6.566667 |
| Column 2 | 6 | 1104 | 184 | 23.6 |
| Column 3 | 6 | 1101 | 183.5 | 18.7 |

ANOVA

| Source of Variation | SS | df | MS | F | P-value | F crit |
|---|---|---|---|---|---|---|
| Between Groups | 10.77778 | 2 | 5.388889 | 0.330832 | 0.723436 | 3.68232 |
| Within Groups | 244.3333 | 15 | 16.28889 | | | |
| Total | 255.1111 | 17 | | | | |

FIG. 35A

ANOVA: Single Factor A, B, C - day 27

SUMMARY

| Groups | Count | Sum | Average | Variance |
|---|---|---|---|---|
| Column 1 | 6 | 1238 | 206.3333 | 23.86667 |
| Column 2 | 6 | 1241 | 206.8333 | 22.16667 |
| Column 3 | 6 | 1223 | 203.8333 | 72.96667 |

ANOVA

| Source of Variation | SS | df | MS | F | P-value | F crit |
|---|---|---|---|---|---|---|
| Between Groups | 31 | 2 | 15.5 | 0.390756 | 0.683234 | 3.68232 |
| Within Groups | 595 | 15 | 39.66667 | | | |
| Total | 626 | 17 | | | | |

FIG. 35B

ANOVA: Single Factor A, B, C - day 41

SUMMARY

| Groups | Count | Sum | Average | Variance |
|---|---|---|---|---|
| Column 1 | 6 | 1432 | 238.6667 | 41.86667 |
| Column 2 | 6 | 1385 | 230.8333 | 14.96667 |
| Column 3 | 6 | 1394 | 232.3333 | 64.66667 |

ANOVA

| Source of Variation | SS | df | MS | F | P-value | F crit |
|---|---|---|---|---|---|---|
| Between Groups | 207.4444 | 2 | 103.7222 | 2.561043 | 0.110443 | 3.68232 |
| Within Groups | 607.5 | 15 | 40.5 | | | |
| Total | 814.9444 | 17 | | | | |

FIG. 35C

ANOVA: Single Factor A, B, C - day 55

SUMMARY

| Groups | Count | Sum | Average | Variance |
|---|---|---|---|---|
| Column 1 | 6 | 1694 | 282.3333 | 85.86667 |
| Column 2 | 6 | 1641 | 273.5 | 121.9 |
| Column 3 | 6 | 1651 | 275.1667 | 248.9667 |

ANOVA

| Source of Variation | SS | df | MS | F | P-value | F crit |
|---|---|---|---|---|---|---|
| Between Groups | 264.3333 | 2 | 132.1667 | 0.868121 | 0.439794 | 3.682320344 |
| Within Groups | 2283.667 | 15 | 152.2444 | | | |
| Total | 2548 | 17 | | | | |

FIG. 35D

ANOVA: Single Factor A, B, C - day 69

SUMMARY

| Groups | Count | Sum | Average | Variance |
|---|---|---|---|---|
| Column 1 | 6 | 1995 | 332.5 | 136.7 |
| Column 2 | 6 | 1886 | 314.3333 | 271.4667 |
| Column 3 | 6 | 1906 | 317.6667 | 279.4667 |

ANOVA

| Source of Variation | SS | df | MS | F | P-value | F crit |
|---|---|---|---|---|---|---|
| Between Groups | 1122.333 | 2 | 561.1667 | 2.448252 | 0.120187 | 3.68232 |
| Within Groups | 3438.167 | 15 | 229.2111 | | | |
| Total | 4560.5 | 17 | | | | |

FIG. 35E

| Treatment | Cage No | Food intake (gr) | Number of fish | Initial weight (gr) | Initial biomass (gr) | Final weight (gr) | Final biomass (gr) | Net biomass (gr) | FCR |
|---|---|---|---|---|---|---|---|---|---|
| A | 1 | 17,952 | 35 | 160 | 5,600 | 399 | 13,965 | 8,365 | 2.15 |
| A | 2 | 17,808 | 35 | 160 | 5,600 | 371 | 12,985 | 7,385 | 2.41 |
| C | 3 | 17,744 | 35 | 160 | 5,600 | 354 | 12,390 | 6,790 | 2.61 |
| C | 4 | 17,800 | 35 | 160 | 5,600 | 367 | 12,845 | 7,245 | 2.46 |
| B | 5 | 17,888 | 35 | 160 | 5,600 | 370 | 12,950 | 7,350 | 2.43 |
| B | 6 | 17,872 | 35 | 160 | 5,600 | 369 | 12,915 | 7,315 | 2.44 |
| A | 7 | 17,760 | 35 | 160 | 5,600 | 379 | 13,265 | 7,665 | 2.32 |
| A | 8 | 17,856 | 35 | 160 | 5,600 | 380 | 13,300 | 7,700 | 2.32 |
| C | 9 | 17,752 | 35 | 160 | 5,600 | 360 | 12,600 | 7,000 | 2.54 |
| C | 10 | 17,496 | 35 | 160 | 5,600 | 321 | 11,235 | 5,635 | 3.10 |
| B | 11 | 17,528 | 35 | 160 | 5,600 | 324 | 11,340 | 5,740 | 3.05 |
| B | 12 | 17,696 | 35 | 160 | 5,600 | 350 | 12,250 | 6,650 | 2.66 |
| A | 13 | 17,872 | 35 | 160 | 5,600 | 377 | 13,195 | 7,595 | 2.35 |
| A | 14 | 18,064 | 35 | 160 | 5,600 | 393 | 13,755 | 8,155 | 2.22 |
| C | 15 | 17,816 | 35 | 160 | 5,600 | 369 | 12,915 | 7,315 | 2.44 |
| C | 16 | 17,944 | 35 | 160 | 5,600 | 377 | 13,195 | 7,595 | 2.36 |
| B | 17 | 17,816 | 35 | 160 | 5,600 | 369 | 12,915 | 7,315 | 2.44 |
| B | 18 | 17,760 | 35 | 160 | 5,600 | 394 | 13,790 | 8,190 | 2.17 |

FIG. 36

| ANOVA: Single Factor | | | | | | |
|---|---|---|---|---|---|---|
| SUMMARY | | | | | | |
| Groups | Count | Sum | Average | Variance | | |
| Column 1 | 6 | 4.1 | 0.683333 | 0.017667 | | |
| Column 2 | 6 | 5.6 | 0.933333 | 0.014667 | | |
| | | | | | | |
| ANOVA | | | | | | |
| Source of Variation | SS | df | MS | F | P-value | F crit |
| Between Groups | 0.1875 | 1 | 0.1875 | 11.59794 | 0.006708 | 4.964603 |
| Within Groups | 0.161667 | 10 | 0.016167 | | | |
| | | | | | | |
| Total | 0.349167 | 11 | | | | |

FIG. 41

| Day | Date | Ammonia (ppm) | Nitrite (ppm) | pH | Oxygen (ppm) | Temp (C°) | Turbidity (1-5) | NH₄Cl (gr/tank) |
|---|---|---|---|---|---|---|---|---|
| 29 | 26-12-14 | 0.2 | 0.1 | 8.4 | 6.6 | 18.0 | 1.0 | |
| 30 | 27-12-14 | 0.2 | 0.0 | 0.0 | 6.4 | 16.7 | 1.0 | |
| 31 | 28-12-14 | 0.2 | 0.0 | 8.4 | 6.7 | 17.5 | 1.0 | |
| 32 | 29-12-14 | 0.2 | 0.1 | 0.0 | 0.0 | 17.0 | 1.0 | |
| 33 | 30-12-14 | 0.0 | 0.0 | 8.3 | 7.0 | 16.0 | 1.0 | |
| 34 | 31-12-14 | 0.0 | 0.0 | 8.5 | 6.7 | 17.0 | 1.0 | |
| 35 | 01-01-15 | 0.3 | 0.3 | 8.3 | 6.4 | 18.0 | 1.0 | |
| 36 | 02-01-15 | 0.0 | 0.2 | 8.4 | 0.0 | 18.0 | 1.0 | |
| 37 | 03-01-15 | 0.2 | 0.0 | 0.0 | 6.7 | 18.1 | 1.0 | |
| 38 | 04-01-15 | 0.0 | 0.0 | 8.4 | 8.4 | 16.8 | 1.0 | |
| 39 | 05-01-15 | 0.3 | 0.3 | 8.3 | 7.0 | 16.8 | 1.0 | |
| 40 | 06-01-15 | 0.0 | 0.0 | 0.0 | 6.7 | 16.7 | 1.0 | |
| 41 | 07-01-15 | 0.0 | 0.0 | 8.3 | 0.0 | 15.5 | 1.0 | |
| 42 | 08-01-15 | 0.3 | 0.2 | 8.4 | 7.0 | 14.3 | 1.0 | |
| 43 | 09-01-15 | 0.0 | 0.0 | 8.4 | 6.7 | 14.4 | 1.0 | |
| 44 | 10-01-15 | 0.0 | 0.0 | 0.0 | 6.4 | 13.0 | 1.0 | |
| 45 | 11-01-15 | 0.0 | 0.0 | 8.3 | 7.0 | 12.5 | 1.0 | |
| 46 | 12-01-15 | 0.2 | 0.0 | 8.5 | 0.0 | 12.5 | 1.0 | |
| 47 | 13-01-15 | 0.3 | 0.3 | 0.0 | 6.4 | 12.6 | 1.0 | |
| 48 | 14-01-15 | 0.0 | 0.0 | 8.3 | 7.7 | 13.0 | 1.0 | |
| 49 | 15-01-15 | 0.4 | 1.0 | 8.5 | 7.6 | 14.3 | 1.0 | |
| 50 | 16-01-15 | 0.0 | 0.8 | 8.4 | 0.0 | 13.7 | 1.0 | |
| 51 | 17-01-15 | 0.4 | 0.7 | 8.4 | 7.7 | 13.5 | 2.0 | |
| 52 | 18-01-15 | 0.4 | 0.6 | 0.0 | 7.6 | 13.1 | 2.0 | |
| 53 | 19-01-15 | 0.0 | 0.0 | 8.3 | 0.0 | 14.0 | 2.0 | |
| 54 | 20-01-15 | 0.5 | 0.8 | 8.5 | 6.8 | 15.2 | 2.0 | |
| 55 | 21-01-15 | 0.5 | 1.0 | 0.0 | 7.0 | 15.5 | 2.0 | |
| 56 | 22-01-15 | 0.6 | 0.0 | 8.5 | 0.0 | 16.5 | 2.0 | |
| 57 | 23-01-15 | 0.5 | 0.8 | 8.5 | 7.6 | 16.9 | 2.0 | |
| 58 | 24-01-15 | 0.0 | 0.7 | 0.0 | 8.0 | 17.5 | 2.0 | |
| 59 | 25-01-15 | 0.6 | 0.8 | 8.5 | 7.6 | 18.0 | 3.0 | |
| 60 | 26-01-15 | 0.6 | 0.8 | 0.0 | 7.0 | 18.0 | 3.0 | |
| | | | | | | | | |
| 62 | 28-01-15 | 0.5 | 0.9 | 8.4 | 7.0 | 17.8 | 3.0 | 2 |
| 63 | 29-01-15 | 1.7 | 2.2 | 8.3 | 7.9 | 17.6 | 3.0 | 3 |
| 64 | 30-01-15 | 1.5 | 3.6 | 8.1 | 0.0 | 17.6 | 3.0 | |
| 65 | 31-01-15 | 1.0 | 3.9 | 0.0 | 0.0 | 17.3 | 4.0 | |
| 66 | 01-02-15 | 0.8 | 4.2 | 8.1 | 8.4 | 16.9 | 4.0 | 3 |
| 67 | 02-02-15 | 3.0 | 3.5 | 0.0 | 8.0 | 17.3 | 5.0 | 5 |
| 68 | 03-02-15 | 2.2 | 3.6 | 7.7 | 7.0 | 17.8 | 4.0 | 3 |
| 69 | 04-02-15 | 2.8 | 4.2 | 7.5 | 0.0 | 18.1 | 5.0 | 4 |
| 70 | 05-02-15 | 5.5 | 5.5 | 7.4 | 6.4 | 17.9 | 5.0 | 4 |
| 71 | 06-02-15 | 9.6 | 2.5 | 7.2 | 6.4 | 18.1 | 5.0 | 5 |
| 72 | 07-02-15 | 9.0 | 2.3 | 0.0 | 7.2 | 18.5 | 4.0 | |
| 73 | 08-02-15 | 8.3 | 2.1 | 7.0 | 0.0 | 19.5 | 5.0 | 5 |
| 74 | 09-02-15 | 9.5 | 2.8 | 6.9 | 0.0 | 18.8 | 5.0 | 7 |

FIG. 42

| pH | Temperature | | | | | | | | | | | | |
|---|---|---|---|---|---|---|---|---|---|---|---|---|---|
| | 42.8 (°F) | 46.4 | 50.0 | 53.6 | 57.2 | 60.8 | 64.4 | 68.0 | 71.6 | 75.2 | 78.8 | 82.4 | 86.0 | 89.6 |
| | 6 (°C) | 8 | 10 | 12 | 14 | 16 | 18 | 20 | 22 | 24 | 26 | 28 | 30 | 32 |
| 7.0 | .0013 | .0016 | .0019 | .0022 | .0025 | .0029 | .0034 | .0039 | .0045 | .0052 | .0060 | .0069 | .0080 | .0093 |
| 7.2 | .0021 | .0025 | .0029 | .0034 | .0040 | .0046 | .0054 | .0062 | .0072 | .0083 | .0096 | .0110 | .0128 | .0150 |
| 7.4 | .0034 | .0040 | .0046 | .0054 | .0063 | .0073 | .0085 | .0098 | .0114 | .0131 | .0152 | .0175 | .0198 | .0235 |
| 7.6 | .0053 | .0063 | .0073 | .0086 | .0100 | .0116 | .0134 | .0155 | .0179 | .0206 | .0236 | .0271 | .0310 | .0359 |
| 7.8 | .0084 | .0099 | .0116 | .0135 | .0157 | .0182 | .0211 | .0244 | .0281 | .0322 | .0370 | .0423 | .0482 | .0572 |
| 8.0 | .0133 | .0156 | .0182 | .0212 | .0247 | .0286 | .0330 | .0381 | .0438 | .0502 | .0574 | .0654 | .0743 | .0877 |
| 8.2 | .0210 | .0245 | .0286 | .0333 | .0385 | .0445 | .0514 | .0590 | .0676 | .0772 | .0880 | .0998 | .1129 | .1322 |
| 8.4 | .0328 | .0383 | .0445 | .0517 | .0597 | .0688 | .0790 | .0904 | .1031 | .1171 | .1328 | .1495 | .1678 | .1948 |
| 8.6 | .0510 | .0593 | .0688 | .0795 | .0914 | .1048 | .1197 | .1361 | .1541 | .1737 | .1959 | .2178 | .2422 | .2768 |
| 8.8 | .0785 | .0909 | .1048 | .1204 | .1378 | .1566 | .1773 | .1998 | .2241 | .2500 | .2774 | .3063 | .3362 | .3776 |
| 9.0 | .1190 | .1368 | .1565 | .1782 | .2018 | .2273 | .2546 | .2836 | .3140 | .3456 | .3783 | .4116 | .4453 | .4902 |
| 9.2 | .1763 | .2008 | .2273 | .2558 | .2861 | .3180 | .3512 | .3856 | .4204 | .4557 | .4909 | .5258 | .5599 | .6038 |
| 9.4 | .2533 | .2847 | .3180 | .3536 | .3884 | .4249 | .4618 | .4985 | .5348 | .5702 | .6045 | .6373 | .6685 | .7072 |
| 9.6 | .3498 | .3868 | .4249 | .4633 | .5018 | .5394 | .5762 | .6117 | .6456 | .6777 | .7078 | .7358 | .7617 | .7929 |
| 9.8 | .4600 | .5000 | .5394 | .5778 | .6147 | .6499 | .6831 | .7140 | .7428 | .7692 | .7933 | .8153 | .8351 | .8585 |
| 10.0 | .5745 | .6131 | .6498 | .6844 | .7168 | .7469 | .7735 | .7983 | .8207 | .8408 | .8588 | .8749 | .8892 | .9058 |
| 10.2 | .6815 | .7152 | .7463 | .7746 | .8003 | .8234 | .8441 | .8625 | .8788 | .8933 | .9060 | .9173 | .9271 | .9389 |

Concentration of unionized ammonia at various concentration of total ammonia and pH

| pH | \multicolumn{10}{c}{TOTAL AMMONIA CONCENTRATION (ppm $NH_3$, N)} | |
|---|---|---|---|---|---|---|---|---|---|---|---|
|    | 1.0 | 2.0 | 3.0 | 4.0 | 5.0 | 6.0 | 7.0 | 8.0 | 9.0 | 10.0 | |
| 6.0 | .001 | .001 | .002 | .002 | .003 | .003 | .004 | .005 | .005 | .006 | |
| 6.2 | .001 | .002 | .003 | .004 | .005 | .005 | .006 | .007 | .008 | .009 | *A |
| 6.4 | .002 | .003 | .004 | .006 | .007 | .009 | .010 | .011 | .012 | .014 | |
| 6.6 | .002 | .005 | .007 | .009 | .011 | .014 | .016 | .018 | .020 | .022 | |
| 6.8 | .004 | .007 | .011 | .014 | .018 | .021 | .025 | .028 | .032 | .035 | |
| 7.0 | .006 | .011 | .017 | .022 | .028 | .034 | .039 | .046 | .050 | .056 | *B |
| 7.2 | .009 | .018 | .027 | .036 | .044 | .053 | .062 | .071 | .080 | .088 | |
| 7.4 | .014 | .028 | .042 | .056 | .070 | .084 | .098 | .112 | .125 | .139 | |
| 7.6 | .022 | .044 | .066 | .088 | .110 | .131 | .153 | .175 | .197 | .219 | *C |
| 7.8 | .034 | .069 | .103 | .137 | .171 | .205 | .240 | .274 | .308 | .343 | |
| 8.0 | .053 | .107 | .160 | .213 | .266 | .320 | .373 | .426 | .479 | .533 | |
| 8.2 | .082 | .164 | .246 | .327 | .409 | .491 | .573 | .655 | .737 | .818 | |
| 8.4 | .124 | .248 | .371 | .495 | .619 | .743 | .866 | .990 | 1.114 | 1.238 | |
| 8.6 | .183 | .366 | .549 | .732 | .915 | 1.098 | 1.281 | 1.463 | 1.646 | 1.829 | *D |
| 8.8 | .262 | .524 | .786 | 1.048 | 1.310 | 1.571 | 1.833 | 2.095 | 2.357 | 2.619 | |
| 9.0 | .360 | .720 | 1.08 | 1.44 | 1.80 | 2.160 | 2.52 | 2.88 | 3.24 | 3.599 | |

*A = SAFE    *B = STRESS    *C = SLOW DEATH    *D = RAPID DEATH

FIG. 47

| Daily mortality after stress | | | |
|---|---|---|---|
| Day | Date | Control | 100 mg/Kg BW/d |
| 30 | 25-01-15 | 0 | 0 |
| 31 | 26-01-15 | 0 | 0 |
| 32 | 27-01-15 | 0 | 0 |
| 33 | 28-01-15 | 0 | 0 |
| 34 | 29-01-15 | 0 | 0 |
| 35 | 30-01-15 | 0 | 0 |
| 36 | 31-01-15 | 0 | 0 |
| 37 | 01-02-15 | 0 | 1 |
| 38 | 02-02-15 | 0 | 0 |
| 39 | 03-02-15 | 6 | 0 |
| 40 | 04-02-15 | 5 | 1 |
| 41 | 05-02-15 | 0 | 0 |
| 42 | 06-02-15 | 0 | 0 |
| 43 | 07-02-15 | 3 | 2 |
| 44 | 08-02-15 | 5 | 0 |
| Total | | 19 | 4 |

| PAQ-Grow™ 100 mg/Kg BW/d | PAQ-Grow™ 200 mg/Kg BW/d | Control |
|---|---|---|
| 72% | 74% | 60% |

FIG. 51

| Parameter | Results |
|---|---|
| Temperature | 26-32°C |
| Total salinity | 10.0-10.2 ppt |
| Ammonia | 0.2-1.0 ppm |
| Nitrite | 0.2-1.0 ppm |
| pH | 8.1-8.3 |
| Oxygen | 6.0-7.0 ppm |

FIG. 52

COMPOSITION AND/OR COMBINATION FOR AQUACULTURE

CROSS REFERENCE TO RELATED APPLICATIONS

This is a continuation application of U.S. application Ser. No. 15/914,543, filed on Mar. 7, 2018, which is a U.S. continuation-in-part of International Application No. PCT/US2016/051080, filed on Sep. 9, 2016, which was published in English under PCT Article 21(2), which in turn claims the benefit of the earlier filing dates of U.S. provisional patent applications Nos. 62/216,153 and 62/216,162, both filed on Sep. 9, 2015, each of which are incorporated herein by reference in their entirety.

FIELD

The present disclosure concerns embodiments of a composition and/or combination for use alone or in combination with a feedstuff, and a method for administering such embodiments to aquatic animals for aquaculture.

BACKGROUND

Aquaculture is the process of raising aquatic animals, such as fish, crustaceans, and mollusks, typically but not necessarily as feed animals for human consumption. Aquaculture involves feeding the animals, protecting them from predators and illnesses, and generally raising the animals in order to enhance their production and growth. In order for aquaculture to be profitable, it must be a more efficient way of procuring aquatic animals than harvesting wild aquatic animals.

In aquaculture, feed conversion ratios are used to provide animal producers with a method for monitoring the efficiency of raising animals. The ability to estimate the amount of feed required per unit of body gain for animals allows animal producers to effectively budget costs associated with raising animals, such as feed shortfalls or waste, which can facilitate determining profit margins. Lowering the feed conversion ratio, meaning less food is required per unit of body gain, is an effective way to reduce aquaculture costs. In 1980, a report by Robert Smith for the United States Fish and Wildlife Service provided results from trials concerned with "the effect of several types of clay on growth rate, feed conversion efficiency and mortality of rainbow trout. Smith R. R., *Recent advances in nutrition: clay in trout diets*; Salmonid, 1980, vol. 4(4), 16-18. The report states that the "inclusion of some types of clay at about 10% of the diet can significantly reduce feed/grain ratios and increase rate of gain." The clays that resulted in these benefits were a sodium bentonite clay and a "clay supplied by 'Ion-Min'." Ion-Minim is a brand name for montmorillonite clay products from California Earth minerals.

Fish disease is a substantial source of monetary loss to aquaculturists. Production costs are increased by fish disease outbreaks because of the investment lost in dead fish, treatment costs, and decreased growth during convalescence. In nature diseased fish are quickly removed from the population by predators. In addition, fish are much less crowded in natural systems than in captivity. Parasites and bacteria may be of minimal significance under natural conditions, but can be substantially problematic when animals are crowded and stressed under culture conditions.

Disease is rarely a simple association between a pathogen and a host fish. Usually other circumstances must be present for active disease to develop in a population. These circumstances are generally circumstances that cause the aquatic animal "stress."

There are two broad categories of disease that affect fish, infectious and non-infectious diseases. Infectious diseases are caused by pathogenic organisms present in the environment or carried by other fish. They are contagious, and some type of treatment may be necessary to control the disease outbreak. In contrast, non-infectious diseases typically are caused by environmental issues, nutritional deficiencies, or genetic anomalies; they are not contagious and usually cannot be cured by medications.

Infectious diseases are broadly categorized as parasitic, bacterial, viral, or fungal diseases. Parasitic fish diseases are most frequently caused by small microscopic organisms called protozoa which live in the aquatic environment. There are a variety of protozoans that infest the gills and skin of fish causing irritation, weight loss, and eventually death. Most protozoan infections are relatively easy to control using standard fishery chemicals such as copper sulfate, formalin, or potassium permanganate.

Bacterial diseases are often internal infections and require treatment with medicated feeds containing antibiotics. Typically, fish infected with a bacterial disease will have hemorrhagic spots or ulcers along the body wall and around the eyes and mouth. They may also have an enlarged, fluid-filled abdomen, and protruding eyes. Bacterial diseases can also be external, resulting in erosion of skin and ulceration. *Columnaris* is an example of an external bacterial infection which may be caused by rough handling.

Viral diseases are impossible to distinguish from bacterial diseases without special laboratory tests. They are difficult to diagnose and there are no specific medications available to cure viral infections of fish.

Fungal diseases are the fourth type of infectious disease. Fungal spores are common in the aquatic environment, but are not normally a problem in healthy fish. When fish are infected with an external parasite, bacterial infection, or injured by handling, fungi can colonize diseased tissue on the exterior of the fish. These areas appear to have a cottony growth or may appear as brown matted areas when the fish are removed from the water.

Non-infectious diseases can be broadly categorized as environmental, nutritional, or genetic. Environmental diseases are the most important in commercial aquaculture. Environmental diseases include low dissolved oxygen, high ammonia, high nitrite or natural or man-made toxins in the aquatic environment. Ammonia toxicity is one factor associated with reduced health and loss of aquatic animals in aquaculture facilities. Fish and amphibians lack the mechanisms used by humans and other mammals to remove ammonia solutions from their bloodstream, as they can usually excrete it directly. For this reason, ammonia is toxic to aquatic animals. Excess ammonia can result in poor growth and feed conversion rates, reduced reproductive capability, and increased stress, making animals more susceptible to disease and infection. In fish, higher concentrations of ammonia can also damage gills and tissue, and ultimately result in death.

Nutritional diseases can be very difficult to diagnose. A classic example of a nutritional catfish disease is "broken back disease," caused by vitamin C deficiency. The lack of dietary vitamin C contributes to improper bone development, resulting in deformation of the spinal column. Another important nutritional disease of catfish is "no blood disease," which may be related to a folic acid deficiency. Affected fish become anemic and may die. The condition seems to disappear when the deficient feed is discarded and a new feed provided.

Coccidiosis is a parasitic disease of the intestinal tract of animals caused by coccidian protozoa of the genus *Eimeria*. The disease can spread amongst animals by contact with infected feces by means of an infective form called the oocyst. Coccidiosis is a significant disease of certain animals, as it can affect animals at a very young age. It can be fatal or compromise animal health, thereby impairing the feed conversion rate of the animals. Thus, production, reproductive efficiency and animal health are adversely affected by coccidiosis. Diseases, such as coccidiosis, cause significant economic losses in certain animal industries. Such diseases also can negatively affect the health of domesticated animals.

SUMMARY

Disclosed embodiments concern a composition and/or combination comprising glucan, silica, mineral clay, mannans, polyphenol, *yucca, quillaja*, a probiotic, a combination thereof, or various combinations thereof that can be administered separately, but potentially within overlapping therapeutic effective periods, and a method of administering the same to an aquatic animal. The composition and/or combination may be formulated for use in aquaculture, such as a formulation that is suitable to be ingested and/or eaten when administered to an aquatic species. The composition and/or combination may further comprise an antimicrobial, a vaccine, or a combination thereof. The antimicrobial may be an antibiotic, an antifungal, an antiparasitic, an antiviral, or a combination thereof. In some embodiments, the antiparasitic is an anticoccidal, such as Salinomycin, and/or the antibiotic is virginiamycin. The composition and/or combination may also comprise endoglucanohydrolase. In some embodiments, the composition and/or combination comprises between 15% and 40% silica, between 50% and 81% mineral clay, between 1.0% and 5.0% β-glucans, and between 1% and 8.0% mannans. In a particular embodiment, the composition and/or combination consists essentially of β-glucans, β-1,3 (4)-endoglucanohydrolase, diatomaceous earth, a mineral clay, and glucomannan. In any embodiment, the compositions and/or combinations can also include an adhesive agent selected particularly to facilitate administration to aquatic species. In certain embodiments the adhesive agent comprises an oil, such as soy oil, or a syrup, such as molasses.

The composition and/or combination may further comprise a feedstuff. The feedstuff may be a feed ration, a mineral supplement, a protein supplement, a premix, molasses, a liquid feed, water, or any combination thereof. The composition and/or combination is formulated as a powder, a granule, a pellet, a solution, a suspension, or a combination thereof. In some embodiments, the composition and/or combination is formulated as a solid material having a particle size of from greater than zero to 4 mm or more, such as from greater than zero to 1 mm, from 1 mm to 2 mm or from 2 mm to 3 mm or more.

The composition and/or combination may be a composition. In other embodiments, the composition and/or combination is a combination comprising two or more components formulated for substantially simultaneous administration, or alternatively, formulated for sequential administration in any order. In still further embodiments, the combination comprises a single component administered multiple times with at least two administrations overlapping in an effective time period, and the single component may be formulated differently for administration at two different times.

In some embodiments, the aquatic animals can be animals raised for human consumption. In other embodiments the aquatic animals can be ornamental animals. Exemplary aquatic animals include fish (for example tilapia, carp, sea bream, or salmon), crustaceans (for example crabs, lobsters, or shrimp), and mollusks (for example octopus, oysters, or clams). The disclosed composition and/or combination may be administered to promote growth, to reduce its feed conversion ratio, to ameliorate at least one deleterious symptom or sign, to prevent or delay the onset of at least one deleterious symptom or sign, when the animal is exposed to a stressor, or will be exposed to a stressor, such as to ameliorate the effect of the stressor, or a combination thereof. In some embodiments, the composition and/or combination is administered to treat or prevent ammonia toxicity.

In any or all of the above embodiments, an effective amount of the composition and/or combination is administered to the aquatic species. In certain embodiments, the effective amount ranges from about 1 mg/kg body weight per day to about 20 g/kg body weight per day. In any or all of the above embodiments, the composition and/or combination may be administered by mixing the composition and/or combination with the animal's feed in an amount ranging from about 0.1 to about 20 kg per ton of feed and providing the composition and/or combination mixed with the feed to the animal. The composition and/or combination may be adhered to the feed, such as feed pellets, granules and/or powder, by an adhesive agent, and in some embodiments, the composition and/or combination may be top-coated onto the feed using the adhesive agent. In some embodiments, the composition and/or combination is formulated as a powder, a granule, a pellet, a solution, or a suspension.

The foregoing and other objects, features, and advantages of the invention will become more apparent from the following detailed description, which proceeds with reference to the accompanying figures.

BRIEF DESCRIPTION OF THE DRAWINGS

FIG. 1 is a table illustrating exemplary dose ranges of disclosed exemplary embodiments of the composition and/or combination for various growth stages.

FIG. 2 is a graph of the growth rate of sea bream using two different doses of exemplary embodiments of the composition and/or combination and a control group FIG. 3 is a table comparing the average weight (g) of sea bream being fed two different doses of exemplary embodiments of the composition and/or combination and a control group FIG. 4 is a table concerning a statistical analysis (ANOVA—single factor) of the average weight of sea bream after 158 days.

FIG. 5 is a table showing the feed conversion rate of sea bream in the trial at day 158.

FIG. 6 is a table showing the water quality data for the sea bream trial of FIG. 2.

FIG. 9 is a table of growth rate results by tank during the sea bream trial of FIG. 2.

FIGS. 10A-10J are tables concerning a statistical single-factor ANOVA analysis for trial groups A, B, and C for each date of measure.

FIG. 11 is a table of the feed conversion ratio (FCR) by tank by treatment.

FIGS. 12A and 12B are tables showing survival rate in the trial at day 128, and the mortality in each tank by date.

FIG. 15 is a table comparing the average weight (g) of hybrid tilapia being fed two different doses of the composition and/or combination and a control group.

FIG. 16 is a statistical single-factor ANOVA analysis of the average weight of the hybrid tilapia after 149 days.

FIG. 17 is a table of the food conversion ratio results for each group from the hybrid tilapia trial of FIG. 14.

FIG. 18 is a statistical, single-factor ANOVA analysis of the hybrid tilapia food conversion ratio of FIG. 17 after 149 days.

FIG. 19 is a table showing the water quality data collected during the hybrid tilapia trial of FIG. 14.

FIG. 21 is a table showing the expected growth rate and feeding chart of tilapia.

FIG. 22 is a table showing the results of growth rate by cage and date during the hybrid tilapia trial of FIG. 14.

FIGS. 23A-23I are tables showing a statistical, single-factor ANOVA analysis for trial groups A, B, and C for hybrid tilapia for each date of measure during the hybrid tilapia trial of FIG. 14.

FIG. 24 is a table of the feed conversion rate values per cage and treatment for the hybrid tilapia trial of FIG. 14.

FIG. 27 is a table comparing the average weight (g) of common carp being fed two different doses of the composition and/or combination and a control group.

FIG. 28 is a statistical, single-factor ANOVA analysis of the average weight of the common carp during the common carp trial of FIG. 26 after 83 days.

FIG. 29 is a table of the food conversion ratio results for each group during the common carp trial of FIG. 26.

FIG. 30 is a statistical, single-factor ANOVA analysis of the food conversion ratio of the common carp during the common carp trial of FIG. 26 after 83 days.

FIG. 31 is a table providing the water quality data collected during the common carp trial of FIG. 26.

FIG. 33 is a table providing the feeding chart of carp by temperature during the common carp trial of FIG. 26.

FIG. 34 is a table providing the growth rate results by cage and date during the common carp trial of FIG. 26.

FIGS. 35A-35E are tables providing a statistical, single-factor ANOVA analysis for trial groups A, B, and C for common carp for each date of measure.

FIG. 36 is a table of the feed conversion rate values per cage and treatment for the common carp trial of FIG. 26.

FIG. 41 is a statistical, single-factor ANOVA analysis of tilapia mortalities during the tilapia trial of FIG. 38 after 74 days.

FIG. 42 is a table providing the water quality data for the tilapia trial of FIG. 38.

FIG. 47 is a table listing the concentration of unionized ammonia at various concentrations of total ammonia and pH.

FIG. 51 is a table comparing the average survival (percent from 4 replicates) of shrimp using 100 and 200 mg/kg bodyweight per day doses, with a control.

FIG. 52 is a table listing the water quality data from the experiment of FIG. 51.

DETAILED DESCRIPTION

I. Terms

Figures 7, 8:
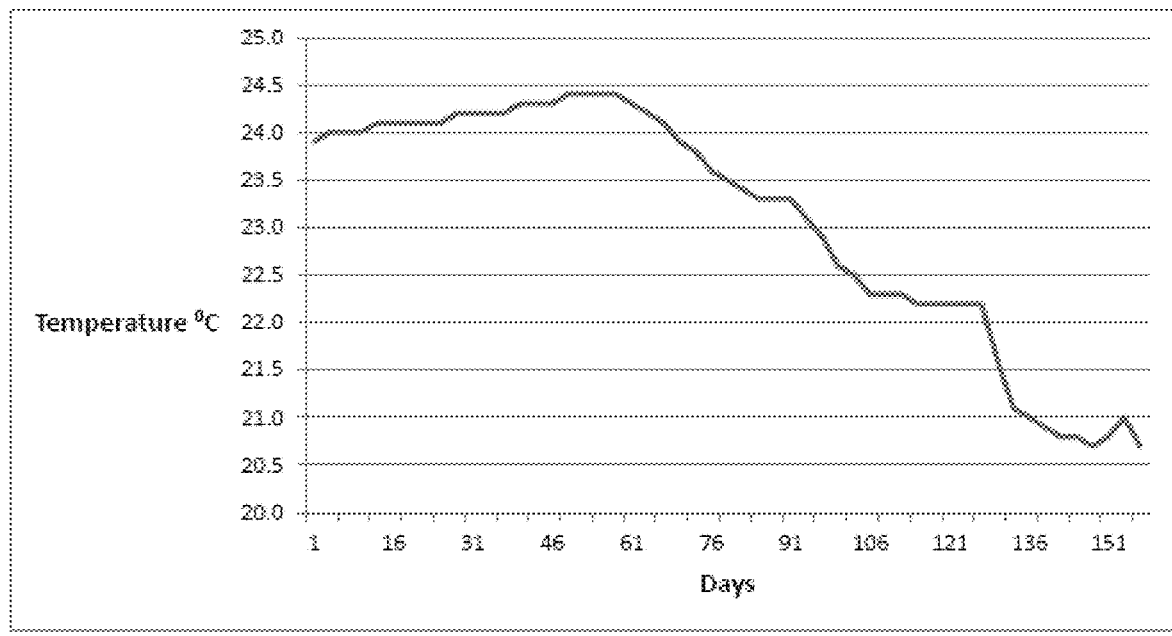
FIG. 7 is a graph illustrating the water temperature during the sea bream trial of FIG. 2.
FIG. 8 is a table of the expected growth rate and feeding chart of sea bream.
Figure 13A:
FIGS. 13A-13E are photographs of the experimental set up for the sea bream trial in FIG. 2.
Figure 13B:
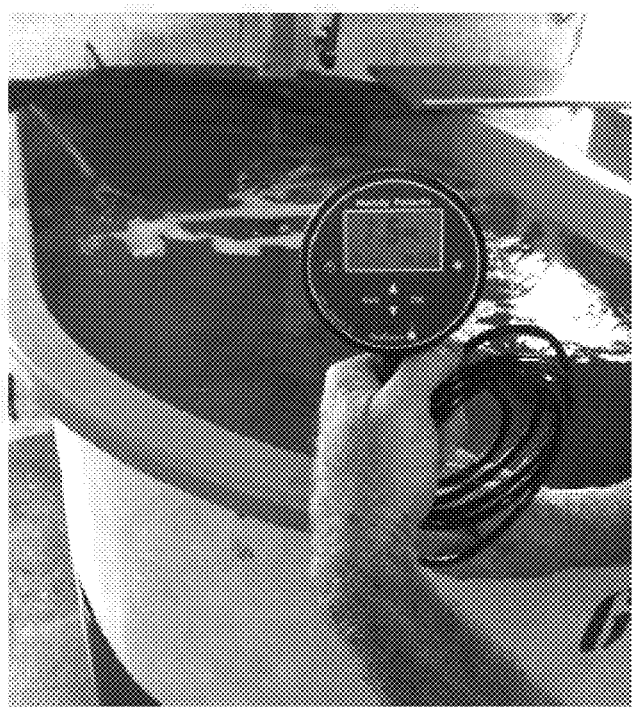
Figure 13C:
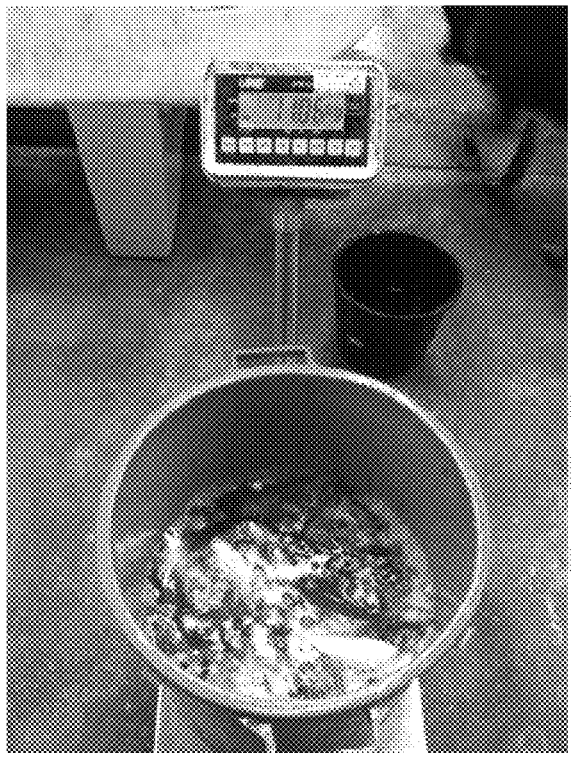
Figure 13D:
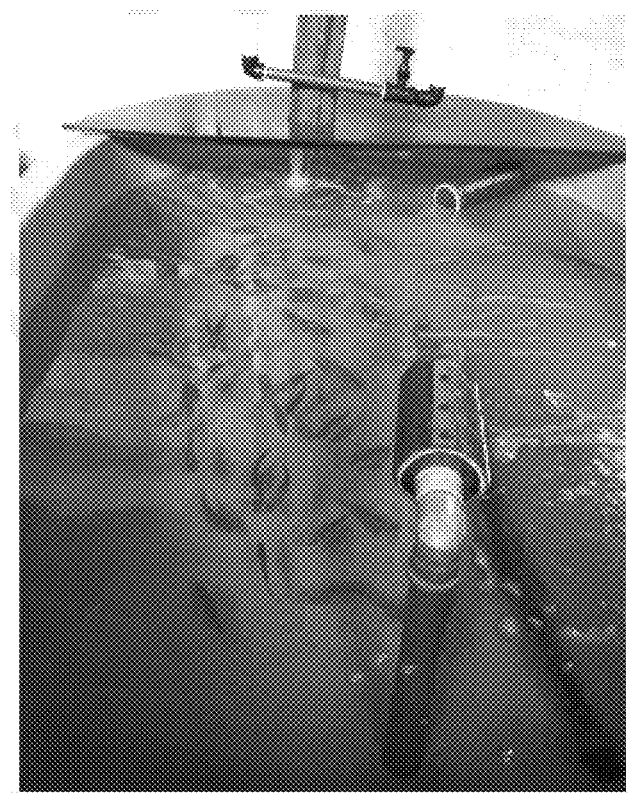
Figure 13E:
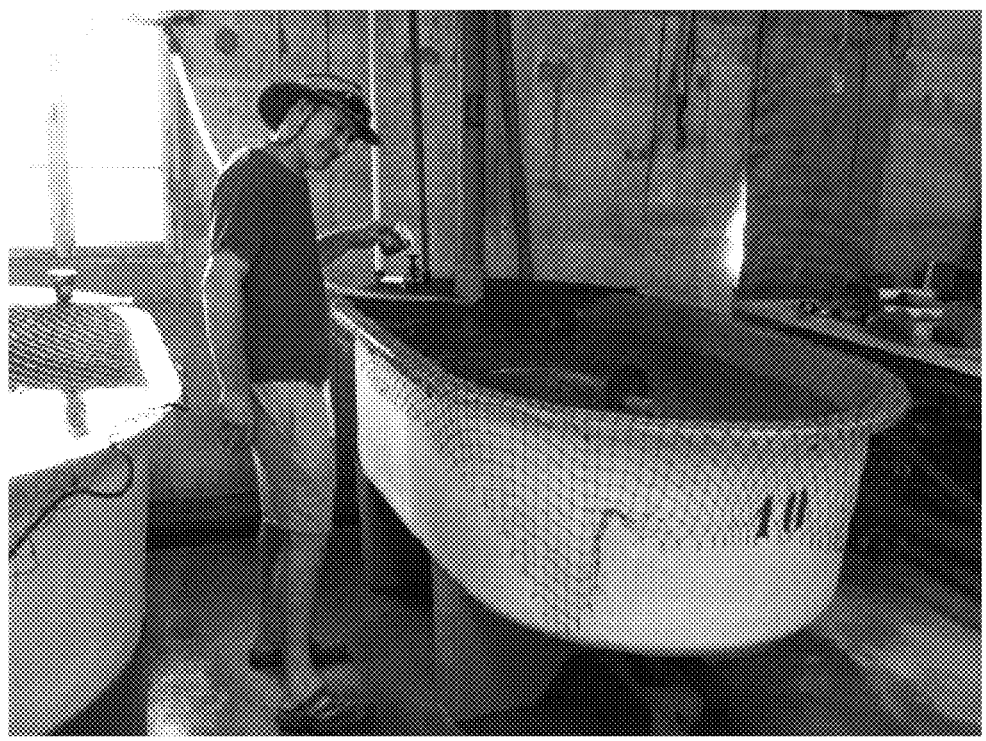

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Antimicrobial: An agent that kills and/or inhibits the growth of microorganisms. As used herein, antimicrobials include antibiotics, antifungals, antivirals, and antiparasitics including anticoccidials, or combinations thereof.

Administering: Administration by any route to the subject. As used herein, administration to aquatic species typically refers to oral administration.

Binding agent or binder: A material or substance that is used to hold or draw together other materials to form a cohesive unit.

Combination: A combination includes two or more components that are administered such that the effective time period of at least one component overlaps with the effective time period of effective time periods of all components administered overlap with each other. In an exemplary embodiment of a combination comprising four components, the effective time period of the first component administered may overlap with the effective time periods of the second, third and fourth components, but the effective time periods of the second, third and fourth components independently may or may not overlap with one another. In another exemplary embodiment of a combination comprising four components, the effective time period of the first component administered overlaps with the effective time period of the second component, but not that of the third or fourth; the effective time period of the second component overlaps with those of the first and third components; and the effective time period of the fourth component overlaps with that of the third component only. A combination may be a composition comprising the components, a composition comprising one or more components and another separate component (or components) or composition(s) comprising the remaining component(s), or the combination may be two or more individual components. In some embodiments, the two or more components may comprise the same component administered at two or more different times, two or more different components administered substantially simultaneously or sequentially in any order, or a combination thereof.

Excipient or carrier: A physiologically inert substance that is used as an additive in (or with) a combination, composition, or component as disclosed herein. As used herein, an excipient or carrier may be incorporated within particles of a combination, composition, or component, or it may be physically mixed with particles of a combination, composition, or component. An excipient or carrier can be used, for example, to dilute an active agent and/or to modify properties of a combination or composition. Examples of excipients and carriers include, but are not limited to, calcium carbonate, polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

Feed conversion rate: A measure of the efficiency of an animal to convert feed mass into increased body mass; also known in the art as feed conversion ratio (which is expressed herein as a dimensionless number).

Feedstuff: Anything that may be consumed by an animal. The term "feedstuff" includes, but is not limited to, solid and liquid animal feeds (e.g., a feed ration), supplements (e.g., a mineral supplement), water, and feed additive carriers (e.g., molasses).

Mannans: A class of polysaccharides including the sugar mannose. The mannans family includes pure mannans (i.e., the polymer backbone comprises of mannose monomers), glucomannan (the polymer backbone comprises mannose and glucose), and galactomannan (mannans or glucomannan in which single galactose residues are linked to the polymer backbone). Mannans are found in cell walls of some plant species and yeasts, and may be provided as extracts of such plant species and/or yeasts.

Mineral clay: The term "mineral clay" refers to hydrous aluminum silicates. Mineral clays usually include minor amounts of impurities, such as potassium, sodium, calcium, magnesium, and/or iron. Mineral clays typically have a two-layer sheet structure including tetrahedral silicate sheets and octahedral hydroxide sheets or a three-layer structure including a hydroxide sheet between two silicate sheets.

Polyphenols: A class of natural, synthetic, or semisynthetic organic chemicals characterized by the presence of plural phenolic

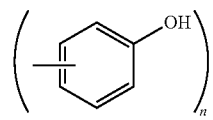

structural units.

Saponin: A class of chemical compounds, one of many secondary metabolites found in natural sources, with saponins found in particular abundance in various plant species. More specifically, they are amphipathic glycosides grouped, in terms of structure, by their composition. In certain embodiments, saponin comprises one or more hydrophilic glycoside moieties combined with a lipophilic triterpene derivative.

Therapeutic agent: An agent that is capable of providing a therapeutic effect, e.g., preventing a disorder, inhibiting a disorder, such as by arresting the development of the disorder or its clinical symptoms, or relieving a disorder by causing regression of the disorder or ameliorating its clinical symptoms.

Therapeutically effective amount: A quantity or concentration of a specified compound, composition or combination sufficient to achieve an effect in a subject.

Additional disclosure is provided by U.S. patent application Ser. No. 14/699,740, U.S. patent application Ser. No. 13/566,433, U.S. patent application Ser. No. 13/872,935, U.S. Patent Publication No. 2013/0017211, U.S. Patent Publication No. 2012/0156248, U.S. Patent Publication No. 2007/0253983, U.S. Patent Publication No. 2007/0202092, U.S. Patent Publication No. 20070238120, U.S. Patent Publication No. 2006/0239992, U.S. Patent Publication No. 2005/0220846, U.S. Patent Publication No. 2005/0180964, and Australian Patent Application No. 2011201420, each of which is incorporated herein by reference in its entirety.

II. Compositions and/or Combinations

A. Compositions and/or Combinations Comprising Glucan, Silica, Mineral Clay and/or Mannans Disclosed herein are embodiments of compositions and/or combinations for use in aquaculture and formulated for feeding to aquatic animals including, but not limited to, fish, crustaceans, and mollusks. Aquatic animals may be raised for human consumption, ornamental use, or other reasons.

Certain disclosed embodiments of the composition and/or combination comprise glucan (e.g., β-1,3 (4)glucan), silica, mineral clay, mannans or any combination thereof, and may further comprise an adhesive agent. In some embodiments, the composition and/or combination further comprises an endoglucanohydrolase, such as β-1,3 (4)-endoglucanohydrolase, either endogenously or as an affirmatively added ingredient.

The composition and/or combination may comprise, consist essentially of, or consist of, glucan (e.g., β-1,3 (4)glucan), silica, mineral clay and mannans. In some embodiments, the composition and/or combination comprises, consists essentially of, or consists of, glucan (e.g., β-1,3 (4)glucan), silica, mineral clay, mannans and endoglucanohydrolase. In other embodiments, the composition and/or combination comprises, consists essentially of, or consists of, glucan (e.g., β-1,3 (4)glucan), silica, mineral clay, mannans, endoglucanohydrolase and an adhesive agent. In further embodiments, the composition and/or combination comprises, consists essentially of, or consists of, glucan (e.g., β-1,3 (4)glucan), silica, mineral clay, mannans, endoglucanohydrolase, an adhesive agent and a feedstuff.

The composition and/or combination may comprise, consist essentially of, or consist of, silica, mineral clay and yeast cell wall extract. In some embodiments, the composition and/or combination comprises, consists essentially of, or consists of, silica, mineral clay, yeast cell wall extract and an adhesive agent. In other embodiments, the composition and/or combination comprises, consists essentially of, or consists of, silica, mineral clay, yeast cell wall extract, an adhesive agent and a feedstuff.

The composition and/or combination may comprise glucan, silica, mineral clay or mannans. Alternatively, the composition and/or combination may comprise glucan and silica, glucan and mineral clay, glucan and mannans, silica and mineral clay, silica and mannans, or mineral clay and mannans. In some embodiments, the composition and/or combination comprises glucan, silica and mineral clay, glucan, silica and mannans, or silica, mineral clay and mannans, and in certain embodiments, the composition and/or combination comprises glucan, silica, mineral clay and mannans. Any of these embodiments may further comprise an adhesive agent. Exemplary such embodiments include, but are not limited to, silica, glucan, and adhesive agent; glucan, mineral clay, mannans, and adhesive agent; glucan, silica, mineral clay, mannans, and an adhesive agent;

or silica, mineral clay, yeast cell wall extract and an adhesive agent. Additionally, or alternatively, any of these embodiments may further comprise an endoglucanohydrolase.

In some embodiments, the components are in a composition. In other embodiments, the components are in a combination, which may comprise individual components, or may comprise one or more compositions each comprising one or more components, and/or other separate components.

Suitable sources of silica include, but are not limited to, sand, diatomaceous earth, and synthetic silica. In one embodiment, quartz may be used. In certain embodiments, the mannans comprise glucomannan.

The components of the composition and/or combination are prepared by methods commonly known in the art and can be obtained from commercial sources. β-1,3 (4)-endoglucanohydrolase may be produced from submerged fermentation of a strain of Trichoderma longibrachiatum. Diatomaceous earth is available as a commercially-available, acid-washed product with 95% silica ($SiO_2$) and with its remaining components not assayed but primarily ash (minerals) as defined by the Association of Analytical Chemists (AOAC, 2002). The mineral clays (e.g., aluminosilicates) used in this composition and/or combination may be any of a variety of commercially-available clays including, but not limited to, montmorillonite clay, bentonite and zeolite. Glucan, mannans, and/or endoglucanohydrolase can be obtained from plant cell walls, yeast (e.g., Saccharomyces cerevisiae, Candida utilis), certain fungi (e.g., mushrooms), and bacteria. In certain embodiments, yeast can be affirmatively administered to provide glucan, mannans and endoglucanohydrolase endogeneously.

In one embodiment, the composition and/or combination includes 1-40 wt % silica, 1-25 wt % glucan and mannans, and 40-92 wt % mineral clay in amounts relative to each other. In another embodiment, the composition and/or combination comprises 5-40 wt % silica, 2-15 wt % glucan and mannans, 40-80 wt % mineral clay in amounts relative to each other, and/or an effective amount of adhesive agent, such as at least 2 wt % adhesive agent. In another embodiment, the composition and/or combination comprises 20-40 wt % silica, 4-10 wt % glucan and mannans, 50-70 wt % mineral clay in amounts relative to each other, and/or an effective amount of an adhesive agent, such as at least 2 wt % adhesive agent. In another embodiment, the composition and/or combination comprises 15-40 wt % silica, 1-15 wt % glucans, 0-10 wt % mannans, 50-81 wt % mineral clay in amounts relative to each other, and/or an effective amount of adhesive agent, such as at least 2% adhesive agent. In another embodiment, the composition and/or combination comprises 15-40 wt % silica, 1.0-5.0 wt % glucans, 1.0-8.0 wt % mannans, 50-81 wt % mineral clay in amounts relative to each other, and/or an effective amount of adhesive agent, such as at least 2 wt % adhesive agent. In another embodiment, the composition and/or combination comprises 20-30 wt % silica, 1.0-3.5 wt % glucans, 1.0-6.0 wt % mannans, 60-75 wt % mineral clay in amounts relative to each other, and/or an effective amount of adhesive agent, such as at least 2% adhesive agent.

In some embodiments, β-glucans and mannans are obtained from yeast or yeast cell wall extract. The composition and/or combination may comprise 1-40 wt % silica, 1-30 wt % yeast and 40-92 wt % mineral clay, or 1-40 wt % silica, 1-30 wt % yeast cell wall extract, 40-92 wt % mineral clay, in amounts relative to each other. In one embodiment, the composition and/or combination comprises 10-40 wt % silica, 5-20 wt % yeast cell wall extract, 40-80 wt % mineral clay in amounts relative to each other, and/or at least 2% adhesive agent. In another embodiment, the composition and/or combination comprises 15-30 wt % silica, 5-15 wt % yeast cell wall extract, 55-70 wt % mineral clay in amounts relative to each other, and/or at least 2% adhesive agent.

In any of the above embodiments, the composition and/or combination may further comprise an endoglucanohydrolase, such as β-1,3 (4)-endoglucanohydrolase. The composition and/or combination may include from 0.05 wt % endoglucanohydrolase to 5 wt % endoglucanohydrolase or more, such as from 0.05 wt % to 3 wt % β-1,3 (4)-endoglucanohydrolase, relative to the amounts of silica, mineral clay, glucan, mannans, and/or yeast cell wall present in the composition and/or combination. In one embodiment, the composition and/or combination consists essentially of 0.1-3 wt % β-1,3 (4)-endoglucanohydrolase, 20-40 wt % silica, 2-20 wt % glucan and mannans, 50-70 wt % mineral clay, and/or at least 2% adhesive agent. In another embodiment, the composition and/or combination consists essentially of 0.2-3 wt %, β-1,3 (4)-endoglucanohydrolase, 20-40 wt % silica, 4-10 wt % glucan and mannans, 50-70 wt % mineral clay, and/or at least 2% adhesive agent. In any of the above embodiments, the silica may be provided by diatomaceous earth. In any of the above embodiments, the glucans may be β-glucans. In some embodiments, the β-glucans can be obtained from yeast, or other materials, such as fungi, algae, or the like. In any of the above embodiments, the mannans may comprise glucomannan.

The glucan and mannans (or yeast or yeast cell wall extract) can be prepared by a method known to a person of ordinary skill in the art and as further disclosed by the patent documents incorporated herein by reference. Yeast cell wall extract may have a composition comprising 0-8% moisture and 92-100% dry matter. The dry matter may comprise 10-55% protein, 0-25% fats, 0-2% phosphorus, 10-30% β-glucan, 0-25% mannans, and 0-5% ash. In an independent embodiment, a commercial source of β-1,3 (4) glucan and glucomannan derived from primary inactivated yeast (Saccharomyces cerevisiae) with the following chemical composition can be used: moisture 3.5-6.5%; proteins 1-6%; fats 0-0.5%; phosphorus 0-0.2%; mannans 9-20%; β-1, 3-(4) glucan 9-18%; and ash 75-85%.

In another independent embodiment, the yeast cell wall extract comprises moisture 2-3% and dry matter 97-98%, and the dry matter may comprise proteins 14-17%, fats 20-22%, phosphorus 1-2%, mannans 22-24%, β-1, 3-(4) glucan 24-26%, and ash 3-5%.

In an independent embodiment of the composition and/or combination, silica, glucan and mannans, and mineral clay are combined at 1-40%, 1-25% and 40-92%, respectively. In an independent embodiment of the composition and/or combination, β-1,3 (4)-endoglucanohydrolase, diatomaceous earth, yeast cell wall extract and mineral clay are combined at 0.05-3%, 1-40%, 1-20% and 40-92%, respectively. In an independent composition and/or combination, β-1,3 (4)-endoglucanohydrolase, diatomaceous earth, yeast cell wall extract and mineral clay are combined at 0.1-3%, 5-40%, 2-10% and 40-80%, respectively. In another independent embodiment of the composition and/or combination, β-1,3 (4)-endoglucanohydrolase, diatomaceous earth, yeast cell wall extract and mineral clay are combined at 0.2-3%, 30-40%, 4-6% and 50-65%, respectively.

B. Composition and/or Combinations Comprising Polyphenols

Additionally, or alternatively, the composition and/or combination may comprise a polyphenol. In some embodiments, the polyphenol is in a plant extract. Embodiments of disclosed plant extracts can be prepared from polyphenol-containing plant material. The plant material also may include non-polyphenol compounds, including polyphenol degradation products, such as gallic acid and trans-caftaric acid. Degradation can occur, for example, through oxidative and/or biological processes. Both the polyphenols and the non-polyphenol compounds may have biological activity. The plant extract may be prepared from a single plant material (e.g., grapes) or from a combination of plant materials. In some embodiments, the plant extract is prepared from a pressed plant material, such as grape pomace, a dried plant material, such as tea, or a combination thereof. Pomace may be obtained substantially immediately post-pressing or as an ensiled product, i.e., pomace collected and stored for up to several months post-pressing. Suitable plants have a plurality of polyphenols and/or other non-polyphenolic compounds, including but not limited to non-polyphenolic organic acids (such as gallic acid and/or trans-caftaric acid), flavanols, gallate esters, flavanodiols, phloroglucinol, pyrogallol, and catechol. In some embodiments, the plant extract is prepared from Pinot noir pomace, Pinot gris pomace, or green tea.

In some embodiments, pressed or dried plant material is ground to a fine powder prior to, or during, extraction. Pressed plant materials may be frozen to facilitate grinding. Polyphenols and other non-polyphenolic compounds may be extracted for administration. For example, polyphenols and other non-polyphenolic compounds may be extracted from the powder using a solution comprising a polar solvent, such as water, an alcohol, an ester, or a combination thereof. In some embodiments, the solution comprises a water-miscible alcohol, ester, or combination thereof, such as a lower alkyl alcohol, lower alkyl ester, or a combination thereof. In some embodiments, the solution is water or an aqueous solution comprising 25-99% of a non-aqueous solvent, such as 25-95% non-aqueous solvent, 30-80% non-aqueous solvent, or 50-75% non-aqueous solvent, and water. In certain embodiments, the solution is an aqueous solution comprising methanol, ethanol, isopropanol, ethyl acetate, or a combination thereof. The solution may be acidified by addition of an acid. The acid may prevent or minimize oxidative degradation of biologically-active polyphenols and other non-polyphenolic compounds in the extract. The acid may be any suitable acid, such as a mineral acid (e.g., hydrochloric acid, sulfuric acid, nitric acid, etc.), or an organic acid, such as citric acid or acetic acid. In some embodiments, the solution comprises from 0.01% to 1% acid, such as 0.02-0.5%, 0.025-0.25%, or 0.05-0.15%. In some examples, the solution includes 0.1% hydrochloric acid.

Extraction may be performed at a temperature ranging from 0–100° C. In some embodiments, extraction is performed at a temperature ranging from 20–70° C., or at ambient temperature. Extraction is performed for a period of time effective to extract a polyphenol or polyphenols, such as for a period ranging from several minutes to several days. To increase extraction efficiency, the plant material and solution may be mixed or agitated during extraction, such as by grinding the plant material during extraction, stirring the mixture, shaking the mixture, or homogenizing the mixture. In some embodiments, the extraction may be repeated one or more times with fresh solution to increase recovery of polyphenols and other non-polyphenolic compounds from the plant material. The liquid phases from each extraction cycle are then combined for further processing.

The liquid phase can be recovered, and the residual solids, or pulp, discarded. Recovering the liquid phase may comprise decanting the liquid from the remaining solids and/or filtering the liquid phase to remove residual solids. The solvent (alcohol, ester, or combination thereof) can be removed from the liquid solution by any suitable means, such as evaporation (e.g., roto-evaporation), to produce an aqueous extract containing the biologically-active components in a mildly acidic solution.

In certain embodiments where the plant material includes a significant amount of oils, or lipids, an initial extraction of nonpolar components may be performed before extracting the polyphenols and other polar, non-polyphenolic compounds. Nonpolar components may be extracted by homogenizing the plant material in a nonpolar solvent, e.g., hexanes, heptanes, or a combination thereof. The solvent layer including the extracted nonpolar components is separated from the plant material and discarded.

The aqueous plant extract may be further purified by suitable means, e.g., extraction, chromatographic methods, distillation, etc., to remove non-polyphenolic compounds and/or to increase the concentration of polyphenols relative to other compounds in the extract.

The aqueous plant extract may be dried, for example by freeze-drying or other low-temperature drying methods, and ground to a powder to provide a dried plant extract. In some embodiments, the dried plant extract comprises 0.01 wt % to 25 wt % total polyphenols, such as 0.01 wt % to 10 wt %, 0.01 wt % to 5 wt %, 0.01 wt % to 2.5 wt %, 0.01 wt % to 1 wt %, 0.01 wt % to 0.5 wt %, 0.02 to 0.25 wt %, or 0.03-0.1 wt % total polyphenols. In certain embodiments, the dried plant extract further comprises non-polyphenolic compounds. For example, the dried plant extract may comprise 0.01-1 mg/g gallic acid, such as 0.05-0.5 mg/g or 0.09-0.25 mg/g gallic acid, and/or 0.001-0.1 mg/g trans-caftaric acid, such as 0.005-0.05 mg/g or 0.01-0.025 mg/g trans-caftaric acid.

The aqueous plant extract may be concentrated to a smaller volume, e.g., by evaporation, and used as an aqueous plant extract. In other embodiments, the aqueous plant extract is mixed with a carrier before drying and grinding. Suitable carriers include, for example, diatomaceous earth, silica, maltodextrin, ground grain (e.g., corn), meals (e.g., soybean or cottonseed meal) by-products (e.g., distiller's dried grains, rice hulls, wheat mill run), clays (e.g., bentonite), and combination thereof. The plant extract may be combined with a carrier in any suitable ratio, such as a ratio ranging from 10:1 to 1:10 by weight, such as from 5:1 to 1:5. For example, the plant extract may be mixed with diatomaceous earth in a ratio of 3:1 by weight.

C. *Quillaja* and *Yucca* Compositions and/or Combinations

Additionally, or alternatively, the composition and/or combination may comprise *yucca, quillaja* or both. In some embodiments a probiotic, for example *Bacillus coagulans*, may also be added. In some embodiments, disclosed combinations and/or compositions comprising *yucca, quillaja* and/or a *bacillus* species also can improve the feed conversion rate of certain animals that are raised for human consumption, for example fish, crustaceans and/or mollusks. In yet additional embodiments, the combinations and/or compositions can be used to improve animal health generally.

Examples of *yucca* include, but are not limited to, *Yucca aloifolia, Yucca angustissima, Yucca arkansana, Yucca baccata, Yucca baileyi, Yucca brevifolia, Yucca campestris, Yucca capensis, Yucca carnerosana, Yucca cernua, Yucca coahuilensis, Yucca constricta, Yucca decipiens, Yucca declinata, Yucca de-smetiana, Yucca elata, Yucca endlichiana, Yucca faxoniana, Yucca filamentosa, Yucca filifera, Yucca flaccida, Yucca gigantean, Yucca glauca, Yucca gloriosa, Yucca grandiflora, Yucca harrimaniae, Yucca intermedia,*

*Yucca jaliscensis, Yucca lacandonica, Yucca linearifolia, Yucca luminosa, Yucca madrensis, Yucca mixtecana, Yucca necopina, Yucca neomexicana, Yucca pallida, Yucca periculosa, Yucca potosina, Yucca queretaroensis, Yucca reverchonii, Yucca rostrata, Yucca rupicola, Yucca schidigera, Yucca schottii, Yucca sterilis, Yucca tenuistyla, Yucca thompsoniana, Yucca treculeana, Yucca utahensis,* or *Yucca valida.* In certain disclosed working embodiments, the *Yucca* was *Yucca schidigera.*

Examples of *quillaja* include, but are not limited to, *Quillaja brasiliensis, Quillaja* lanceolata, *Quillaja* lancifolia, *Quillaja* molinae, *Quillaja* petiolaris, *Quillaja* poeppigii, *Quillaja* saponaria, *Quillaja* sellowiana, or *Quillaja* smegmadermos.

A person of ordinary skill in the art will appreciate that, as used herein, a plant name may refer to the plant as a whole, or to any part of the plant, such as the roots, stem or trunk, bark, leaves, flower, flower stems, or seeds or a combination thereof. These plant parts may be used fresh, or dried, and may be whole, pulverized, or comminuted. The name may also refer to extracts from any part or parts of the plant, such as chemical extracts, or extracts obtained by pressing, or any other methods of concentrating or extracting oils or other extracts known to those in the art or that are hereafter discovered. Plant extracts may include compounds that are saponins, triterpenoids, polyphenols, antioxidants or resveratrol, or combinations thereof.

A composition comprising *yucca* and/or *quillaja* may also include carriers and binding agents suitable to formulate the *yucca* and/or *quillaja* for administration to an animal. In certain working embodiments, the composition can be a commercially available product, such as a composition comprising *Yucca schidigera* and *Quillaja saponaria*, which is sold under the trade name NUTRAFITO PLUS by Desert King International and/or MAGNI—PHI by Phibro Animal Health Corporation. Such composition embodiments can comprise 85% *Quillaja saponaria* and 15% *Yucca* schidigera or 90% *Quillaja saponaria* and 10% *Yucca schidigera.*

The combination and/or composition may also comprise a probiotic. The probiotic may be *Bacillus. Bacillus* is a genus of Gram-positive, rod-shaped bacteria. Examples of *Bacillus* include, but are not limited to *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. galliciensis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis, B. weihenstephanensis* or a combination thereof. In some embodiments, the probiotic is, or comprises *Bacillus coagulans*. In some embodiments, the probiotic is, or comprises *Bacillus subtillus*. In some embodiments, the probiotic is, or comprises *Bacillus amyloliquefaciens*. In some embodiments, the probiotic is, or comprises *Bacillus licheniformis*. In certain embodiments, the probiotic is, or comprises, a combination of *Bacillus subtillus, Bacillus amyloliquefaciens,* and *Bacillus licheniformis*. In other embodiments, the probiotic is or comprises *Bacillus subtillus, Bacillus amyloliquefaciens, Bacillus licheniformis* and *Bacillus coagulans.* In particular disclosed embodiments the *Bacillus* is *Bacillus coagulans*. A person of ordinary skill in the art will appreciate that, as used herein, the bacterial name may refer to the bacteria, or to a compound or compounds obtained from that bacteria. Methods of obtaining compounds from bacteria are well known in the art.

A composition comprising *bacillus* may also include additional materials, such as carriers or binding agents, suitable to formulate the *Bacillus* for administration to an animal. In certain disclosed working embodiments, a composition comprising *Bacillus coagulans* was Ganpro, a commercial product available from Ganeden Biotech, Ohio. In other disclosed working embodiments, a composition comprising *Bacillus coagulans* was Provia 6086®, available from Prince Agri Products, Inc.

D. Therapeutic Compositions and/or Combinations

In some embodiments, the disclosed composition and/or combination embodiments may be administered prophylactically to an animal to reduce the risk of the animal developing particular diseases.

The compositions and/or combinations may comprise the glucan, silica, mineral clay, and mannans compositions and/or combinations described herein, and/or may comprise the *yucca* and *quillaja* compositions described above. The composition and/or combination may further comprise an antimicrobial such as an antiparasitic (for example, an anticoccidial), an antifungal, an antibiotic, an antiviral agent, or a combination thereof; a vaccine, for example a coccidiosis vaccine; or some combination thereof. The composition and/or combination components may be administered in any order. In some embodiments, an antimicrobial, and/or a vaccine may be administered to the animal prior to administration of glucan, mannans, mineral clay, silica, polyphenol, *yucca, quillaja*, probiotic or combination thereof. Alternatively, an antimicrobial and/or vaccine can be administered to an animal, followed by administration of the glucan, mannans, mineral clay, silica, polyphenol, *yucca, quillaja*, probiotic or combination thereof. In such embodiments, the antimicrobial and/or vaccine may be administered simultaneously with any or all of the glucan, mannans, mineral clay, silica, polyphenol, *yucca, quillaja*, probiotic or combination thereof, or before or after any or all of the components are administered. In an independent embodiment, an antimicrobial need not be administered. In yet other independent embodiments, a vaccine need not be administered.

An antimicrobial may be selected from an antibiotic, an antifungal, an antiparasitic, an antiviral, or a combination thereof. An antibiotic may be selected from, by way of example, and without limitation, virginiamycin, Bacitracin MD, Zinc Bacitracin, Tylosin, Lincomycin, Flavomycin, bambermycins, Terramycin, Neo-Terramycin, florfenicol, oxolinic acid, oxytetracycline, hydrogen peroxide (PeroxAid® 35%), bronopol (2-bromo-2-nitro-1,3-propanediol, Pyceze®), sulfadimethozine, ormetoprim, Sulfadiazine, Trimethoprim, or a combination thereof. In some embodiments, the antibiotic is not, or does not comprise, hydrogen peroxide. In some embodiments, the antibiotic is virginiamycin, Bacitracin MD, Zinc Bacitracin, Tylosin, Lincomycin, Flavomycin, bambermycins, Terramycin, Neo-Terramycin, florfenicol, oxolinic acid, oxytetracycline, bronopol (2-bromo-2-nitro-1,3-propanediol, Pyceze®), sulfadimethozine, ormetoprim, Sulfadiazine, Trimethoprim, or a combination thereof.

An antifungal may be selected from, by way of example, formalin, formalin-F, bronopol (2-bromo-2-nitro-1,3-propanediol, Pyceze®), or a combination thereof. Exemplary antiparasitics may be selected from an anticoccidal, copper sulfate, fenbendazole, formalin, formalin-F, hyposalinity, hadaclean A, praziquantel, emamectin benzoate (SLICE®), or a combination thereof.

Suitable anticoccidial agents include, but are not limited to, ionophores and chemical anticoccidial products. Ionophores can include, but are not limited to, Monensin, Salinomycin, Lasalocid, Narasin, Maduramicin, Semduramicin, or combinations thereof.

Chemical anticoccidial products can include, but are not limited to, Nicarbazin, Maxiban, Diclazuril, Toltrazuril, Robenidine, Stenorol, Clopidol, Decoquinate, DOT (zoalene), Amprolium, or combinations thereof.

Suitable vaccines can be selected from live coccidiosis vaccines, such as COCCIVAC (e.g., a composition comprising live oocysts of *Eimeria acervulina, Eimeria mivati, Eimeria maxima, Eimeria mitis, Eimeria tenella, Eimeria necatrix, Eimeria praecox, Eimeria brunetti, Eimeria hagani*, or combinations thereof), LivaCox (a composition comprising 300-500 live sporulated oocysts of each attenuated line of *Eimeria acervulina, E. maxima* and *E. tenella* in a 1% w/v aqueous solution of Chloramine B), ParaCox (a composition comprising live sporulated oocysts derived from *E. acervulina* HP, *E. brunetti* HP, *E. maxima* CP, *E. maxima* MFP, *E mitis* HP, *E. necatrix* HP, *E. praecox* HP, *E. tenella* HP, and combinations thereof), Hatch Pack Cocci III (a composition comprising oocysts derived from *Eimeria acervulina, Eimeria maxima, Eimeria tenella*, or combinations thereof), INOVOCOX (a composition comprising oocysts derived from *Eimeria acervulina, Eimeria maxima, Eimeria tenella*, and a sodium chloride solution), IMMUCOX (a composition comprising live oocysts derived from *Eimeria acervulina, Eimeria maxima, Eimeria necatrix, Eimeria tenella*, and combinations thereof), Advent, or combinations thereof. Vaccines may also comprise live oocysts of the *Eimeria* genus, for example, *Eimeria aurati, Eimeria baueri, Eimeria lepidosirenis, Eimeria leucisci, Eimeria rutile, Eimeria carpelli, Eimeria subepithelialis, Eimeria funduli* and/or *Eimeria vanasi*. Vaccines may also comprise oocysts from the genus *Epeimeria, a new genus of coccidia infecting fishes*.

Other suitable vaccines include, but are not limited to, ALPHA DIP® 2000, ALPHA DIP® *Vibrio*, ALPHA MARINE® *Vibrio*, ALPHA DIP® ERM Salar, ALPHA JECT Micro® 1 ILA, ALPHA JECT Micro® 7ILA, ALPHA JECT® Panga, ALPHA JECT® 1000, ALHPA JECT® 2000, ALPHA JECT® 3000, ALPHA JECT® 3-3, ALPHA JECT® 4000, ALPHA JECT® 4-1, ALPHA JECT® 5-1, ALPHA JECT® 5-3, ALPHA JECT® 6-2, ALPHA JECT® micro 1 ISA, ALPHA JECT® micro 2, ALPHA JECT® micro 4, Apex®-IHN, AQUAVAC® ERM Oral, AQUAVAC® ERM immersion, AQUAVAC® FNM Injectable, AQUAVAC® IPN Oral, AQUAVAC® RELERA™, AQUAVAC® *Vibrio* Oral, AQUAVAC® *Vibrio Pasteurella* injection, AQUAVAC® *Vibrio* immersion and injectable, AQUAVAC-COL™ immersion, AQUAVAC-ESC™ immersion, Birnagen Forte 2, Ermogen, Forte Micro, Forte V II, Forte V1, Fry Vacc 1, Furogen Dip, ICTHIOVAC JG injection, ICTHIOVAC® PD immersion, Lipogen DUO, Lipogen Forte, Microvib, Norvax® Compact PD injection, Norvax® Minova 4WD, Norvax® Minova 6 injection, Norvax® STREP Si immersion and injection, Premium Forte Plus, Premium Forte Plus ILA, Renogen, Vibrogen 2, or a combination thereof.

The amount of antimicrobial used is within the amounts stated below but may depend on the particular antimicrobial used as will be understood by a person of ordinary skill in the art. In some embodiments, the amount of the antimicrobial that is included in the composition and/or combination can range from at least 1 g/ton of feed to 230 g/ton of feed (or at least 1.1 ppm to 256 ppm), such as at least 1 g/ton of feed to 220 g/ton of feed (or at least 1.1 ppm to 243 ppm), at least 1 g/ton of feed to 100 g/ton of feed (or at least 1.1 ppm to 110 ppm), at least 1 g/ton of feed to 50 g/ton of feed (or at least 1.1 ppm to 55 ppm), or at least 1 g/ton of feed to 10 g/ton of feed (or at least 1.1 ppm to 11 ppm). Particular antimicrobials that can be used, and dosage amounts of such antimicrobials include, but are not limited to, the following: Virginiamycin in an amount ranging from 5 g/ton of feed to 25 g/ton of feed (or 5 ppm to 27 ppm, such as 22 ppm); Bacitracin MD in an amount ranging from 40 g/ton of feed to 220 g/ton of feed (or 44 ppm to 242 ppm, or 50 ppm to 250 ppm in some other embodiments); Zinc Bacitracin in an amount ranging from 40 g/ton of feed to 220 g/ton of feed (or 44 ppm to 242 ppm); Tylosin in an amount ranging from 1 g/ton of feed to 1000 g/ton of feed (or 1 ppm to 1100 ppm); Lincomycin in an amount ranging from 1 g/ton of feed to 5 g/ton of feed (or 1 ppm to 6 ppm); Flavomycin in an amount ranging from 1 g/ton of feed to 5 g/ton of feed (or 1 ppm to 6 ppm); or combinations thereof.

The amount of anticoccidial agent, as will be understood by a person of ordinary skill in the art (e.g., a veterinarian), can be selected depending on the particular anticoccidial agent used. In some embodiments, the amount of the anticoccidial agent that is included in the composition and/or combination can range from at least 1 g/ton of feed to 250 g/ton of feed (or at least 1 ppm to 275 ppm), such as at least 1 g/ton of feed to 200 g/ton of feed (or at least 1 ppm to 242 ppm), or at least 1 g/ton of feed to 150 g/ton of feed (or at least 1 ppm to 165 ppm), at least 1 g/ton of feed to 100 g/ton of feed (or at least 1 ppm to 110 ppm), or at least 1 g/ton of feed to 50 g/ton of feed (or at least 1 ppm to 55 ppm). Particular anticoccidial agents that can be used, and dosage amounts of such anticoccidial agents include, but are not limited to, the following: Monensin in an amount ranging from 35 g/ton of feed to 110 g/ton of feed (or 38 ppm to 121 ppm); Salinomycin in an amount ranging from 25 g/ton of feed to 90 g/ton of feed (or 27 ppm to 99 ppm); Lasalocid in an amount ranging from 35 g/ton of feed to 113 g/ton of feed (or 38 ppm to 125 ppm); Narasin in an amount ranging from 35 g/ton of feed to 72 g/ton of feed (or 38 ppm to 79 ppm); Maduramicin in amount ranging from 2 g/ton of feed to 7 g/ton of feed (or 2 ppm to 8 ppm); Semduramicin in an amount ranging from 12 g/ton of feed to 23 g/ton of feed (or 13 ppm to 25 ppm); Nicarbazin in an amount ranging from 60 g/ton of feed to 113 g/ton of feed (or 66 ppm to 125 ppm); Maxiban in an amount ranging from 40 g/ton of feed to 90 g/ton of feed (or 44 ppm to 99 ppm); Diclazuril in an amount ranging from 0.5 g/ton of feed to 10 g/ton of feed (or 0.6 ppm to 11 ppm); Toltrazuril in an amount ranging from 1 g/ton of feed to 10 g/ton of feed (or 1 ppm to 11 ppm); Robenidine in an amount ranging from 20 g/ton of feed to 60 g/ton of feed (or 22 ppm to 66 ppm); Stenorol in an amount ranging from 1.5 g/ton of feed to 15 g/ton of feed (or 1.5 ppm to 17 ppm); Clopidol in an amount ranging from 90 g/ton of feed to 227 g/ton of feed (or 99 ppm to 250 ppm); Decoquinate in an amount ranging from 18 g/ton of feed to 27 g/ton of feed (or 19 ppm to 29 ppm); Zoalene in an amount ranging from 25 g/ton of feed to 113 g/ton of feed (or 28 ppm to 125 ppm); Amprolium in an amount ranging from 20 g/ton of feed to 227 g/ton of feed (or 22 ppm to 250 ppm).

E. Miscellaneous Additives

In some embodiments the composition and/or combination further comprises a vitamin, a trace mineral, a bulking agent, a carrier, a colorant, a taste enhancer, or any combination thereof. In other embodiments the combination and/or composition further comprises corn, soybean meal, wheat, barley, rye, canola, corn oil, limestone, salt, distillers dried grains with solubles (DDGS), dicalcium phosphate, sodium sesquicarbonate, methionine source, lysine source, L-threonine, choline, or any combination thereof.

F. Adhesive Agent

In some embodiments, the composition and/or combination includes an adhesive agent. The amount of adhesive agent may be from zero to 10% or more by weight, such as from greater than zero to 10% or from 2% to 10% by weight. The adhesive agent is a material selected to, for example, facilitate adhering some or all of the components of the composition and/or combination together, to a foodstuff, or both. The adhesive agent also may facilitate maintaining adherence of the composition and/or combination together or to a foodstuff in an aquatic environment to facilitate administration to aquatic species. The material is also preferably palatable and edible by aquatic animals.

In some embodiments the adhesive agent is an oil. For example, the oil may be selected from corn oil, coconut oil, linseed oil cottonseed oil, olive oil, peanut oil, palm oil, canola oil, safflower oil, soy oil, sunflower oil, Naskole oil, or any combination thereof. In some embodiments, the adhesive agent is a syrup. For example, the syrup may be selected from molasses, sorghum, sugar syrup, honey, or any combination thereof. Combinations of oils and syrups also may be used.

G. Feed

The composition and/or combination may be used to replace or supplement animal feedstuffs. In some embodiments, the feedstuff is a commercial feedstuff. In particular embodiments, the feedstuff was manufactured by Raanan Fish Meal. The feed may be formulated as sinking extruded pellets #4932S0 at sizes of 2-4 mm, such as 2-3 mm. Certain particular feed embodiments comprised 45.0% protein, 12.0% fat, 3.0% carbohydrates, 9% ash, and 9.8% moisture. In other particular embodiments, the feedstuff was manufactured by Zemach Feed Mill. The feed may be formulated as floating extruded pellets #4662 at sizes of 2-4 mm, such as 2-3 mm. Certain particular embodiments comprised 35.0% protein, 3.5% fat, 14.0% carbohydrates, 8.0% ash, and 10.0% moisture. In other particular embodiments the feed used was manufactured by Zemach Feed Mill, and was based on floating extruded pellets #4212 at a size of 4 mm. Certain particular embodiments comprised 30.0% protein, 5.0% fat, 4.5% carbohydrates, 8.0% ash, and 10.0% moisture. In some embodiments, the composition or one or more of the components of the combination is coated on the feedstuffs using an adhesive agent.

H. Additional Components

In some embodiments, the composition and/or combination includes additional components. Additional components may be used for any desired purpose, such as a substantially biologically inert material added, for example, as a filler, or to provide a desired beneficial effect. Alternatively or in addition, adjuvants and/or therapeutic agents also may be included in the composition and/or combination. For example, composition and/or combination may include, without limitation, a carbonate (including a metal carbonate such as calcium carbonate), kelp, a vitamin (such as a niacin supplement or vitamin B-12 supplement), biotin, d-calcium pantothenate, choline chloride, thiamine mononitrate, pyridoxine hydrochloride, menadione dimethylpyrimidinol bisulfite, riboflavin-5-phosphate, folic acid, soybean oil, calcium aluminosilicate, rice hulls, algae, mineral oil, or any combination thereof. The algae may be a blue-green algae (cyanobacteria), a diatom (bacillariophyta), a stonewort algae (charophyta), a green algae (chlorophyta), a golden algae (chrysophyta), a dinoflagellate (dinophyta), a brown algae (phaeophyta) or a red algae (rhodophyta). In some embodiments, the algae is a chlorophyta, and may be an algae from the genus *Chlorella*, including, but not limited to, *Chlorella vulgaris, Chlorella angustoellipsoidea, Chlorella botryoides, Chlorella capsulata, Chlorella ellipsoidea, Chlorella emersonii, Chlorella fusca, Chlorella homosphaera, Chlorella luteo-viridis, Chlorella marina, Chlorella miniata, Chlorella minutissima, Chlorella mirabilis, Chlorella ovalis, Chlorella parasitica, Chlorella peruviana, Chlorella rugosa, Chlorella saccharophila, Chlorella sauna, Chlorella spaerckii, Chlorella sphaerica, Chlorella stigmatophora, Chlorella subsphaerica, Chlorella trebouxioides*, or a combination thereof. In other embodiments, the algae is a cyanobacteria, such as *Arthrospira platensis* or *Arthrospira maxima (spirulina)*. Other algae include, but are not limited to, algae of the genus *Pediastrum*, such as *Pediastrum dupl, Pediastrum boryanum*, or a combination thereof, algae of the genus *Botryococcus*, such as *Botryococcus braunii*, algae of the genus *Porphyra*, such as *Porphyra dioica, Porphyra linearis, Porphyra lucasii, Porphyra mumfordii, Porphyra purpurea, Porphyra umbilicalis*, or a combination thereof.

I. Further Compositions and/or Combinations

In some embodiments, components may be incorporated in different manners, including as a composition and/or as a combination. For example, the composition and/or combination may comprise a component 1 selected from: 1A) glucan; 1B) silica; 1C) mineral clay; 1D) mannans; 1E) polyphenol; 1F) glucan and silica; 1G) glucan and mineral clay; 1H) glucan and mannans; 1I) glucan and polyphenol; 1J) silica and mineral clay; 1K) silica and mannans; 1L) silica and polyphenol; 1M) mineral clay and mannans; 1N) mineral clay and polyphenol; 1O) mannans and polyphenol; 1P) glucan, silica and mineral clay; 1Q) glucan, silica and mannans; 1R) glucan, silica and polyphenol; 1S) glucan, mineral clay and mannans; 1T) glucan, mineral clay and polyphenol; 1U) glucan, mannans and polyphenol; 1V) silica, mineral clay and mannans; 1W) silica, mineral clay and polyphenol; 1X) mineral clay, mannans and polyphenol; 1Y) glucan, silica, mineral clay and mannans; 1Z) glucan, silica, mineral clay and polyphenol; 1AA) silica, mineral clay, mannans and polyphenol; 1AB) glucan, silica, mineral clay, mannans and polyphenol; 1AC) *quillaja;* 1AD) *yucca;* 1AE) a probiotic; 1AF) *quillaja* and *yucca;* 1AG) *quillaja* and a probiotic; 1AH) *yucca* and a probiotic; 1AI) *quillaja, yucca* and a probiotic; 1AJ) *Yucca schidigera;* 1AK) *Quillaja saponaria;* 1AL) *Bacillus coagulans;* 1AM) *Yucca schidigera* and *Bacillus coagulans;* 1AN) *Quillaja saponaria* and *Bacillus coagulans;* 1AO) *Yucca schidigera,* and *Quillaja saponaria;* 1AP) *Yucca schidigera, Quillaja saponaria* and *Bacillus coagulans;* 1AQ) an antimicrobial; 1AR) an antibiotic; 1AS) Virginamycin; 1AT) an anticoccidial agent, for example Salinomycin; 1AU) an antifungal; 1AV) an antiviral; 1AW) an antiparasitic; 1AX) a vaccine; or 1AY) an adhesive agent.

The composition and/or combination may also comprise a component 2. With respect to the component 1 embodiments, the component 2 may be, in a combination with 1A to 1AY: 2A) *quillaja;* 2B) *yucca;* 2C) a probiotic; 2D) *quillaja* and *yucca;* 2E) *quillaja* and a probiotic; 2F) *yucca* and a probiotic; 2G) *quillaja, yucca* and a probiotic; 2H) *Yucca schidigera;* 21) *Quillaja saponaria;* 2J) *Bacillus coagulans;* 2K) *Yucca schidigera* and *Bacillus coagulans;*

2L) *Quillaja saponaria* and *Bacillus coagulans;* 2M) *Yucca schidigera,* and *Quillaja saponaria;* 2N) *Yucca schidigera, Quillaja saponaria* and *Bacillus coagulans;* 2O) an antimicrobial; 2P) an antibiotic; 2Q) Virginamycin; 2R) an anticoccidial agent, for example Salinomycin; 2S) an antifungal; 2T) an antiviral; 2U) an antiparasitic; 2V) a vaccine; or 2W) an adhesive agent.

A person of ordinary skill in the art will understand that any of 2A to 2W may be combined with any of 1A to 1AY, to form any and all compositions and/or combinations between such substituents.

The composition and/or combination may comprise a component 3. With respect to the component 1 embodiments 1A to 1AY and the component 2 embodiments 2A to 2W, component 3 may be, in combination with 1A to 1AY and 2A to 2W: 3A) an antimicrobial; 3B) an antibiotic; 3C) Virginamycin; 3D) an anticoccidial agent, for example Salinomycin; 3E) an antifungal; 3F) an antiviral; 3G) an antiparasitic; 3H) a vaccine; or 3I) an adhesive agent.

A person of ordinary skill in the art will understand that any of 3A to 3I may be combined with any of 1A to 1AY and any of 2A to 2W, to form any and all compositions and/or combinations between such substituents.

The composition and/or combination may further comprise a component 4. With respect to the component 1 embodiments 1A to 1AY the component 2 embodiments 2A to 2W, and the component 3 embodiments 3A to 3I, component 4 may be, in combination with 1A to 1AY, 2A to 2W, and 3A to 3I: 4A) an antimicrobial; 4B) an antibiotic; 4C) Virginamycin; 4D) an anticoccidial agent, for example Salinomycin; 4E) an antifungal; 4F) an antiviral; 4G) an antiparasitic; 4H) an adhesive agent;

A person of ordinary skill in the art will understand that any of 4A to 4H may be combined with any of 1A to 1AY, any of 2A to 2W, and any of 3A to 3I, to form any and all compositions and/or combinations between such substituents.

The composition and/or combination may further comprise a component 5. With respect to the component 1 embodiments 1A to 1AY, the component 2 embodiments 2A to 2W, the component 3 embodiments 3A to 3I, and the component 4 embodiments 4A to 4H, component 5 may be, in combination with 1A to 1AY, 2A to 2W, 3A to 3I, and 4A to 4H: 5A) an antimicrobial; 5B) an antibiotic; 5C) Virginamycin; 5D) an anticoccidial agent, for example Salinomycin; 5E) an antifungal; 5F) an antiviral; 5G) an antiparasitic.

A person of ordinary skill in the art will understand that any of 5A to 5G may be combined with any of 1A to 1AY, any of 2A to 2W, any of 3A to 3I, and any of 4A to 4H to form any and all compositions and/or combinations between such substituents.

J. Exceptions

In any of the above embodiments, one or more of the following exceptions may apply.

If the composition and/or combination is, consists of, or consists essentially of *yucca* and/or *quillaja*; and an antibiotic, an antimicrobial, an anticoccidial agent, or a combination thereof, or if the composition and/or combination is, consists of, or consists essentially of *yucca* and/or *quillaja*; an antibiotic, an antimicrobial, an anticoccidial agent, or a combination thereof; and a vaccine, then the fish is not salmon, trout, cod, halibut, snapper, herring, or catfish; the crustacean is not lobster, shrimp, prawns, crabs, krill, crayfish, barnacles, or copepods; and the mollusk is not abalone, conchs, rock snails, whelk, clams, oysters, mussels, or cockles.

If the composition and/or combination is, consists of, or consists essentially of silica, mineral clay, glucan and mannans, and one or more of *yucca, quillaja*, a direct-fed microbial, a vitamin D species, or a plant extract, then the fish is not salmon, trout or tilapia.

In some embodiments, the antibiotic is not, or does not comprise, hydrogen peroxide.

In some embodiments, the composition and/or combination does not comprise a peroxide compound.

In some embodiments, the composition and/or combination does not comprise hydrogen peroxide.

In some embodiments, the composition and/or combination does not comprise carbamide peroxide.

In some embodiments, the composition and/or combination does not comprise urea.

In some embodiments, the composition and/or combination does not comprise hydrogen peroxide and urea.

III. Methods for Making

The composition and/or components of the combination may be formulated in any suitable form, including a powder, a granule, a pellet, a solution, or a suspension. In one embodiment, the composition and/or components of the combination are dry, free-flowing powder(s) suitable for direct inclusion into a commercially-available feed, food product or as a supplement to a total mixed ration or diet. The powder may be mixed with either solid or liquid feed or with water. In another embodiment, the composition and/or components of the combination can be formed into pellets.

Figure 57:
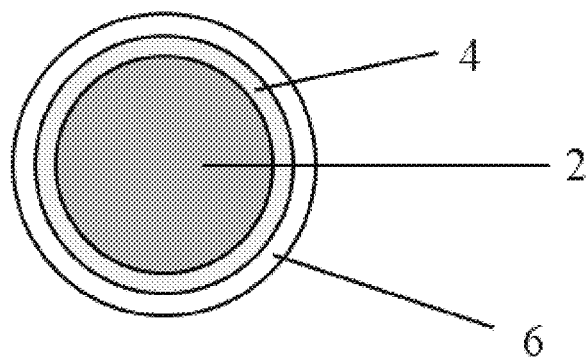
FIG. 57 is a schematic cross-sectional diagram illustrating one embodiment of a particle that comprises the composition and/or combination, a feedstuff and an adhesive agent.
Figure 58:
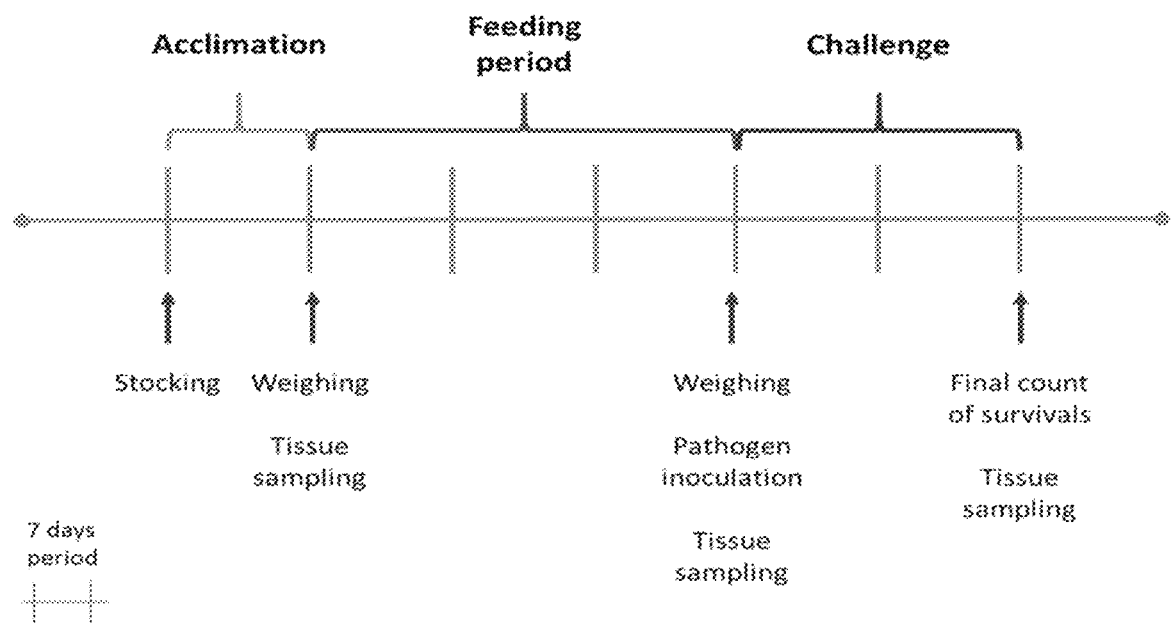
FIG. 58 is a timeline illustrating a proposed experimental shrimp trial of one embodiment of the disclosed composition and/or combination.

In some embodiments the composition and/or combination may be a powder top coated onto a feedstuff using an adhesive agent. In some embodiments the feed is mixed with adhesive agent in a mixer. The composition is added to feedstuff and mixed until all components are suitably blended. FIG. 57 provides a schematic cross sectional view of one embodiment of a particle comprising a feedstuff, adhesive agent and the composition and/or combination. With reference to FIG. 57, feedstuff 2 is at least partially coated with adhesive agent 4, and may be substantially completely coated with the adhesive agent 4. The disclosed composition and/or combination 6 forms at least a partial layer around the particle on the adhesive agent 4, and may substantially completely cover the feedstuff particle 2.

In some embodiments, the combination and/or composition was admixed with a feedstuff. In certain embodiments the combination and/or composition is formulated to be suitable to form a homogeneous mixture with the feedstuff, such as by crushing, crumbling, grinding or otherwise sizing the combination. Alternatively, the combination and/or composition may be formulated as a solution, suspension or slurry. In embodiments where the combination comprises two or more components, the components may be formulated separately or substantially together. The components may also be admixed with the feedstuff sequentially, in any order, or substantially simultaneously.

IV. Methods for Using

Embodiments of the disclosed composition and/or combination can be administered to aquatic animals to obtain one or more beneficial results. For example, embodiments of the composition and/or combination may be used to prevent and/or treat certain aquatic diseases. Additionally, the composition and/or combination may improve the feed conversion rate of an aquatic animal. A feed conversion rate, also known as a feed conversion ratio, is a measure of an animal's efficiency in converting feed mass into increased body mass. Animals with low feed conversion rates are considered efficient, as they require less feed to reach a desired weight. For example, tilapia typically have a feed conversion ratio of from 1.6 to 1.8, and farm raised salmon typically have a ratio of around 1.2. In some embodiments the feed conversion rate may be enhanced by administering the composition and/or combination by from 0.5% to 20% or more, such as from 1% to 20%, preferably from 2% to 10%, and in certain embodiments, from 3% to 5%.

For some embodiments, such as with aquatic animals, the composition and/or combination can be administered based on body weight, such as grams of the composition and/or combination per pound or kilogram body weight of fish per day, or in milligrams of the composition and/or combination per pound or kilograms of body weight. In a particular example, when administered to fish the composition and/or combination may be provided in a range of from greater than zero to 500 mg per kg of body weight per day, such as from 10 mg to 350 mg per kg of body weight per day or from 50 mg to 250 mg per kg of body weight per day. In certain embodiments, the composition and/or combination is administered to the aquatic species in an amount of from 50 mg to 200 mg per kg body weight per day, from 50 mg to 175 mg per kg body weight per day, from 50 mg to 150 mg per kg body weight per day, or from 75 mg to 125 mg per kg body weight per day.

Alternatively, the composition and/or combination is administered based on the amount of feed provided to the aquatic animals. In some embodiments, the amount of the composition and/or combination provided to the aquatic animals is from greater than zero to 10,000 mg per kg of feed or more, such as from 500 mg to 7,500 mg per kg of feed, or from 1,000 mg to 5,000 mg per kg of feed.

A person of ordinary skill in the art will appreciate that the amount of the composition and/or combination administered can vary depending upon a number of factors, including the animal species, size of the animal, the age or growth stage of the animal, and type of the feedstuff to which the combination is added. In some embodiments, 100 mg per kg of body weight per day is administered, and in other embodiments, 200 mg per kg of body weight per day is administered. In certain embodiments, 1,000 mg, 2,000 mg or 4,000 mg per kg of feed is administered to the animals.

The composition and/or combination may be administered to the aquatic species at any time period during its lifetime. The composition and/or combination may be administered throughout the aquatic species' lifetime, such as from birth or hatching to death, or it may be administered during certain times during the lifetime, including, but not limited to, hatchery, nursery, grow-out stages and/or up to harvest. The composition and/or combination may be continuously administered to the aquatic species, such as continuously administered throughout the lifetime of the aquatic species, or it may be intermittently administered, such as only during certain growth, developmental and/or life stages.

FIG. 1 provides exemplary ranges for fish for hatchery, nursery and grow-out stages, based on an administration amount of 100 mg of the composition and/or combination per kg of body weight per day. FIG. 1 illustrates that hatchery stage fish being fed at a feeding rate of 10% of body weight per day and being administered 100 mg of the composition and/or combination per kg of body weight per day, the dose of the composition and/or combination is 1,000 mg per kg of feed. This increases to 2,000 mg per kg of feed for fish at the nursery stage, and up to 4,000 mg per kg of feed for fish at the grow-out stage. FIG. 1 also provides exemplary feed sizes, of from greater than zero to 1 mm and from 1 mm to 2 mm for the hatchery stage, from 2 mm to 3 mm for the nursery stage, and 3 mm or greater for the grow-out stage. The feed size may vary depending on the species of aquatic animal as well as on the growth stage of the animal. Suitable feed sizes for particular aquatic animals at different growth stages are known to persons of ordinary skill in the art.

In particular disclosed embodiments, the composition and/or combination may be administered to aquatic animals using a carrier and/or adhesive agent. The carrier and/or adhesive agent may be any carrier and/or adhesive agent known to a person of ordinary skill in the art as being suitable for combining with a feed composition and/or combination. In other particular disclosed embodiments, the composition and/or combination may be administered to the aquatic animals using a dispersant or adhesive agent allowing the composition and or combination to be coupled to the animal feedstuffs in an aquatic environment. In some embodiments, no carrier or adhesive agent is necessary, and/or the composition and/or combination may be administered as a primary feedstuff.

The animal may be an aquatic animal, including but not limited to a fish, crustacean, and mollusk. In some embodiments, the aquatic animal is a fish or a mollusk. In other embodiments, the aquatic animal is not a crustacean. Aquatic animals may be raised for consumption, ornamental uses, or for other reasons.

The fish may be any fish, with exemplary particular species including tilapia, such as Nile tilapia, blue tilapia, Mozambique tilapia, tilapiine cichlids, or hybrids thereof; sea bream, such as sheepshead, scup, yellowfin bream, gilt-head bream, Saucereye porgies, red sea bream, or hybrids thereof carp, such as common carp, Asian carp, Indian carp, black carp, grass carp, silver carp, bighead carp, or hybrids thereof; salmon, such as pink salmon, chum salmon, sockeye salmon, coho salmon, Atlantic salmon, chinook salmon, masu salmon or hybrids thereof; trout, such as rainbow trout, Adriatic trout, Bonneville cutthroat trout, brook trout, steelhead trout or hybrids thereof; cod, such as Atlantic northeast cod, Atlantic northwest cod, Pacific cod, or hybrids thereof; halibut, such as Pacific halibut, Atlantic halibut, or hybrids thereof; snapper, such as red snapper, bluefish or hybrids thereof; herring, such as Atlantic herring or Pacific herring; catfish, such as channel catfish, walking catfish, shark catfish, *Corydoras*, basa, banjo catfish, talking catfish, long-whiskered catfish, armoured suckermouth catfish, blue catfish, or hybrids thereof; flounder, such as gulf flounder, southern flounder, summer flounder, winter flounder, European flounder, olive flounder, or hybrids thereof; hake, such as European hake, Argentine hake, Southern hake, offshore hake, benguela hake, shallow-water hake, deep-water hake, gayi hake, silver hake, North Pacific hake, Panama hake, Senegalese hake, or hybrids thereof; smelt; anchovy, such as European anchovy, Argentine anchoita, Californian anchovy, Japanese anchovy, Peruvian anchovy, Southern African anchovy, or hybrids thereof; lingcod; moi; perch, such as yellow perch, balkhash perch, European perch, or hybrids thereof; orange roughy; bass, such as European sea bass, striped bass, black sea bass, Chilean sea bass, spotted bass, largemouth sea bass, Asian sea bass, barramundi, or hybrids thereof; tuna, such as yellowfin tuna, Atlantic bluefin tuna, pacific bluefin tuna, albacore tuna, or hybrids thereof; mahi; mackerel, such as Atlantic mackerel, Short mackerel, Blue mackerel, chub mackerel, king mackerel, Atlantic Spanish mackerel, Korean mackerel, or hybrids thereof; eel, such as American eel, European eel, Japanese eel, short-fin eel, conga eel, or hybrids thereof; barracuda, such as great barracuda, Pacific barracuda, Yellowstripe barracuda, Australian barracuda, European barracuda, or hybrids thereof; marlin, such as Atlantic blue marlin, black marlin, or hybrids thereof; mullet, such as red mullet, grey mullet or hybrids thereof; Atlantic ocean perch; Nile perch; Arctic char; haddock; hoki; Alaskan pollock; turbot; freshwater drum; walleye; skate; sturgeon, such as beluga, Kaluga, starlet, or hybrids thereof; Dover sole or *Microstomus pacificus*; common sole; wolfish; sablefish; American shad; John Dory; grouper; monkfish; pompano; lake whitefish; tilefish; wahoo; cusk; bowfin; kingklip; opah; mako shark; swordfish; cobia; croaker. In certain embodiments, the term 'fish' does not include salmon or trout. In other embodiments, the fish is selected from tilapia, sea bream, carp, cod, halibut, snapper, herring, catfish, flounder, hake, smelt, anchovy, lingcod, moi, perch, orange roughy, bass, tuna, mahi, mackerel, eel, barracuda, marlin, Atlantic ocean perch, Nile perch, Arctic char, haddock, hoki, Alaskan Pollock, turbot, freshwater drum, walleye, skate, sturgeon, Dover sole, common sole, wolfish, sablefish, American shad, John Dory, grouper, monkfish, pompano, lake whitefish, tilefish, wahoo, cusk, bowfin, kingklip, opah, mako shark, swordfish, cobia, croaker, or hybrids thereof.

The composition and/or combination may be provided to any crustacean, including, but not limited to, shrimp, such as Chinese white shrimp, pink shrimp, black tiger shrimp, freshwater shrimp, gulf shrimp, Pacific white shrimp, whiteleg shrimp, giant tiger shrimp, rock shrimp, Akiama paste shrimp, Southern rough shrimp, fleshy prawn, banana prawn, Northern prawn, or hybrids thereof; crab, such as blue crab, peekytoe crab, spanner crab, Jonah crab, snow crab, king crab, stone crab, Dungeness crab, soft-shell crab, Cromer crab, or hybrids thereof; lobster, such as American lobster, spiny lobster, squat lobster, or hybrids thereof; crayfish; krill; copepods; barnacles, such as goose barnacle, picoroco barnacle, or hybrids thereof. In other embodiments, the crustacean is not a shrimp, and/or is selected from crab, lobster, crayfish, krill, copepods, barnacles, or hybrids thereof.

The mollusk may be selected from squid, such as common squid, Patagonian squid, longfin inshore squid, neon flying squid, Argentine shortfin squid, Humboldt squid, Japanese flying squid, Wellington squid, or hybrids thereof; octopus, such as the common octopus; clams, such as hard clam, soft-shell clam, ocean quahog, surf clam, Asari, Hamaguri, Vongola, Cozza, Tellina, or hybrids thereof; oysters, such as Pacific oyster, rock oyster, European flat oyster, Portuguese oyster, or hybrids thereof; mussel, such as blue mussel, freshwater mussel, green-lipped mussel, Asian green mussel, Mediterranean mussel, Baltic mussel, or hybrids thereof; abalone; conchs; rock snails; whelks; cockles; or combinations thereof.

Embodiments of the compositions and/or combinations disclosed herein can be used for feeding animals and can provide additional nutritional benefit to the animals to increase the feed conversion rates, to help support and/or maintain the animals' overall health and well-being, such as by helping increase longevity of the animal, helping boost immunity to disease, and other benefits.

A. Use in Prevention/Treatment of Disease

In some embodiments, the compositions and/or combinations can be used to help promote health in an animal at risk of developing a disease. In some embodiments, the animal can be affirmatively selected based on one or more factors that include the animal's age, decreased immunity, exposure to stressors or stress events (e.g., heat stress, crowding, ammonia toxicity, work load, chemotherapy, anti-inflammatory therapy), gastrointestinal disturbances (e.g., diarrheal diseases), or combinations thereof. In exemplary embodiments, the animal can be an aquatic animal susceptible to an environmental malady, such as an acute toxicity of ammonia due to the surrounding environment, or heat stress caused by, for example, an elevated or reduced water temperature. Ammonia toxicity may occur when an aquatic animal is exposed to an environment with ammonia concentrations of greater than about 2.0 mg/L. In some embodiments the composition and/or combination is administered prior to the animal experiencing ammonia toxicity, and/or while the animal is experiencing ammonia toxicity. In some embodiments the composition and/or combination is administered prior to the animal experiencing heat stress, and/or while the animal is experiencing heat stress. In other embodiments, the method can be used to ameliorate signs or symptoms of disease in an animal that is suffering or afflicted with a disease. Exemplary embodiments can comprise administering the combination to an animal to help ameliorate signs or symptoms of both infectious and non-infectious diseases or conditions.

Examples may include the following:

Infectious disease such as Bacteria, Viruses, Fungal agents or toxic Algae;

Environmental disease such as ammonia toxicity, nitrite toxicity, nitrate toxicity, hypoxia, increased levels of suspended solids, changes in salinity levels, hypothermia, hyperthermia or changes in pH levels;

Nutritional disease such as Vitamin deficiencies, mycotoxins or rancid feed; and Genetic disease such as anatomical disorders, lordiosis or aplasia of fins.

Stress is a condition in which an aquatic species is unable to maintain a normal physiologic state because of various factors adversely affecting its well-being. Some of the more common stress factors induced in aquaculture include:

Chemical stressors, for example, poor water quality such as low dissolved oxygen or improper pH; pollution such as intentional pollution, chemical treatments, accidental pollution, insect spray, or spills; diet composition, such as the type of protein or amino acids; and nitrogenous and other metabolic wastes, such as accumulation of ammonia, nitrate or nitrite;

Biological stressors, for example, population density such as overcrowding; other species of fish resulting in issues of aggression, territoriality and/or lateral swimming space requirements; micro-organisms, such as pathogenic and non-pathogenic organisms; and micro-organisms, such as internal and external parasites;

Physical stressors, for example, temperature, such as hypothermia and hyperthermia—this is one of the most important influences on the immune system of fish; light; sounds; and dissolved gases; and Procedural stressors, for example, handling; shipping; and disease treatments.

In some embodiments, a method of administering a composition and/or combination comprising glucan, silica, mineral clay and mannans to an animal does not include administering the composition and/or combination to an animal that is experiencing a stress event or stressor, and/or is at risk of experiencing a stress event or stressor. In other embodiments, the method of administering the composition and/or combination to an animal does not include administering the composition and/or combination to an animal that is experiencing, or is at risk of developing heat-induced stress or heat stress.

In some embodiments, a method of administering a composition and/or combination comprising glucan, silica, mineral clay and mannans to a fish does not include administering the composition and/or combination to a fish that is experiencing a stress event or stressor, and/or is at risk of experiencing a stress event or stressor.

In some embodiments, a stress event does not include heat-induced stress or heat stress, such as hyperthermia or hypothermia. In other embodiments, the environmental disease or condition is selected from ammonia toxicity, nitrite toxicity, nitrate toxicity, hypoxia, increased levels of suspended solids, changes in salinity levels, or changes in pH levels.

In some embodiments, an animal administered the composition and/or combination does not have a decreased serum cortisol level relative to an animal not fed the composition and/or combination. In other embodiments, a fish administered the composition and/or combination does not have a decreased serum cortisol level relative to a fish not fed the composition and/or combination.

Animals disclosed herein can exhibit a response, or a combination of responses, to the compositions and/or combinations (or to components thereof) disclosed herein. In some embodiments, these responses can be detected and measured to determine whether an animal's health is supported by administration of the composition and/or combination to the animal. In particular disclosed embodiments, one or more factors (or endpoints) can be used to determine an animal's response to the composition and/or combination. In some embodiments, a factor that can be examined is the ability of the composition and/or combination to increase expression of markers of innate immunity.

In some embodiments, the composition and/or combination (or a component thereof) may modify nutrient transport, and/or bind pathogenic bacteria. In another embodiment, the composition and/or combination (or a component thereof) may act as an emulsifier by dispersing molecules, thereby facilitating nutrient transport and/or increase the exposure of antigens to antigen-sensing cells in an animal's gut, including, but not limited to, M cells. In yet other embodiments, anti-oxidant, anti-inflammatory, anti-microbial, and/or anti-hypertensive properties of the composition and/or combination (or a component thereof) can be factors that are examined. In some embodiments, the ability of the composition and/or combination to beneficially affect immune modulation, metabolic regulation, nutrient utilization and/or transport, endocrine and neuroendocrine regulation, and longevity (or lifespan) can be determined.

An animal that is experiencing a stress event, or stressor, may have an elevated serum cortisol level, relative to an animal not experiencing a stress event. In some embodiments, administering the composition and/or combination to the animal that is experiencing a stress event may promote a reduction in the serum cortisol level relative to an animal that is experiencing a stress event but is not being administered the composition and/or combination.

The age of the animal that is to be administered the composition and/or combination can vary with the species. Therefore, the point at which the combination is administered can be guided by the type of animal to which the combination is being administered.

In some embodiments, the composition and/or combination can be administered daily to the animal at time intervals believed or determined to be effective for achieving a beneficial result. The composition and/or combination can be administered in a single dose daily or in divided doses throughout the day. In some instances, one or more individual combinational components or compositions thereof disclosed herein may be administered to the animal at a first time, and remaining combinational components or compositions thereof may be administered individually or in combination at one or more subsequent times during the same day.

In some embodiments the method comprises administering a combination comprising a first component and a second component and/or an additional component. The first component can comprise glucan, silica, mineral clay, mannans, polyphenol or a combination thereof. In certain embodiments, the first component comprises, consists essentially of, or consists of, glucan, silica, mineral clay and mannans. In other embodiments, the first component comprises, consists essentially of, or consists of, glucan, silica, mineral clay, mannans, and endoglucanohydrolase. In further embodiments, the first component comprises, consists essentially of, or consists of, polyphenol. The second component can comprise *yucca, quillaja*, or a combination thereof. In some embodiments, the second component comprises *Yucca schidigera, Quillaja saponaria*, or a combination thereof. The second component may also comprise a probiotic, such as a *Bacillus* species. In some embodiments, the second component comprises *Bacillus coagulans*, and in certain embodiments, the second component comprises, consists essentially of, or consists of, *Yucca schidigera, Quillaja saponaria* and *Bacillus coagulans*. The additional component can comprise an antimicrobial, an antibiotic, an antifungal, an antiparasitic such as an anticoccidial agent, a vaccine, or a combination thereof. In some embodiments, the additional component comprises Virginiamycin, Salinomycin, or a combination thereof. The amount of the antibiotic or anticoccidial agent in the second component can range from 10 ppm to 70 ppm, with some embodiments comprising from 10 ppm to 30 ppm Virginiamycin and/or at least 25 ppm to 90 ppm Salinomycin, such as 20 ppm to 80 ppm, 20 ppm to 70 ppm, 20 ppm to 60 ppm, or 20 ppm to 50 ppm. Exemplary amounts in certain working embodiments include but are not limited to, 22 ppm Virginiamycin and 50 ppm to 70 ppm, such as 66 ppm Salinomycin. Any of the above components may also comprise an adhesive agent.

Method embodiments disclosed herein also can comprise administering the composition and/or combination comprising the first component and the second composition in combination with a feedstuff. For example, the combination of the first component and the second and/or third components can be administered in combination with an amount of feedstuff suitable for obtaining an animal having a weight suitable for that particular species. In some embodiments, the amount of feedstuff that is provided to the animal can be varied according to their food intake needs as growth occurs.

In some embodiments, the composition and/or combination can comprise a first component comprising silica, glucan, mannans and mineral clay, a second component comprising *Yucca schidigera*, and *Quillaja saponaria*, a third component comprising an antimicrobial agent and/or an antibiotic, and a fourth component comprising a vaccine. A feedstuff may also be administered in such embodiments. The combination of the first, second, third and/or fourth components that are administered can be admixed with a feedstuff prior to administration to the animal, or the feedstuff may be administered before or after the combination of the first, second, third and/or fourth components. These embodiments are not intended to limit the order of administration, as any suitable order of administration can be selected.

The combination and/or composition embodiments disclosed herein can be administered using any suitable technique. In some embodiments, the combination and/or the composition is orally administered by actively introducing the composition and/or combination into the animal's mouth, or orally administered by allowing the aquatic animal to ingest the composition and/or combination on its own. The composition and/or combination may be administered to the animal during any stage of its lifecycle during which it consumes food.

Method embodiments disclosed herein improve an animal's feed conversion rate, such as by reducing the animal's feed conversion rate value, relative to animals that are fed a standard diet (e.g., a feedstuff). In an independent embodiment, the method described herein can be used to improve an animal's feed conversion rate relative to animals that are solely fed a feedstuff in combination with amounts of a composition and/or combination comprising *Yucca schidigera* and *Quillaja saponaria* ranging from 100 ppm to 150 ppm. In some embodiments, the animal is an animal raised for consumption. A feed conversion rate (feed conversion ratio) is a measure of an animal's efficiency in converting feed mass into increased body mass.

B. Improving Feed Conversion Rates

A feed conversion rate, also known as a feed conversion ratio, is a measure of an animal's efficiency in converting feed mass into increased body mass. Animals with low feed conversion rates are considered efficient, as they require less feed to reach a desired weight. For example, tilapia typically have a feed conversion ratio of from 1.6 to 1.8, and farm raised salmon typically have a ratio of around 1.2.

In some embodiments the feed conversion rate may be enhanced by from 0.5% to greater than 20%, preferably by about 2% to about 10%, and in certain embodiments, from about 3% to 5%.

In some embodiments, a composition and/or combination of *quillaja* and/or *yucca* with a probiotic, such as *Bacillus coagulans*, has a beneficial effect on animal health, typically a beneficial effect on the digestive system, including the stomach and intestines. Certain embodiments have a beneficial effect on villi health. Improved digestive health may cause improvement of a feed conversion ratio.

V. Effect on Immune System Biomarkers

Composition and/or combination embodiments disclosed herein, when administered to an animal, may produce a concomitant change in a level of, for example, an immune system biomarker or an inflammation biomarker in the animal by at least 5%, at least 10%, at least 20%, at least 30%, at least 50%, at least 75%, at least 100%, at least 200%, or at least 500%, such as from 5-600%, from 10-500%, from 10-200%, or from 10-100%, compared to an average level of the biomarker in an animal that has not received the combination. The change may be an increase or a decrease, depending on the particular biomarker.

In some embodiments, administration of the composition and/or combination may produce a concomitant change in a level of innate defense mechanisms of fish prior to exposure to a pathogen, or improve survival following exposure to a specific pathogen. Markers of improved innate immune response may include:

1. Total Leucocyte Count

Abnormal changes in total and differential blood cell counts in fish, such as anaemia, leukopaenia, leukocytosis and thrombocytopaenia, may result from diseases, but may also indicate stress, toxic exposure, hypoxia and changes in reproductive status.

Due to the nucleated nature of red blood cells (erythrocytes) in fish, white blood cells (leukocytes), which serve as an indicator of health, cannot be distinguished using automated cell counting procedures without lysis of erythrocytes and are usually manually counted using a haemocytometer. Differential leukocyte and haemocyte enumerations, which also serve as health indicators, are generally performed either on stained smears or with a haemocytometer in fish and crustacea, respectively. The disadvantage of manual enumeration is the statistical limitation associated with counting between 100 to 200 cells, the typical range in differential leukocte procedures.

Flow cytometry is an instrumental technique in which a stream of suspended particles is interrogated by one or more lasers. Particles are analysed and differentiated on the basis of their light-scattering properties, auto- or labelled fluorescence, or a combination of both.

The major advantages of flow cytometry technology are the ability to differentiate and enumerate several thousands of particles per second, and to physically sort multiple populations simultaneously into collection vessels. In haematological applications, the capability to obtain accurate and precise total and 5 differential blood counts on so many more cells than practically achievable with manual methods, in a fraction of the time, is thus dependent only on the ability to accurately discriminate between cell types.

2. Respiratory Burst (Release of Superoxide Anion)

Several reactive oxygen species (ROS) are produced by fish phagocytes during the respiratory burst. Once bacteria or fungi are engulfed by leucocytes, the host's NADPH-oxidase is activated, which in turn increases oxygen consumption and subsequently produces ROS such as superoxide anion ($O_2^-$), hydrogen peroxide ($H_2O_2$), hydroxyl radical (OH) and singlet oxygen ($^1O_2$). The release of superoxide anion is known as the respiratory burst, and the ROS released and/or formed may be are bactericidal.

3. Phagocytic Index and Activity

Phagocytosis is an essential component of the non-specific immune response against infectious agents in teleosts. This process involves the recognition and attachment of foreign particles, including pathogens, engulfment and digestion by the phagocyte. In vitro assays have been used for studying fish macrophage phagocytic activity, thereby providing an avenue for evaluating immunocompetence in fish. In vitro assays have also provided insight for non-specifically enhancing disease resistance in finfish aquaculture, and have served as immunological biomarker tests to assess aquatic environmental health.

4. Lysozyme Activity

Lysozyme found in cutaneous mucus, peripheral blood and certain tissues rich in leucocytes, is an enzyme which catalyzes the hydrolysis of N-acetyl muramic acid and N-acetyl glucosamine of peptidoglycan in bacterial cell walls. This protein plays a crucial role in the defense system.

In other embodiments, administration of the composition and/or combination may produce a concomitant change in a level of innate defense mechanisms of crustaceans prior to exposure to a pathogen, or improve survival following exposure to a specific pathogen. Markers of improved innate immune response in crustaceans may include:

1. Total Hemocyte Count

Haemocytes play a central role in crustacean immune defense. Firstly, they remove foreign particles in the hemocoel by phagocytosis, encapsulation and nodular aggregation. Secondly, haemocytes take part in wound healing by cellular clumping and initiation of coagulation processes through the release of factors required for plasma gelation.

The hemogram consists of the total haemocyte count (THC) and the differential haemocyte count (DHC). For the DHC, most researchers agree with the identification of three cell types in penaeid shrimp: large granule haemocytes (LGH), small granule haemocytes (SGH) and agranular haemocytes or hyaline cells (HC).

THC can be easily determined using a hemocytometer, whereas determination of DHC requires a more complex haemocyte identification. DHC can be determined by using morphological criteria such as size and shape of cells and the difference of haemocyte refractivity using a phase contrast microscope. Although this technique is rapid, it should be mentioned that when using this technique it is easy to obtain large variations in results possibly due to interpretation errors.

Different haemocyte types can be determined using cytochemical studies of enzyme activity detection or specific stains. The results obtained from cytochemical stains for penaeid shrimp indicate that these specific stainings can differentiate between the types of haemocytes and provide additional information on their functions. An alternative method for cell identification is the use of monoclonal antibodies (mAbs) in order to find antigenic markers of different cell types. Using mAbs against different subpopulations of haemocytes separated by isopycnic centrifugation on a Percoll gradient, it has been found in *P. japonicus* that HC share epitopes with SGH, and that an antigen was specifically expressed for LGH. Monoclonal antibodies could be considered as powerful tools for the development of haemocyte lineages and haemocyte proliferation studies, as well as for the isolation and study of plasma components.

2. Phagocytic Activity

Phagocytosis is the most common reaction of cellular defense. During phagocytosis, particles or microorganisms are internalized into the cell which later forms a digestive vacuole called the phagosome. The elimination of phagocyted particles involves the release of degradative enzymes into the phagosome and the generation of reactive oxygen intermediates (ROIs). This last process is known as the respiratory burst. The first ROI generated during this process is the superoxide anion. Subsequent reactions will produce other ROIs, such as hydrogen peroxide, hydroxyl radicals and singlet oxygen. Hydrogen peroxide can be converted to hypochlorous acid via the myeloperoxidase system, forming a potent antibacterial system.

Despite the limited number of studies focusing on respiratory burst in penaeid shrimp, the actual results are very interesting in view of their value as biomarker of environmental disturbances. Furthermore, the importance of respiratory burst as a microbicidal mechanism in penaeid shrimp is strongly suggested by the fact that pathogenic bacteria of shrimp have developed ways of circumventing this mechanism. In P. lannamei, $O_2$ generation is not produced when virulent *Vibrio iulnificus* is used as elicitor, as opposed to strong stimulation generated by *V. lginolyticus* and other bacteria, such as *Escherichia coli*.

3. Phenoloxidase (PO) and Prophenoloxidase (ProPO) Activity

The PO is responsible for the melanization process in arthropods. The PO enzyme results from the activation of the ProPO enzyme. The ProPO activating system has been very well studied in crustaceans. Using these different approaches, the function of the ProPO system can be better understood in relation to the health status of shrimp. Some studies have shown that ProPO could be used as health and environmental markers because changes are correlated with infectious state and environmental variations, this issue which has recently been confirmed also at the gene expression level. Phenoloxidase, which has been detected in a wide range of invertebrates, is activated by several microbial polysaccharides, including β-1,3-glucan from fungal cell walls and peptidoglycans or lipopolysaccharides from bacterial cell walls.

4. Antibacterial Activity

Antibacterial peptides and proteins have been well studied in arthropods, mainly in insects and chelicerata, where the families of antimicrobial molecules have been isolated and characterized. In crustacean, some studies have shown the ability of crustacean haemolymph to inhibit bacterial growth. Several antibacterial proteins, active in vitro against Gram-positive and Gram-negative bacteria, were found in *C. maenas*.

In the literature there are reports showing that antibacterial activity in crustaceans can be considered as an environmental marker. Therefore, many researchers have developed quantitative antibacterial assays based on inhibition of bacterial growth on agar plate (zone inhibition assay and colony-forming units (CFU) inhibition assay), or in liquid medium on microtiter plates (turbidometric assay), to detect the antibacterial ability in crustacean haemolymph. Using the CFU inhibition technique, antibacterial activity has been found in granular haemocytes of the shore crab *C. maenas* and in other crustacean species. It has been reported that a potent antibacterial activity in the serum of *C. sapidus*, using the zone inhibition assay and turbidimetric test. Using the CFU inhibition assay, bactericidal activity against Gram negative bacteria have been described in the haemolymph of *P. monodon*. In P. lannamei, strong antibacterial activity of plasma against different marine bacteria has been observed, using a turbidimetric assay.

5. Plasma Protein Concentration

In recent years blood metabolites have been investigated as a tool for monitoring physiological condition in wild or cultured crustaceans exposed to different environmental conditions. Hemocyanin is the major hemolymph constituent (>60%); the remaining proteins (in order of concentration) include coagulogen, apohemocyanin, hormones, and lipoproteins. Blood protein levels fluctuate with changes in environmental and physiological conditions and play fundamental roles in the physiology of crustaceans from $O_2$ transport to reproduction up to stress responses. In fact, moulting, reproduction, nutritional state, infection, hypoxia, and salinity variations are the major factors affecting the relative proportions and total quantities of the hemolymph proteins.

The shrimp immune system response is largely based on proteins. These are involved for example in recognizing foreign particles and in trapping foreign invading organisms and prevent blood loss upon wounding. Recently, it has been shown that shrimp are well adapted to use protein as a source of energy and molecules. Blood protein concentration has been found to be related to nutritional condition in a number of crustaceans. The concentration of protein in the blood is a possible index of nutritional condition, which decreases in starved prawns and lobsters. The moult cycle imposes constraints on protein levels, blood-proteins typically drop just before moulting as water is taken up and protein is used to synthesize the new exoskeleton. Protein levels then gradually build up again after ecdysis as water is replaced by tissue. Consequently, measuring the blood protein concentration of a crustacean sample group can provide valuable information to identify its condition. The concentration of protein in the blood is directly proportional to the refractive index of the blood. Measurements of the blood refractive index therefore offer potential as a field method for assessing the nutritional condition of prawns.

Colorimetric procedures are generally the preferred choice to measure serum protein concentration; however, they are expensive, time consuming, and not easily performed in the field. Because of ease, rapid mode of operation, and small amount of material required, measuring serum protein concentration using a refractometer provided a nondestructive field method to assess crustacean's physiological state (stress, immunoresponse, nutrition status, molt, etc.) without any need of laboratory facilities; the refractometer is a simple, small portable instrument that can be used in the field or on crustacean farms.

VI. Examples

The following examples are provided to illustrate certain features of working embodiments. A person of ordinary skill in the art will appreciate that the scope of the invention is not limited to only these particular features.

Example 1

A. Methods

In this example, the composition and/or combination was administered as a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans. Embodiments of the composition were used as a feed additive for sea bream. Juveniles of Gilthead sea bream (*Sparus aurata*) were stocked in 12 tanks in the experimental station. Each tank of 1.0 cubic meters was stocked with 55 juvenile sea bream at an average weight of 26 grams. The water source was from a well at a stable temperature of 21° C., with a constant total salinity of 18.0 parts per thousand. The duration of the experiment was 158 days.

The experimental protocol included continuous assessment for the presence of diseases causing organisms. Growth performance parameters of the fish were recorded regularly. The daily/weekly assessment of water quality parameters included ammonia, nitrite, pH, temperature and oxygen.

Feeding rate was based on the recommended commercial feeding chart of Phibro Aqua and adjusted according to the size of the fish and the water temperature (FIG. 8). Feeding was performed manually twice a day. The feeding quantity for each tank was adjusted after evaluating the average weight of the fish in each tank every two weeks.

The composition was top-coated on the pellets using 2 wt % of soy oil as an adhesive agent. The control group was given the same feed coated with 2 wt % soy oil. The feed preparation for the trial included mixing the weighted feed in a mixer for 5 minutes with 2 wt % soy oil, and then additional 5 minutes mixing with the composition. The experiment was carryout in replicates of 4 tanks per treatment. In the trial 2 different doses of the composition in the feed were compared: 100 milligrams per kilogram of bodyweight per day; and 200 milligrams per kilogram of bodyweight per day.

The feed used in this trial was made by Raanan Fish Meal and was based on sinking extruded pellets #4932S0 at sizes of 2-4 millimeters; containing 45.0% protein, 12.0% fat, 3.0% carbohydrates, 9% ash and 9.8% moisture.

B. Results

General Health Parameters:

1. Survival rates in all the tanks for all the treatments were high (99.1-99.5%).

2. No external or internal parasites were detected in the trial.

3. The general health condition as indicated by the vitality and the response to the feeding was very good for all the treatments for the entire trial.

A significantly higher growth rate of the fish fed with dose (A), using 100 milligrams of the composition per kilogram of bodyweight per day was obtained in this trial. A better growth rate in treatment (A) was observed by day 17. This difference became statistically significant by day 59 (FIGS. 2-4). Without being bound to a particular theory, the better growth rate may be due to an improved nutrition for the fish and/or improved immunostimulant ingredients in the feed.

As shown in this trial, the response of the fish to the composition and/or combination was significantly better compared to a control group without the composition and/or combination. This conclusion emphasized the efficacy and the advantage of the composition and/or combination as an effective feed additive in aquatic animals such as fish.

Treatment (A) had the lowest significant feed conversion ratio (FCR) value among the 3 treatments (FIG. 5). This demonstrated the advantage of the composition and/or combination as an advanced performer, improving the feed intake ability of the fish. This ability to lower the FCR value is a major factor in aquaculture management, because it reduced the feeding cost, which is often the highest cost for fish and shrimp farmers.

The environmental conditions of this example in terms of water temperature, dissolved oxygen levels and water quality were optimal for rearing sea bream. The growth rates of all the 3 groups were according to the expected growth rate of sea bream. The high percentage of survival (99.1-99.5%) in all 3 groups in this study emphasized the optimum conditions during the trial (FIGS. 6-12). The lower temperature at the end of the trial affected the optimal growth rate of the fish but still the advantages of the composition were evident. FIGS. 13A-13E illustrate the experimental setup.

Example 2

A. Methods

In this example, the composition and/or combination was administered as a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans. The composition was used as a feed additive for tilapia. Juveniles of hybrid tilapia (*Oreochromis niloticus* X *O. aureus*) were stocked in 18 cages in the experimental station. The total volume of the experimental system was 600 cubic meters. Each cage of 1 cubic meter in volume with a 25 millimeter mesh net was stocked with 35 fish at an average weight of 95 grams. The water source was from a well at a stable temperature of 24° C. The duration of the experiment was 149 days.

The experimental protocol included continuous assessment for the presence of disease causing organisms. Growth performance parameters of the fish were recorded regularly.

The daily/weekly assessment of water quality parameters included ammonia, nitrite, pH, temperature and dissolved oxygen.

Feeding rate was based on the recommended commercial feeding chart of Phibro Aqua and adjusted according to the size of the fish and the water temperature (FIG. 21). Feeding was performed manually twice a day. The feeding quantity for each cage was adjusted after evaluating the average weight of the fish in each cage every two weeks.

The composition was top-coated on the pellets using 2 wt % soy oil as the adhesive agent. The control group was given the same feed coated with 2 wt % soy oil. The feed for the trial was prepared by mixing the weighted feed in a mixer for 5 minutes with 2 wt % soy oil, and then additional 5 minutes mixing with the composition. In this trial 2 different doses of the composition in the feed were compared: 100 milligrams AI per kilogram of bodyweight per day; and 200 milligram AI per kilogram of bodyweight per day.

Replicates of 6 cages were used per treatment, which were divided equally in the rearing system. The feed for this trial was manufactured by Zemach FeedMill. The feed is based on floating extruded pellets #4662 at sizes of 2-4 millimeters; containing 35.0% protein, 3.5% fat, 14.0% carbohydrates, 8.0% ash and 10.0% moisture.

B. Results

General Health Parameters:

1. Survival rate in all the cages for all the treatments were excellent, without mortality.

2. External parasites (*Trichodina* and *Dactylogyrus*) were detected at low incidence. The fish were treated with formalin 37% and Bromex solution (50% Naled).

3. Low presence of dignea parasite, *Centrocestus*, was detected. No treatment was required.

4. The general health condition as indicated by the vitality and the response to the feeding was very good for all treatments for the entire trial.

Figure 14:
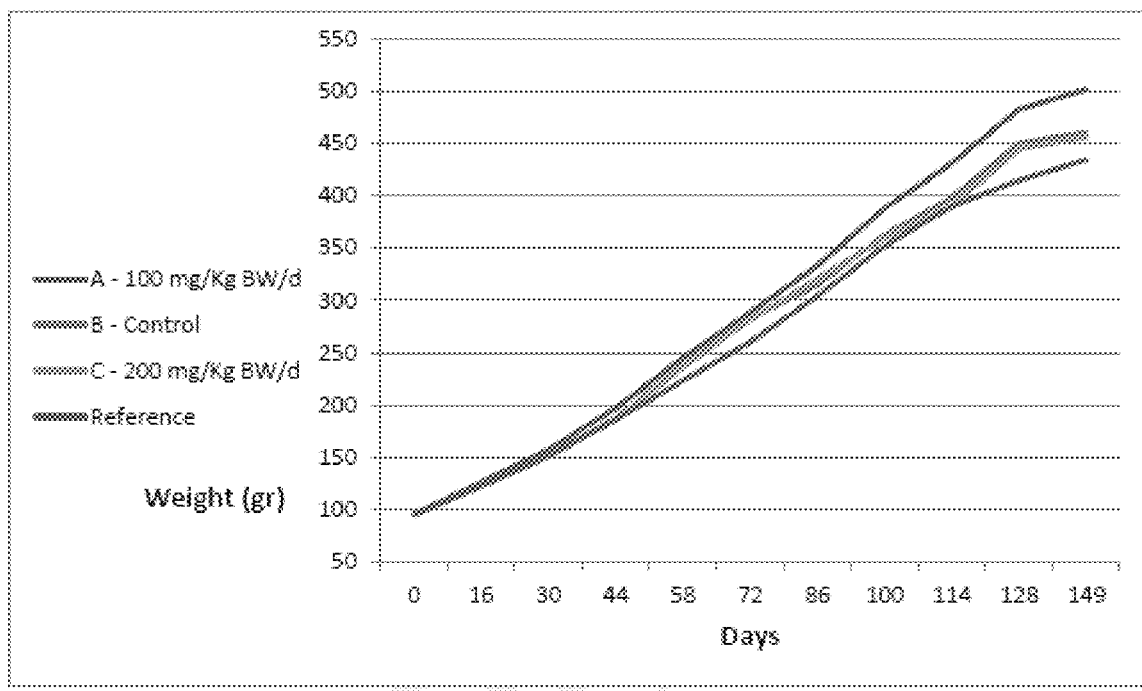
FIG. 14 is a graph of weight verses days comparing the growth rate of hybrid tilapia using two different composition feed groups and a control group.
Figure 20:
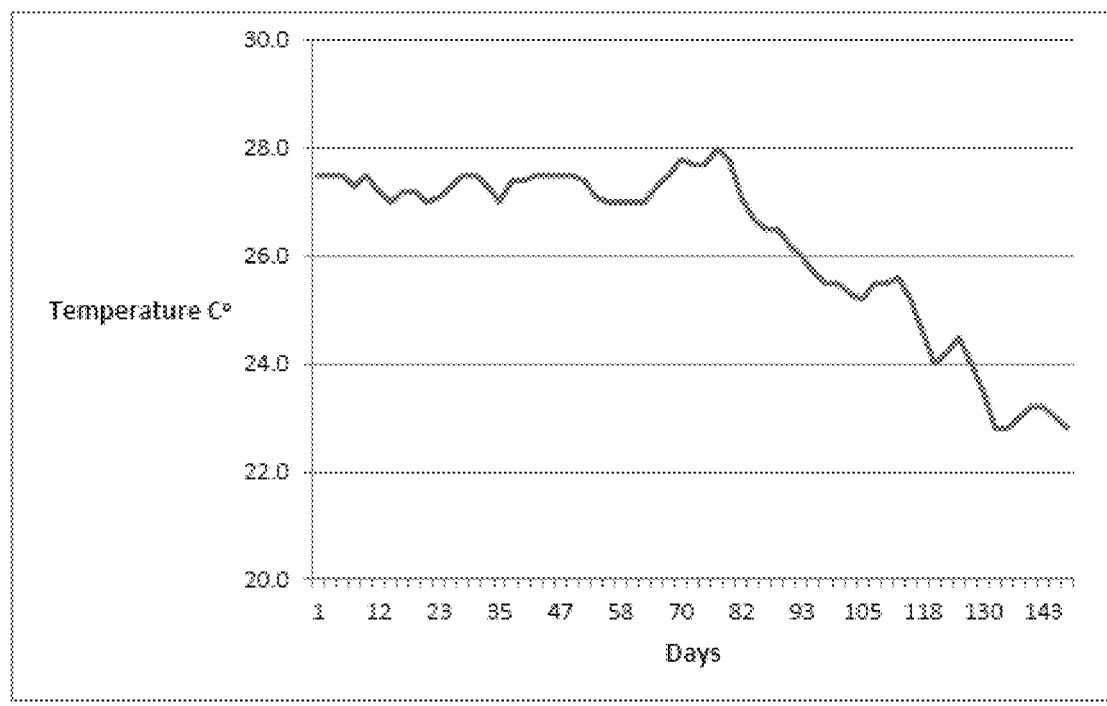
FIG. 20 is a graph showing the water temperature versus days during the hybrid tilapia trial of FIG. 14.

A significantly higher growth rate of the fish fed with dose (A), using 100 mg of the composition per kilogram of bodyweight per day was obtained in this trial. A better growth rate in treatment (A) was observed by day 16. This difference became statistically significant by day 86 (FIGS. 14-16). Without being bound to a particular theory, the better growth rate may be due to an improved nutrition for the fish and/or improved immunostimulant ingredients in the feed.

Administering the composition led to a better growth rate and a better feed intake. 100 and 200 milligrams/kilogram bodyweight per day doses were administered. As shown in this trial, the response of the fish to the composition was significantly better compared to the control group without the composition and/or combination. This conclusion emphasized the efficacy and the advantage of the composition and/or combination as an effective feed additive in aquatic animals such as fish.

Treatment (A) had the lowest significant FCR value among the 3 treatments (FIGS. 17-18). This demonstrated the advantage of the composition and/or combination as an advanced performer, improving the feed intake ability of the fish. This ability to lower the FCR value is a major factor in aquaculture management. The feeding cost is often the highest cost for fish and shrimp farmers.

Figure 25A:
FIGS. 25A-25C are photographs of the experimental set-up for the hybrid tilapia trial of FIG. 14.
Figure 25B:
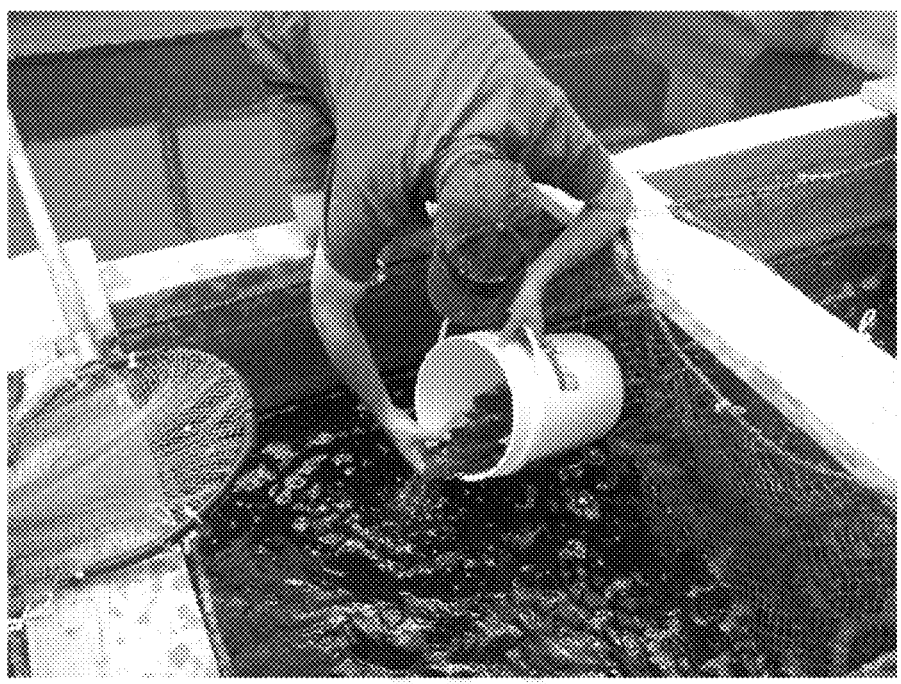
Figure 25C:
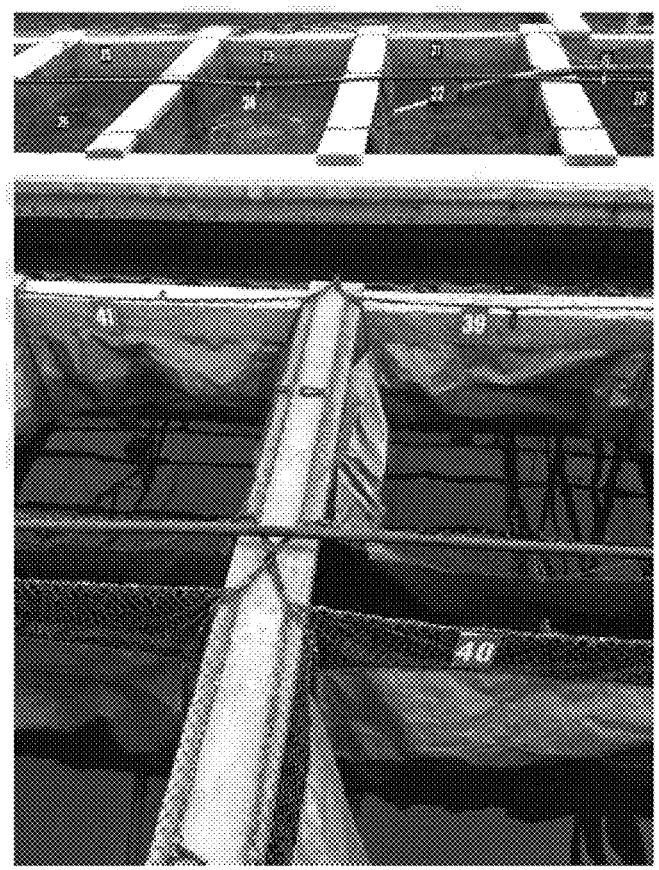

The environmental conditions of the experiment in terms of water temperature, dissolved oxygen levels and water quality were optimal for rearing tilapia. The growth rates of all the 3 groups were better when compared to the expected growth rate of tilapia, emphasizing the optimal conditions of the trial (FIGS. 19-24). The high percentage of survival (100%) in all 3 groups in this study also emphasized the optimum conditions during the trial. The lower temperature at the end of the trial affected the optimal growth rate of the fish but still the advantages of the composition and/or combination were evident. FIGS. 25A-25C show the experimental setup.

Example 3

A. Methods

In this example, the composition and/or combination was administered as a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans. The composition was used as a feed additive for carp. Juveniles of Common carp (*Cyprinus carpio*) were stocked in 18 cages in the experimental station. The total volume of the experimental system was 600 cubic meters. Each cage of 1 cubic meter in volume with a 25 millimeter mesh net was stocked with 35 fish at an average weight of 160 grams. The water source was from a well at a stable temperature of 24° C. The duration of the experiment was 83 days.

The experimental protocol included continuous assessment for the presence of diseases causing organisms. Growth performance parameters of the fish were recorded regularly. The daily/weekly assessment of water quality parameters included ammonia, nitrite, pH, temperature and dissolved oxygen.

Feeding rate was based on the recommended commercial feeding chart of Phibro Aqua and adjusted according to the size of the fish and the water temperature (FIG. 33). Feeding was performed manually twice a day. The feeding quantity for each cage was adjusted after evaluating the average weight of the fish in each cage every two weeks.

The composition was top-coated on the pellets using 2 wt % soy oil as the adhesive agent. The control group was given the same feed coated with 2 wt % soy oil. The feed for the trial was prepared by mixing the weighted feed in a mixer for 5 minutes with 2 wt % soy oil, and then additional 5 minutes mixing with the composition. In this trial 2 different doses of the composition and/or combination in the feed were compared: 100 mg per kg of body weight per day; and 200 mg per kg of body weight per day.

Replicates of 6 cages were used per treatment, which were divided equally in the rearing system. The feed for this trial was manufactured by Zemach Feed Mill. The feed is based on floating extruded pellets #4212 at size of 4 millimeters; containing 30.0% protein, 5.0% fat, 4.5% carbohydrates, 8.0% ash and 10.0% moisture.

B. Results

General Health Parameters:

1. Survival rate in all the cages for all the treatments were excellent, without mortality.

2. External parasites (*Gyrodectylus* and *Dactylogyrus*) were detected at low incidence. The fish were treated with formalin 37% and Bromex solution (50% Naled).

3. The general health condition as indicated by the vitality and the response to the feeding was very good for all treatments for the entire trial.

Figure 26:
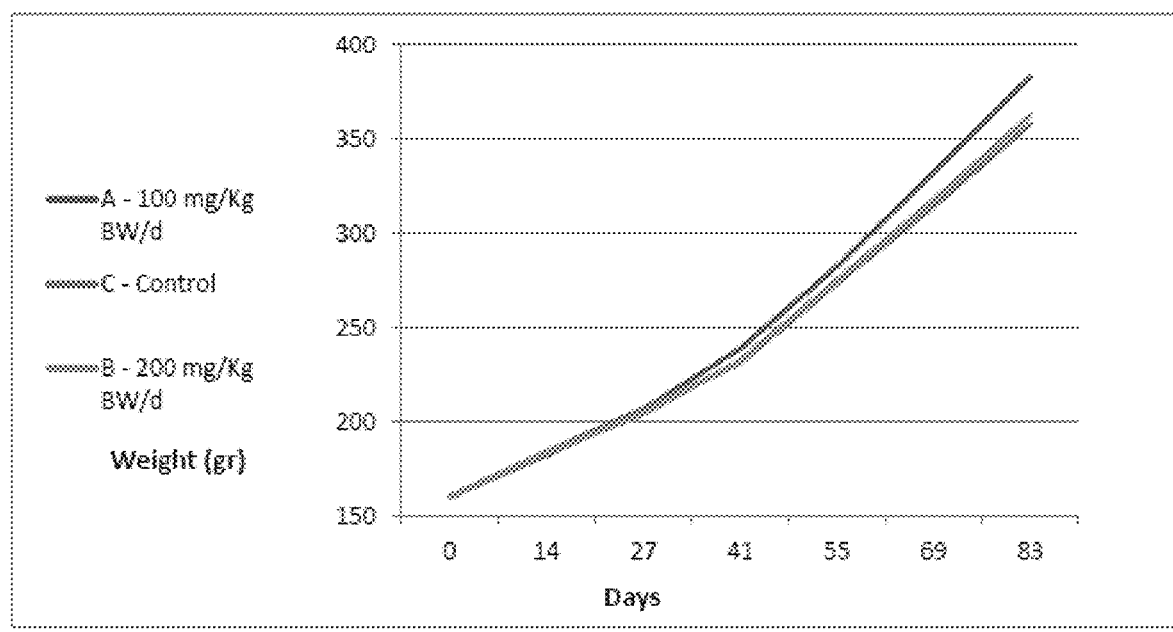
FIG. 26 is a graph of weight (g) versus days, illustrating the growth rate of common carp using two feed groups with different doses of the composition and/or combination and a control group.
Figure 32:
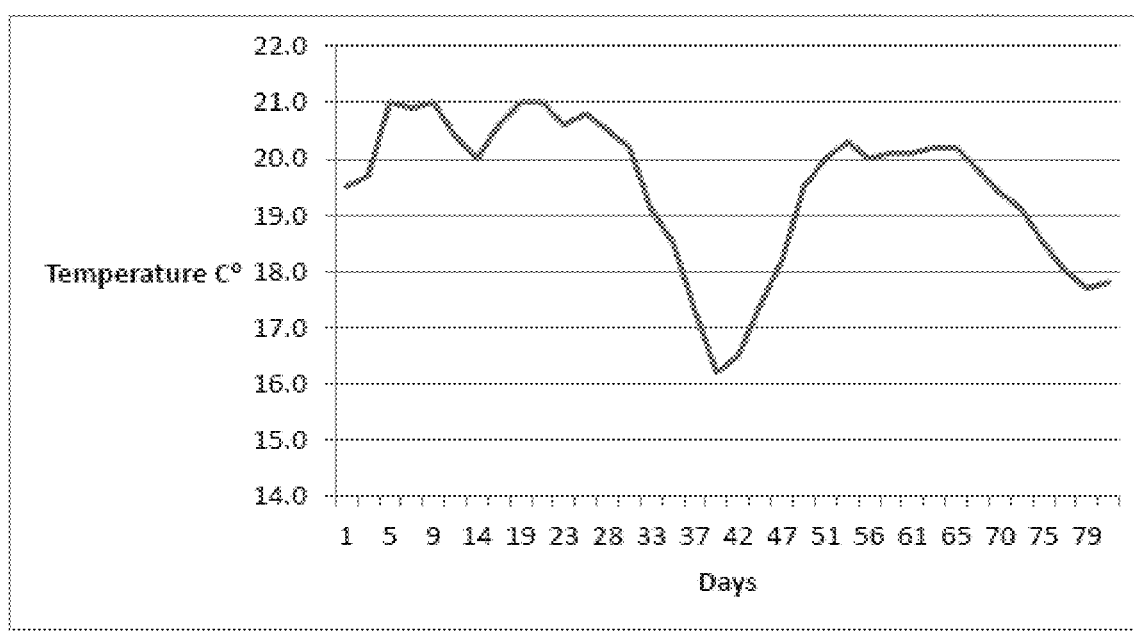
FIG. 32 is a graph providing the water temperature during the common carp trial of FIG. 26.

A significant higher growth rate of the fish fed with dose (A), using 100 milligrams of the composition per kilogram of bodyweight per day was obtained in this trial. A better growth rate in treatment (A) was observed by day 41. This difference became statistically significant by day 83 (FIGS. 26-28). Without being bound to a particular theory, the better growth rate may be due to an improved nutrition for the fish and/or improved immunostimulant ingredients in the feed.

Administering the composition led to a better growth rate and a better feed intake. 100 and 200 milligram/kilogram bodyweight per day doses were administered. As shown in this trial, the response of the fish to the composition was significantly better compared to the control group without the composition and/or combination. This conclusion emphasized the efficacy and the advantage of the composition and/or combination as an effective feed additive in animals like fish.

Treatment (A) had the lowest (insignificant) FCR value among the 3 treatments (FIGS. 29 and 30). This demonstrated the advantage of the composition and/or combination as an advanced performer, improving the feed intake ability of the fish. This ability to lower the FCR value is a major factor in aquaculture management. The feeding cost is often the highest cost for fish and shrimp farmers.

Figure 37A:
FIGS. 37A-37C are photographs of the experimental set-up for the common carp trial of FIG. 26.
Figure 37B:
Figure 37C:
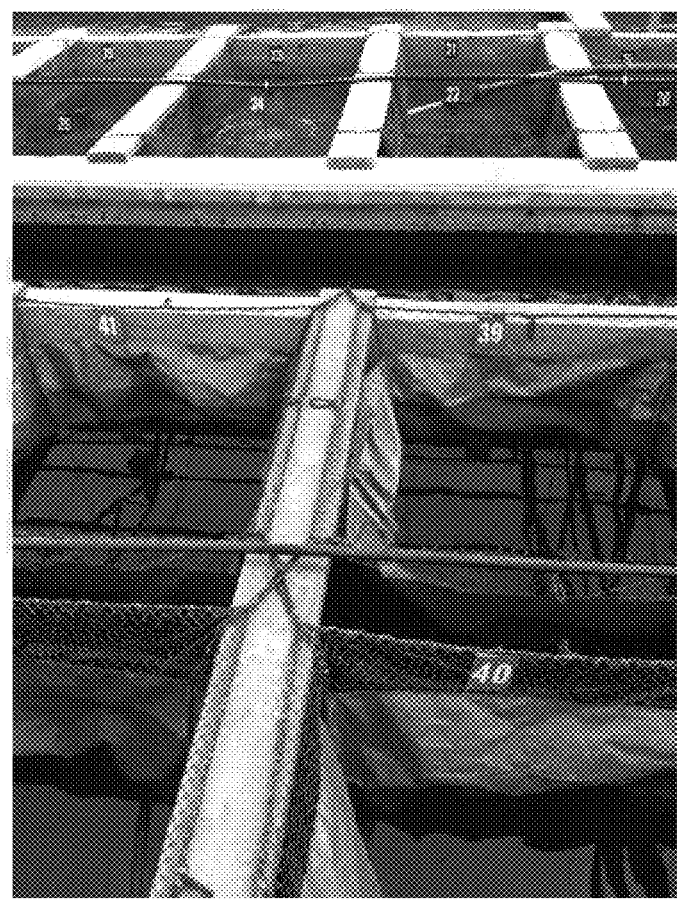
Figure 38:
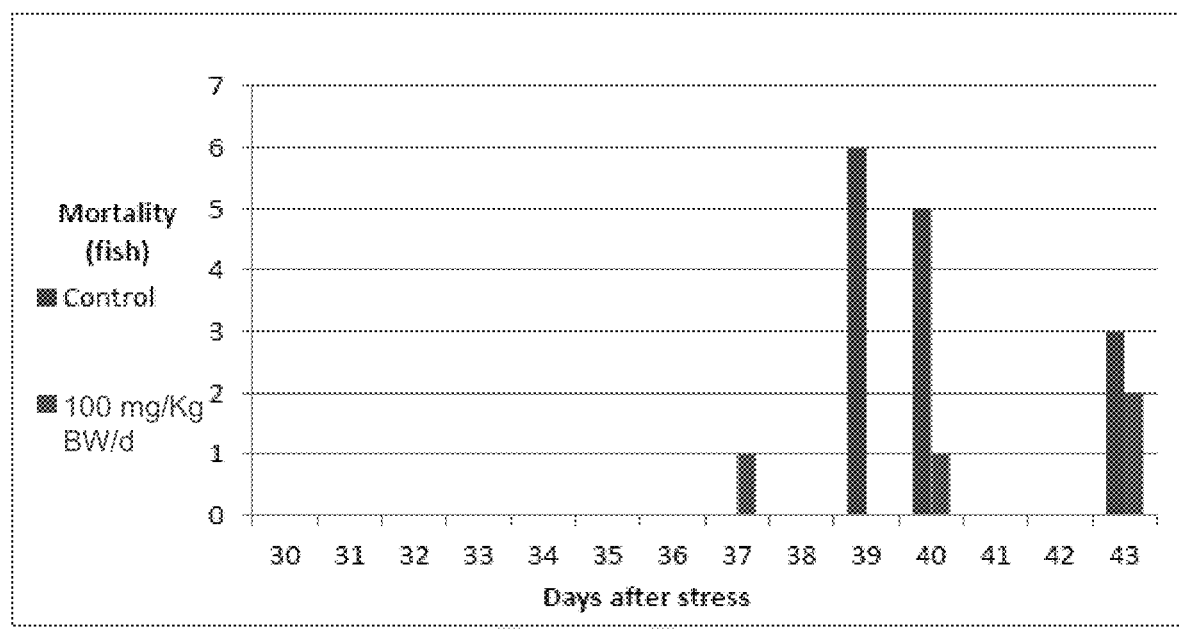
FIG. 38 is a graph of mortality versus days after stress, comparing the daily mortality of tilapia fed with the composition and/or combination and the control group.
Figure 39:
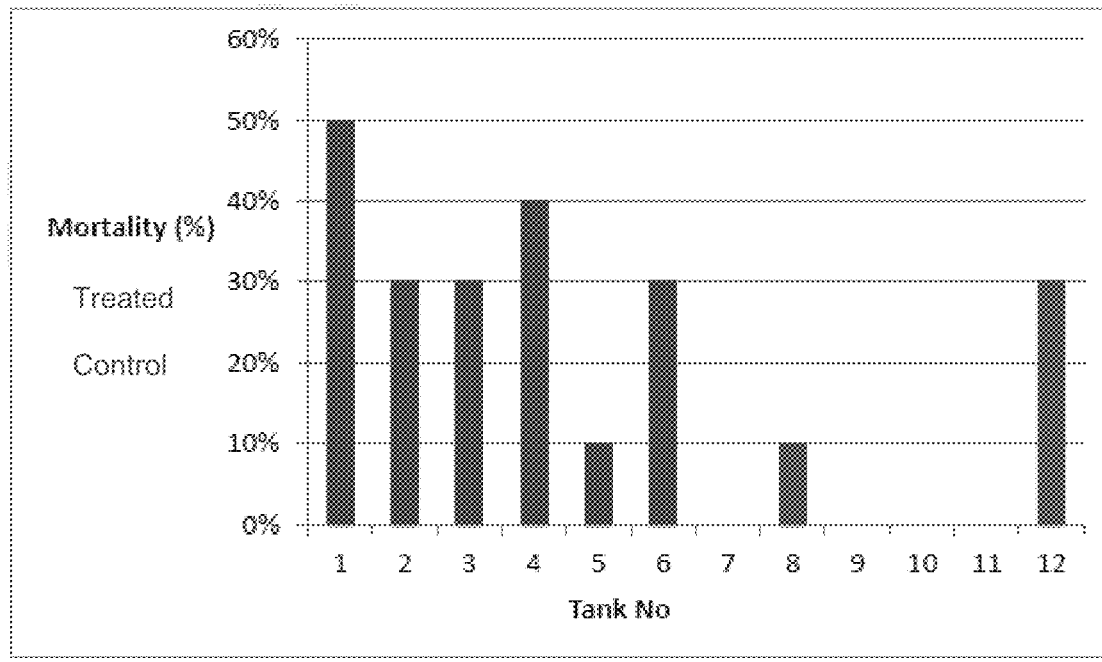
FIG. 39 is a graph of mortality (%) versus tank number, comparing the total mortality of tilapia per tank of tilapia fed with the composition and/or combination and the control group during the tilapia trial of FIG. 38.
Figure 40:
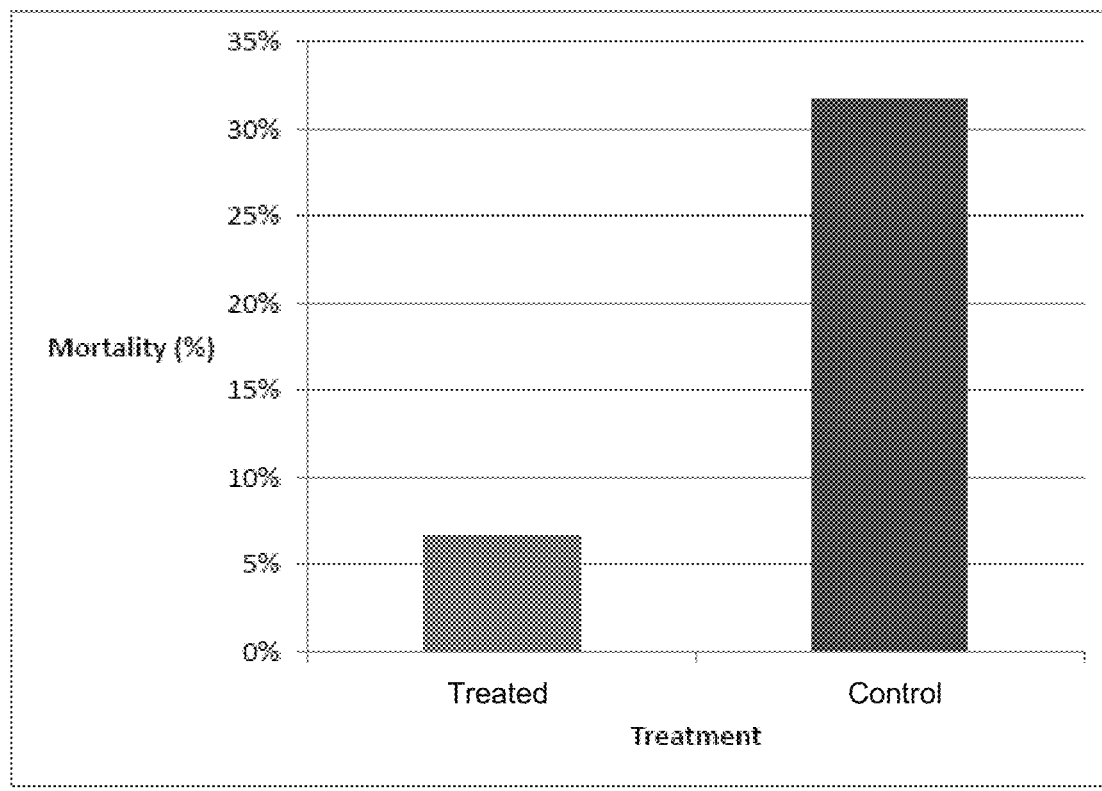
FIG. 40 is a bar graph illustrating the total mortality of tilapia separated by treatment during the tilapia trial of FIG. 38.
Figure 43:
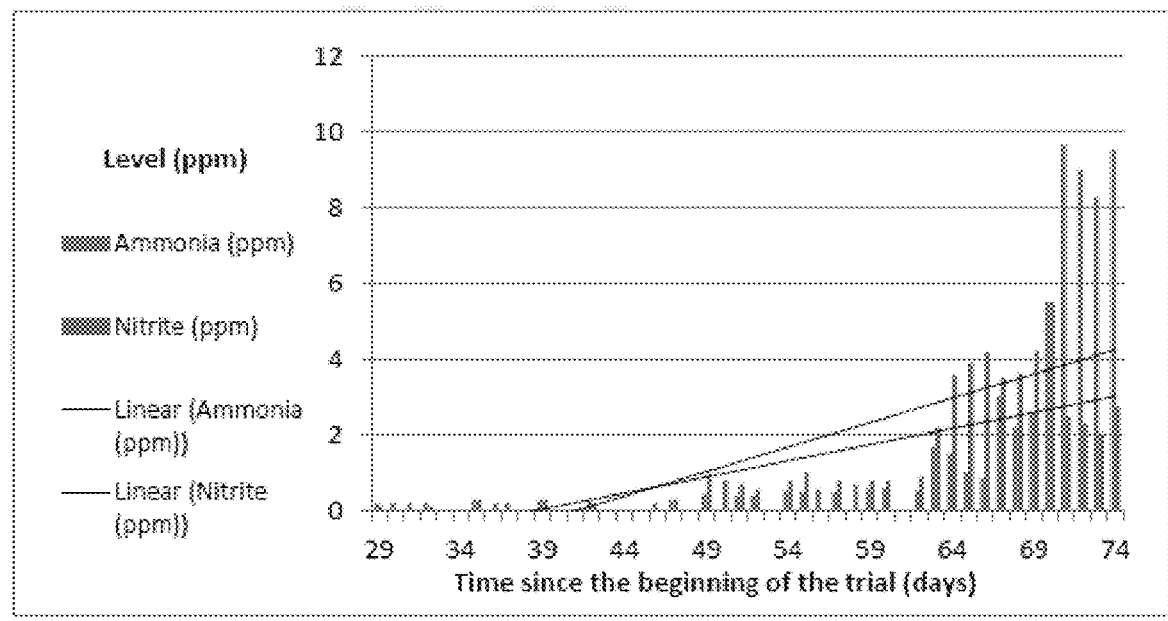
FIG. 43 is a graph of level (ppm) versus time (days), illustrating ammonia and nitrite levels in the water during the tilapia trial of FIG. 38.
Figure 44:
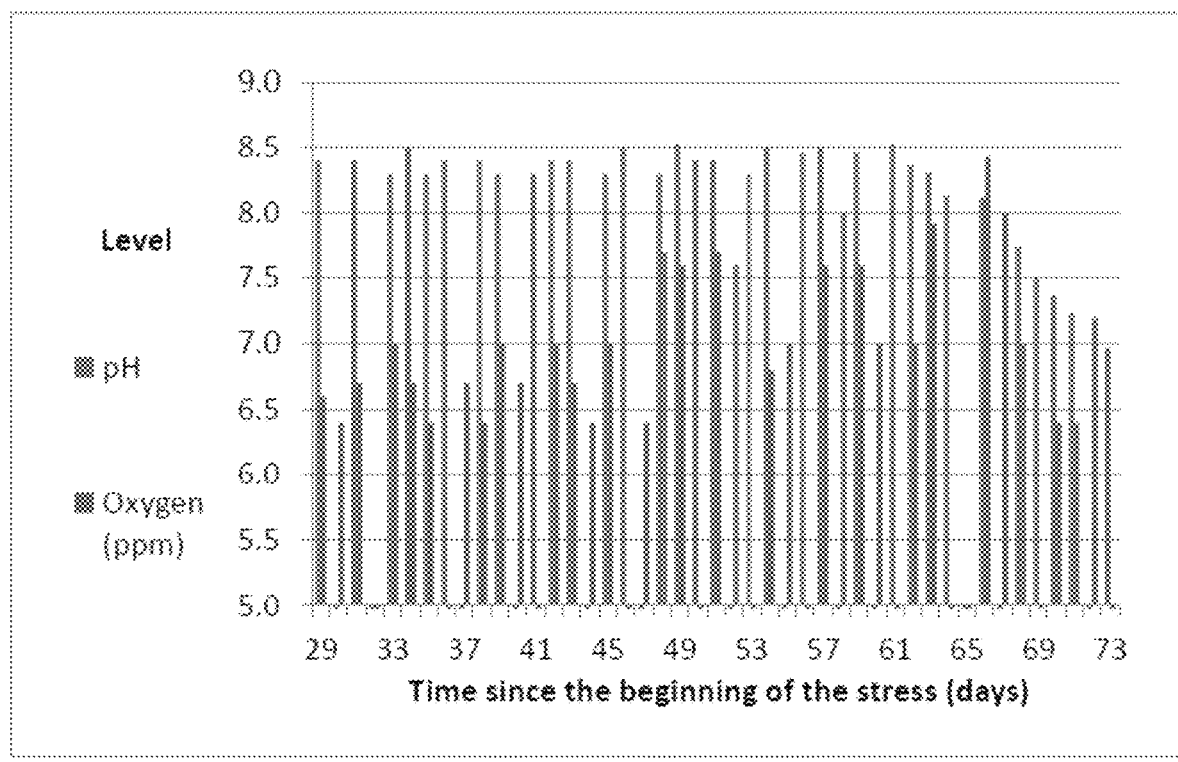
FIG. 44 is a graph of level versus time (days), illustrating pH and oxygen (ppm) levels in the water during the tilapia trial of FIG. 38.
Figures 45, 46:
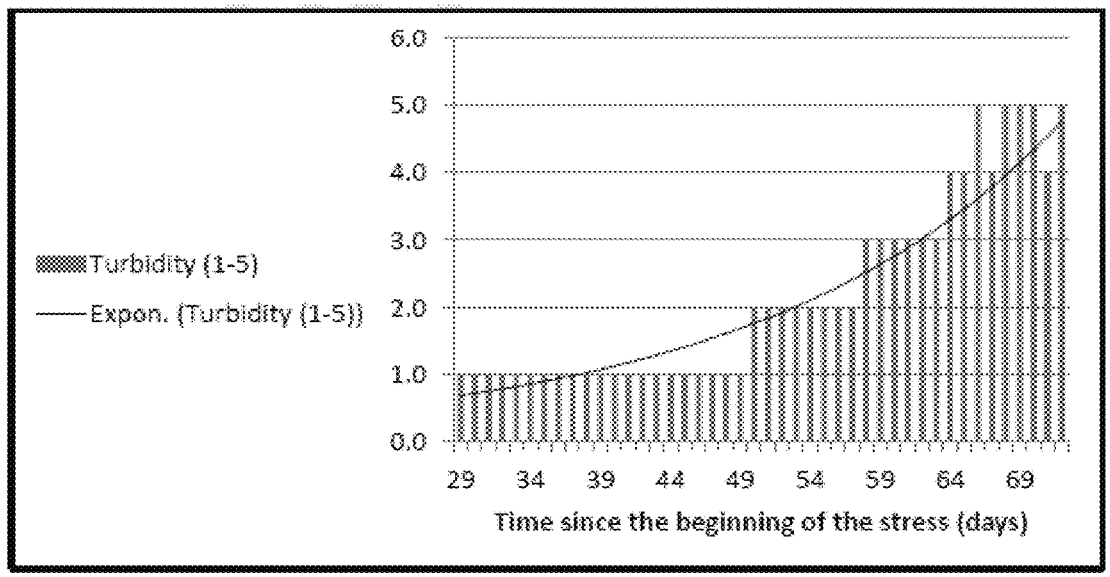
FIG. 45 is a graph of turbidity versus time (days) illustrating the water turbidity during the tilapia trial of FIG. 38.
FIG. 46 is a table listing the toxicity of ammonia ($NH_3$) in multiplication factors.
Figures 48, 49A:
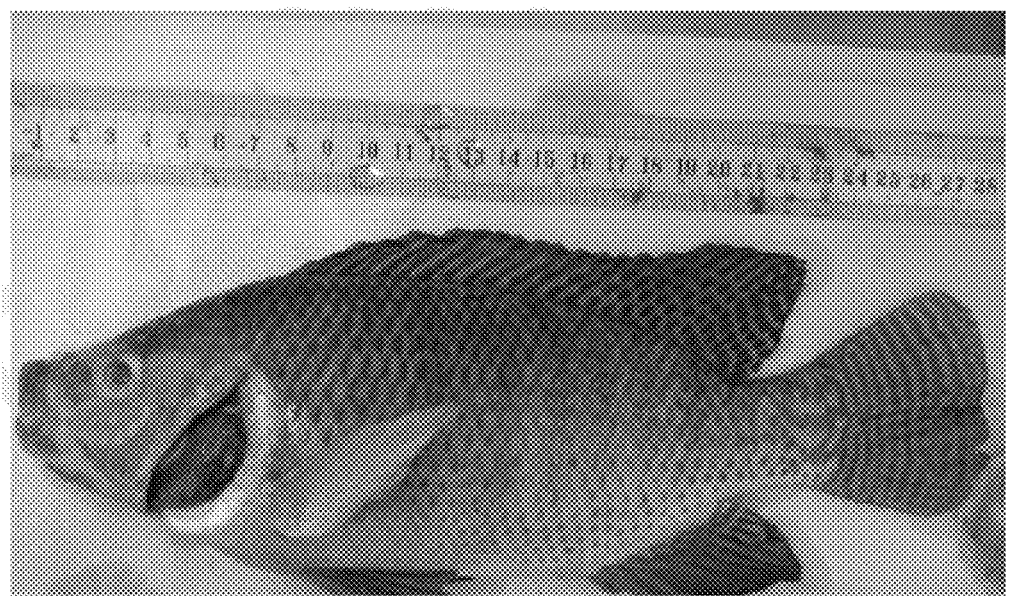
FIG. 48 is a table providing the mortality per cage by date during the tilapia trial of FIG. 38.
FIGS. 49A-49C are photographs of exemplary tilapia from the trial of FIG. 38.
Figure 49B:
Figure 49C:

The temperatures of the experiment demonstrated a cold water environment (16-21° C.). This range of temperatures is common in carp culture worldwide. These low temperatures affected the optimal growth rate of the fish but still the advantages of the composition and/or combination were evident. The water conditions in terms of dissolved oxygen levels, ammonia, nitrite and pH were optimal for rearing carp. The high percentage of survival (100%) in all 3 groups in this study emphasized the optimum conditions during the trial (FIGS. 31-36). FIGS. 37A-37C show the experimental setup.

Example 4

A. Background

In this example, the composition and/or combination was administered as a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans. The composition was used as an immune modulator for hybrid tilapia. Ammonia is a toxic compound that can adversely affect fish health. The nature and degree of toxicity depends on many factors, including the chemical form of ammonia, the pH and temperature of the water, the length of exposure, and the life stage of the exposed fish. In natural surface waters, ammonia occurs in two forms: ionized ammonia, $NH_4^+$, and un-ionized ammonia, $NH_3$. In fish, ammonia is a byproduct of protein metabolism and is primarily excreted across the gill membranes, with a small amount excreted in the urine. Ammonia's toxicity is principally due to the un-ionized form, $NH_3$. As pH increases, the toxicity of ammonia rises because the relative proportion of unionized ammonia increases. The toxicity of ammonia may cause convulsions, coma and death. Without being bound to a particular theory, elevated $NH_4^+$ in the fish body may displace $K^+$ and depolarize neurons, causing activation of glutamate receptor, which leads to an influx of excessive $Ca^{2+}$ and subsequent cell death in the central nervous system. In the case of larvae of common carp, acute toxicity of 1.76 parts per million of $NH_3$ caused 50% mortality in the group after 24 hours. Chronic effects of ammonia were studied in three batches of turbot (*Scophthalmus maximus*) juveniles (14, 23 and 104 grams) exposed for 4-6 weeks to constant ammonium chloride solutions. Under the environmental conditions used (16.5-47.5° C., pH 7.92-8.03, salinity 34.5 parts per thousand, over 80% oxygen saturation), no mortalities occurred up to 0.4 parts per million unionized ammonia. In adapted small turbot, no major physiological disturbances were observed up to 0.4-0.5 parts per million, while large turbot were more sensitive to ammonia.

The ability to improve the resistance of aquatic species to the toxicity of the ammonia has been investigated. Tiger shrimp (*Penaeus monodon*), 5-day post larvae, were fed diets supplemented with 0 and 71.5 parts per million astaxanthin for 8 weeks. Shrimp were then subjected to 72 hours exposure of ammonia at 0.02, 0.2, 2 and 20 parts per million. The survival rates of the astaxanthin-fed shrimp were higher than those of the control shrimp under all levels of ammonia except 20 ppm, showing that the shrimp's resistance to ammonia stress had been improved by dietary astaxanthin. Other research has investigated the effects of dietary mannans oligosaccharide (MOS) on growth performance, gut morphology, and $NH_3$ stress tolerance of Pacific white shrimp *Litopenaeus vannamei*. After $NH_3$ stress for 24 hours, survival rates of shrimp fed 2.0, 4.0, 6.0 and 8.0 grams/kilogram MOS-supplemented diets were significantly higher ($P<0.05$) than that of shrimp fed a control diet.

The purpose of this study was to evaluate the effect of the composition and/or combination on the fish resistance to the stressful condition of toxic ammonia levels in the water.

B. Methods

Hybrid tilapia (*Oreochromis niloticus* X *O. aureus*) were stocked in 12 tanks in the experimental station. Each tank of 230 liter in volume was stocked with 10 fish with an average weight of 350 grams per fish. The water source was from a well with a constant water temperature of 22° C. and constant salinity of 1,300 milligrams chloride. The duration of the experiment was 74 days. During the first phase, 6 tanks were fed 100 milligrams of the composition and/or combination per kilogram of bodyweight per day, while the other 6 tanks were fed with commercial feed without supplement. After 30 days of feeding in optimal conditions of water, the water inlet was reduced, allowing the water quality to deteriorate for an additional 30 days. In the third phase of 14 days the water inlet was closed completely and ammonium chloride ($NH_4Cl$) was added to each tank on a daily basis. This phase was characterized by a continuous mortality of the fish showing clinical symptoms of ammonia toxicity and bacterial infections associated with poor water quality.

The experimental protocol included continuous assessment for the presence of diseases causing organisms. The daily assessment of water quality parameters included ammonia, nitrite, pH, water temperature and dissolved oxygen.

Feeding rate was 1% of bodyweight, based on the recommended commercial feeding chart of Phibro Aqua and was adjusted according to the water temperature and the response of the fish (FIG. 21). Feeding was performed manually twice a day. The composition was top-coated on the pellets using 2 wt % soy oil as the adhesive agent. The control group was given the same commercial feed coated with 2 wt % soy oil, but without the composition. The feed for the trial was prepared by mixing the weighted feed in a mixer for 5 minutes with 2 wt % soy oil, and then additional 5 minutes mixing with the composition. The feed for this trial was manufactured by Zemach Feed Mill. The feed is based on floating extruded 4 mm pellets, #4662; containing 35.0% protein, 3.5% fat, 14.0% carbohydrates, 8.0% ash and 10.0% moisture.

C. Results

General Health Parameters:

1. At the third phase (14 days) the fish didn't respond to the feed.

2. The moribund and the dead fish that were collected during the trial had typical clinical symptoms of toxicity of ammonia.

The results of this trial showed a significant higher resistant fish fed a diet with the composition and/or combination at a dose of 100 mg/kg of body weight per day compared to the control without the composition and/or combination (FIGS. 38-41). In this trial, the moribund and the dead fish that were collected during the trial had typical clinical symptoms of ammonia toxicity, including convulsions, gill necrosis, coma, and death.

Poor water quality suppresses the immune system of the fish, enabling parasites and bacteria to enter the fish body, causing disease outbreak and consequently mortality. In the experiment, the clean water inlet flow was reduced to cause deterioration of the water quality, which finally resulted in death in the most stressed and frail fish in this trial (FIGS. 42-49D).

Figure 50A:
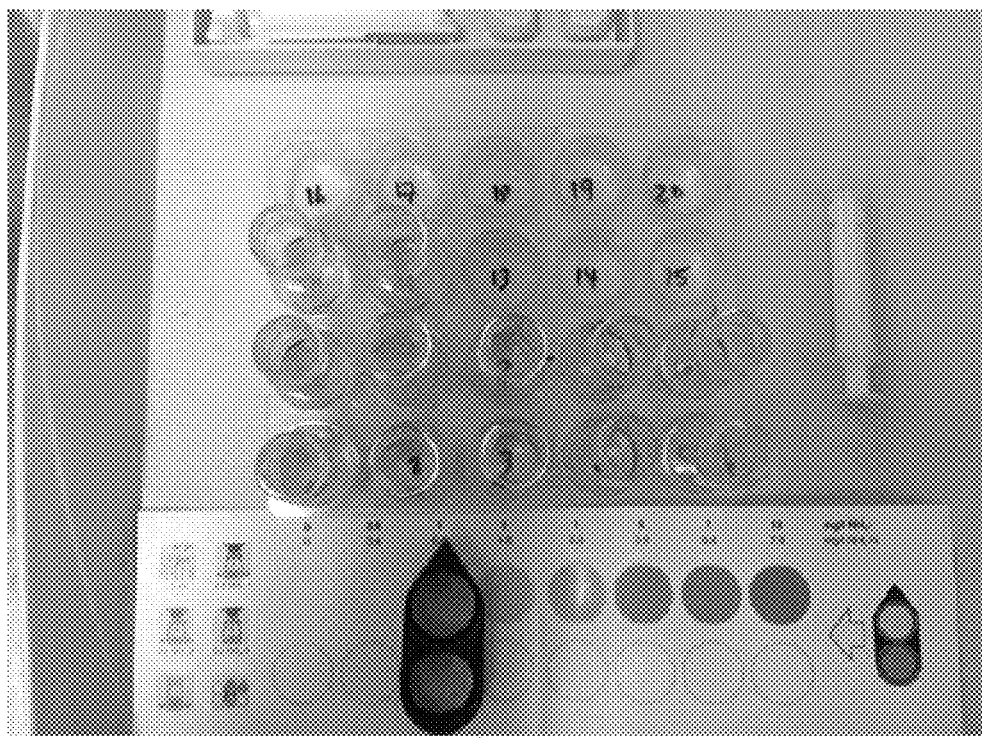
FIGS. 50A and 50B are photographs showing the experimental set up of the tilapia trial of FIG. 38.
Figure 50B:

Feeding tilapia with the composition and/or combination at a dose of 100 milligrams/kilogram of body weight per day for 30 days period significantly improved their resistance and survival under poor water conditions such as high levels of ammonia and nitrite. FIGS. 50A and 50B show details of the experimental setup.

Example 5

The Composition and/or Combination as an Immune Modulator on the Survival and the Overall Health Status of the Pacific White Shrimp (*Litopenaeus vannamei*)

Materials and Methods
General Design of the Clinical Field Study 2,400 Postlarva-20 days of *Litopenaeus vannamei* were stocked in 12 tanks in the experimental station. Each tank of 500 liter in volume was stocked with 200 PL-20, at an estimated weight of 0.15 g per postlarvae. The experimental unit included a central collecting tank and a central biofilter. The water source was from a well. Balance marine salt was added to the water to achieve a total salinity of 10 ppt (parts per thousand). The duration of the experiment was 71 days. The average size of the shrimp at the end of the trial was around 10 grams.
Diet Supplemented with the Disclosed Composition and/or Combination In this trial, the composition and/or combination was administered as a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans. 2 different doses of the composition were compared to a control. 4 tanks were fed 100 mg of the composition per kg of BW per day, 4 tanks were fed 200 mg of the composition per kg of BW per day, while the other 4 tanks were fed with commercial feed without supplement.

Figure 53:
FIG. 53 is a photograph of the experimental setup for the experiment of FIG. 51.
Figure 54:
FIG. 54 is a photograph showing exemplary shrimp at the end of the experiment of FIG. 51.

Feeding rate based on the recommended feeding chart of Phibro Aqua for Shrimp. Feed quantity was adjusted according to the water temperature, the response of the shrimp and the estimation of their average weight. Feeding was performed manually twice a day. The composition was top-coated on the pellets using 2% of Soy oil as the adhesive agent. The control group was given the same feed without supplement coated with 2% Soy oil. The feed for the trial was prepared by mixing the weighted feed in a cement mixer (maximum load of 50 kg) for 5 minutes with 2% Soy oil, and then additional 5 minutes mixing with the supplement.
General Conditions The experimental protocol included continuous assessment for the presence of diseases causing organisms. The daily assessment of water quality parameters included total salinity, ammonia, nitrite, pH, water temperature and dissolved oxygen.
Results The results illustrate that a significantly greater percentage of the shrimp that were fed the supplement survived, compared to the control group (FIG. 51). FIG. 52 provides the water quality in the experiment. The conditions of the trial were excellent for growing shrimp. Shrimp had good body condition and good coloration. No external parasites were detected. The final average weight of the shrimp was around 10 grams, normal for in-door culture. At this stage (nursery), the survival rates of the control groups (60%) are normal. FIG. 53 shows the experimental setup, and FIG. 54 shows shrimp at the end of the trial.

In a different trial, 2500 shrimp in a pond were administered a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans. After 6 months, the shrimp were compared to 2500 control shrimp in a separate pond that were not administered the composition. The composition-fed shrimp has an 86% survival rate, compared to 22% for the control shrimp, and also had a greater yield (kg/pond) than the control shrimp.

Example 6

The Composition and/or Combination Increased Weight Gain in Shrimp

A composition comprising silica, mineral clay, yeast cell wall extract, and β-1,3 (4)-endoglucanohydrolase was fed to 2500 shrimp in an amount of 0.2% by weight of feed over 4 months. A control group of 2500 shrimp was fed only shrimp food, but kept under the same conditions. 100 shrimp from each group were randomly removed each month and weighed, then returned to the group. The results indicated that the group that was administered the composition in addition to feed grew larger over the four months of the test (Table 1).

TABLE 1

| | Control Group | Composition Group |
|---|---|---|
| Average shrimp weight after 1 month | 0.333 g | 0.282 g |
| Average shrimp weight after 2 month | 0.8 g | 0.68 g |
| Average shrimp weight after 3 month | 1.75 g | 2.98 g |
| Average shrimp weight after 4 month | 5.19 g | 7.70 g |

Figure 55:
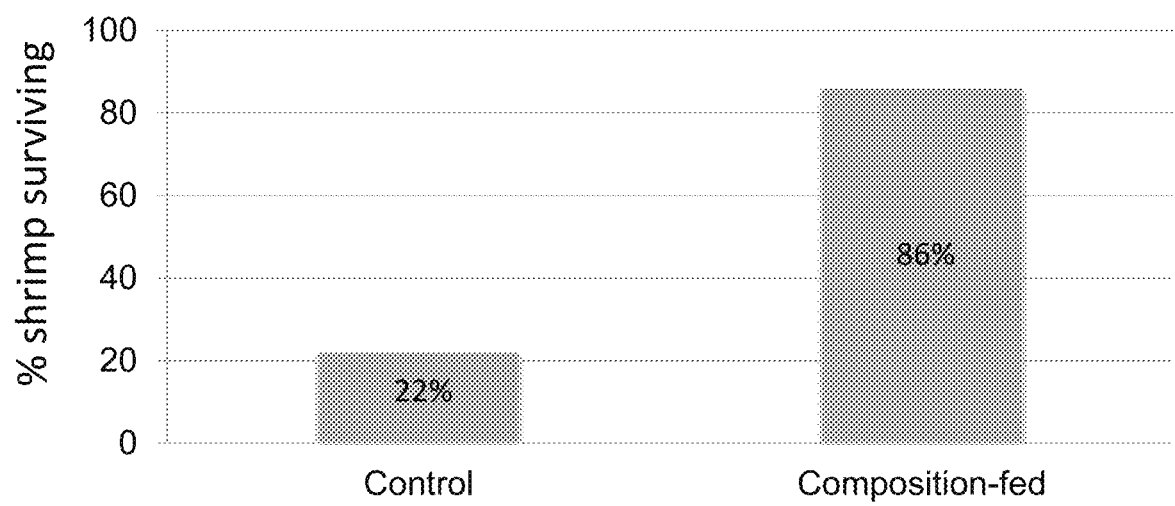
FIG. 55 is a plot of percentage shrimp survival versus treatment, illustrating the four-fold increase in shrimp survival in shrimp fed an exemplary embodiment of the disclosed composition.
Figure 56:
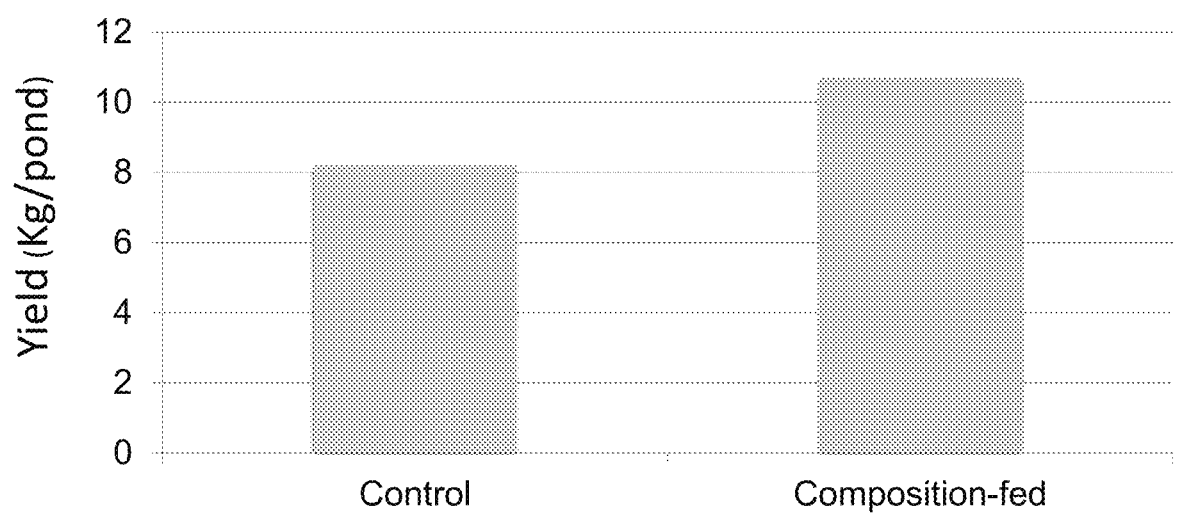
FIG. 56 is a plot of yield in kg per pond versus treatment, illustrating the increase in shrimp yield in shrimp fed an exemplary embodiment of the disclosed composition.

In a second study, shrimp fed the same composition over 6 months demonstrated a four-fold increase survival rate (FIG. 55) and an increase in the shrimp yield per pond (FIG. 56).

Example 7

The Effect of the Composition and/or Combination on the Growth Performance, Immune Response and Overall Health Status of Nile Tilapia (*Oreochromis niloticus*) Challenged by *Streptococcus agalactiae*

Objective

The objective of this trial is to investigate the effect of the disclosed composition and/or combination on Tilapia, by comparing between groups of fish fed with the composition and/or combination and control groups of fish with no additive in their diet. In this trial, the composition and/or combination is administered as a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans.

Trial Design

General design—this trial is divided to two phases. In the first phase, the treated fish are fed one embodiment of the disclosed composition and/or combination for a period of 90 days, while the control groups receive no additive in the diet. The growth performance parameters that are compared in this phase are: survival, growth rate, FCR and general health status.

In the second phase, the fish are challenged with *S. agalactiae*, generating LD50-70 in the groups. The parameters that are detected in this phase will indicate the immune response. This phase will be completed after 3 continuous days with no mortality in any group.

Fish— the fish used in the trail are Nile tilapia (*Oreochromis niloticus*). The initial average weight of the fish is 20-100 g. The fish are naive for *S. agalactiae*. The fish are checked for health and presence of parasite before the trial. Only healthy fish are used for the trial. All the groups are acclimated for 2 weeks in the testing unit before the trial and are treated if necessary.

Testing Unit and Water Condition— the testing unit is based on tanks or cages. The trial includes 5-6 replicates per treatment. Each unit includes at least 30 fish per unit. Water conditions are in the optimal range for Tilapia culture: maximum salinity of 2 ppt, temperature range of 27–30° C., oxygen level higher than 6 ppt, and a pH of 7-8.

Weighing and Feeding— weighing is done every 2 weeks. All the fish in the tank/cage are sampled. The feeding rate and the size of the pellets are adjusted based on the average weight and the recommended feeding amounts of the composition and/or combination. The feed is served to the fish 2-3 times a day. The amount of the composition and/or combination that is added to the feed is based on the recommended inclusion rate. It is added to the feed by top-coating with 2% of oil or by integrating it into the feed in the pelleting phase.

Monitoring— water quality is measured daily for oxygen and temperature and weekly for ammonia and nitrite. And the water is analyzed for external parasites every 2 weeks.

Immune Response— at the end of the trial the following parameters are measured:

1. Blood count and non-specific immune response—erythrocyte (RBC), leukocyte (WBC), hematocrit (Hct), haemoglobin (Hb) amount, leukocyte cell types (percentage of lymphocyte, monocyte, neutrophil, eosinophil) blood cell sizes, and the values of phagocytic activities and erythrocyte cell indexes (MCV and MCH) are measured.

2. Liver health—determined by comparing the size and the color of the liver of 5 fish per tank/cage. The livers pathology is also analyzed by comparing the health status by using histology slides; and 3. Gene expression—selected genes for immune response are analyzed in this study. The gene expression is determined at the end of the trial by comparing the treated and the non-treated fish.

Example 8

The Effect of Composition and/or Combination on the Growth Performance and the Overall Health Status of Tilapia (*Oreochromis* Spp.) Compared to its Main Ingredients (β-Glucans and Mannans, Silica and Clay)

Objective

The objective of this trial is to investigate the effect of the disclosed composition and/or combination on Tilapia, by comparing between groups of fish fed with the composition and/or combination, β-glucans and mannans, silica, clay and a control group of fish with no additive in their diet. In this trial, the composition and/or combination is administered as a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans.

The parameters that are collected in this trial includes: growth rate, survival, FCR (feed conversion ratio), blood count and liver health.

Materials and Methods

Testing Unit and Water Condition— the testing unit is based on tanks or cages. The trial includes 5-6 replicates per treatment, and a total of 25-30 units for the entire trial. Each unit will include at least 30 fish per unit. Water conditions are in the optimal range for Tilapia culture, i.e., maximum salinity of 2 ppt, temperature range of 27–30° C., oxygen level higher than 6 ppt, and a pH of 7-8.

Treatment Groups— the trial includes 4 treatments with different feed additives and one control group with no additive in the diet. The treatments and the inclusion rates will be:

1. the composition and/or combination at inclusion rate of 5 g/kg feed;
2. β-glucans and mannans at an inclusion rate of 1 g/kg feed;
3. silicon dioxide at an inclusion rate of 2 g/kg feed;
4. clay at an inclusion rate of 3.5 g/kg feed; and
5. control with no additive.

Feed Preparation and Feeding— the additives are added to the feed by top-coating with 2% of soy oil or by integrating it into the feed in the pelleting phase. The feed for the trial is based on standard commercial feed for Tilapia. The control group is fed the same feed with an additional of 2% of soy oil by top-coating. The feed is served to the fish 2-3 times a day.

Fish— fish are Tilapia (*Oreochromis* spp.). The initial average weight of the fish is 20-100 g. The fish are checked for health and presence of parasites before the trial. Only healthy fish are used for this trial. All the groups are acclimated for 2 weeks in the testing unit before the trial and are treated if necessary.

Weighing— weighing is done every 2 weeks. All the fish in the tank/cage are sampled. The feeding rate and the size of the pellets are adjusted based on the average weight and the recommended feeding amounts for the composition and/or combination.

Monitoring— water quality is measured daily for oxygen and temperature and weekly for ammonia and nitrite. And the water is analyzed for external parasites every 2 weeks.

Non-Specific Immune Response— at the end of the trial, the following parameters will be measured:

1. Blood count—erythrocyte (RBC), leukocyte (WBC), hematocrit (Hct), haemoglobin (Hb) amount, leukocyte cell types (percentage of lymphocyte, monocyte, neutrophil, eosinophil) blood cell sizes.

2. Liver health—determined by comparing the size and the color of the liver of 5 fish per tank/cage. The livers pathology is also analyzed by comparing the health status by using histology slides.

Example 9

The Effects of the Composition and/or Combination on Shrimp Health and Survival and Challenged with a Known Pathogen Experimental Design
Experimental Feed The disclosed composition and/or combination is incorporated into the feed (e.g. Rangen shrimp feed) at an inclusion rate of from 0.2% to 0.5% or more, depending on shrimp size. In this trial, the composition and/or combination is administered as a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans.

Methodology

After an acclimation period to experimental conditions, the embodiment of the composition and/or combination is provided to five replicate tanks at 3% of biomass per day divided in two rations. During the feeding period, the control treatment has ten aquaria, but subsequently they are divided into positive (infected) and negative (non-infected) control treatments. The feed for the control is a re-pelleted commercial feed with no additive throughout the trial. The shrimp are weighed before and after the feeding period. After a 21 day feeding period the shrimp are challenged with a defined disease (e.g. white spot syndrome (WSS) or acute hepatopancreatic necrosis disease (AHPND)) following laboratory standardized protocols. Mortality is counted every day for the next 14 days, and survival shrimps are counted at the end of this period. FIG. 57 provides a proposed timeline for the trial. Tissue samples of muscle, cephalothorax and haemocytes are taken at the beginning and end of the feeding period and at the end of the challenge period. Tissue is frozen in liquid nitrogen and stored at −80° C. for transcriptomic analysis if needed. Samples for histopathology analysis are taken during the challenge period as determined by lab pathologist. Parameters to be obtained include final weight, survival rate, histopathological score, and transcriptomic profiles.

Example 10

The Effect of the Composition and/or Combination on Growth and Survival of White Shrimp (*Litopenaeus vannamei*) Postlarvae Objective To determine the effect of the composition and/or combination on growth and survival of white shrimp (*Litopenaeus vannamei*) postlarvae rearing in laboratory conditions. In this trial, the composition and/or combination was administered as a composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannans.

This trial was conducted to determine whether one embodiment of the disclosed composition and/or combination had an effect on growth or/and survival. In the trial postlarvae 12 ($PL_{12}$) were used because $PL_{10-12}$ are the most common stage used for stocking into the growout ponds. The survival rate of PL during the first 30 days post-stocking is an important criteria in shrimp cultivation.

Experimental Animals

Pacific white shrimp postlarvae 9 ($PL_9$) were used in this study. A total of 1,000 $PL_9$ were used and acclimated in fiberglass tanks for 3 days. Later $PL_{12}$ were used for the trial. Total of 12 500-liter tanks were used for rearing $PL_{12}$ with seawater of 20-25 ppt. salinity. Temperature was maintained constantly at 29±1° C. by an aquarium heater. $PL_{12}$ were stocked at a density of 100 $PL/m^2$ or 50 shrimp/tank.

The two experimental groups consisted of a control group where the shrimp were fed commercial pelleted feed for white shrimp, and the treatment group there the shrimp were fed pelleted feed mixed with the composition and/or combination at an inclusion rate of 100 mg/kg of feed. Each group comprised six replicates.

Growth and Survival Study

Shrimp were fed four times daily at the satiation rate. Feeding was adjusted according to shrimp weight throughout the 45 day trial period. Water quality parameters, such as pH, dissolved oxygen (DO), alkalinity, ammonia and nitrate, were maintained at optimal levels for rearing shrimp and analyzed weekly throughout the trial. Survival rate was recorded every 10 days. Shrimp were weighed at 30 and 45 days. Feed conversion ratio (FCR) was determined at the end of the trial.

Results

Figure 59:
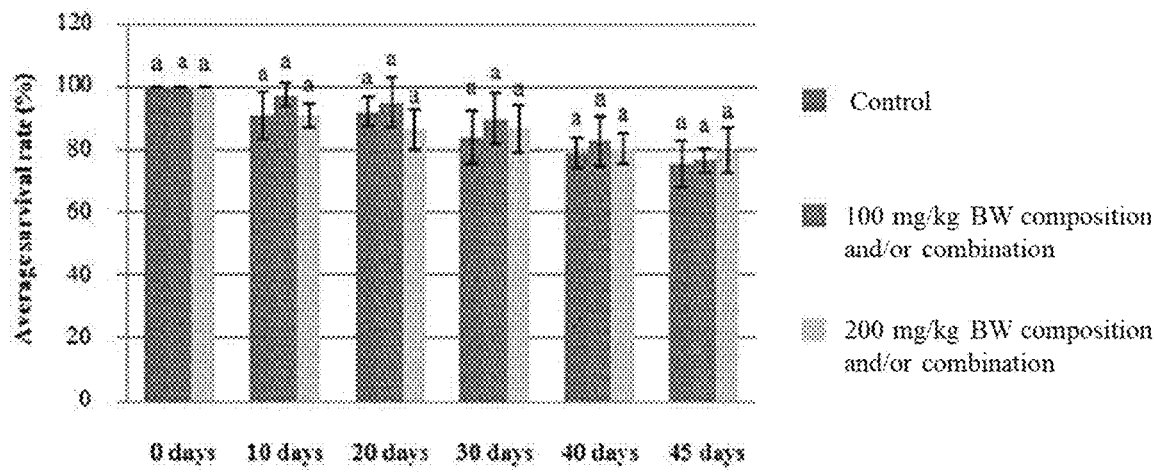
FIG. 59 is a graph of average survival rate versus time, illustrating the average survival of shrimp that are fed one embodiment of the disclosed composition and/or combination at different inclusion rates.

Table 2 and FIG. 59 provide the average survival rates of Pacific white shrimp from all groups. At 45 days feeding trial, the highest values were seen in the group fed with 200 mg/kg body weight (BW) of the composition and/or combination (79.67±7.09%), followed by the group fed with 100 mg/kg BW of the composition and/or combination (76.68±3.87%) and the lowest values were seen in the control group (75.50±7.42%).

TABLE 2

Average survival rates of Pacific white shrimp at day 0, 10, 20, 30, 40 and 45

| Treatment | Average survival rate (%) | | | | | |
|---|---|---|---|---|---|---|
| | Day 0 | Day 10 | Day 20 | Day 30 | Day 40 | Day 45 |
| Control | 100 | 90.85 ± 7.5$^a$ | 91.83 ± 4.7$^a$ | 84 ± 8.3$^a$ | 79 ± 4.9$^a$ | 75.5 ± 7.4$^a$ |
| 100 mg/kg BW Composition and/or combination | 100 | 97.06 ± 3.9$^a$ | 94.77 ± 7.7$^a$ | 89.67 ± 8.1$^a$ | 82.67 ± 7.8$^a$ | 76.68 ± 3.9$^a$ |

TABLE 2-continued

Average survival rates of Pacific white shrimp at day 0, 10, 20, 30, 40 and 45

| | Average survival rate (%) | | | | | |
|---|---|---|---|---|---|---|
| Treatment | Day 0 | Day 10 | Day 20 | Day 30 | Day 40 | Day 45 |
| 200 mg/kg BW Composition and/or combination | 100 | $90.85 \pm 3.9^a$ | $86.27 \pm 6.4^a$ | $86.67 \pm 7.5^a$ | $80.33 \pm 5^a$ | $79.67 \pm 7.1^a$ |

Data are presented as mean ± standard deviation. Means in the same column with different superscript are significantly different from each other ($p < 0.05$)

Figure 60:
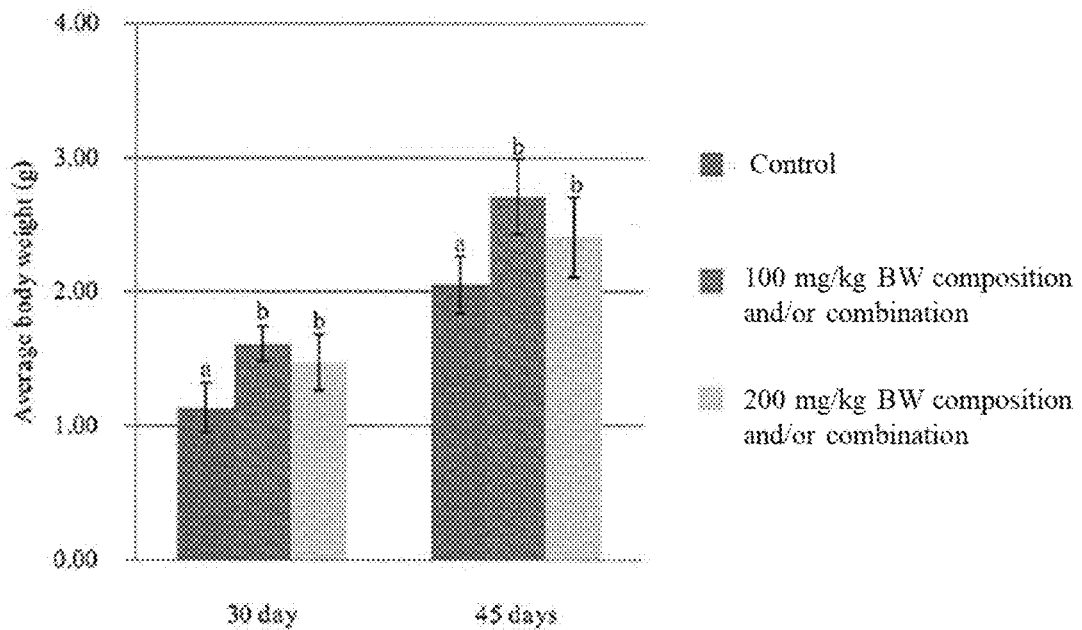
FIG. 60 is a graph of average body weight versus time, illustrating the average body weight of shrimp that are fed one embodiment of the disclosed composition and/or combination at different inclusion rates on days 30 and 45 of the trial.

The average body weight of shrimp in all groups were showed in Table 3 and FIG. 60. Shrimp in the control group had a lower average body weight of 1.14±0.2 g (at 30 day) and 2.05±0.2 g (at 45 day) compared with the two treatment groups (P<0.05) throughout the feeding trial. Shrimp fed with 100 mg/kg BW of the composition and/or combination had the highest average body weight of 1.62±0.1 g (at 30 day) and 2.71±0.3 g (at 45 day). While the average body weight of shrimp fed with 200 mg/kg BW of the composition and/or combination were 1.48±0.2. (at 30 day) and 2.41±0.3 g. (at 45 day).

TABLE 3

Average body weight of Pacific white shrimp at days 30 and 45

| | Average body weight (g) | |
|---|---|---|
| Treatment | 30 days | 45 days |
| Control | $1.14 \pm 0.2^a$ | $2.05 \pm 0.2^a$ |
| 100 mg/kg BW Composition and/or combination | $1.62 \pm 0.1^b$ | $2.71 \pm 0.3^b$ |
| 200 mg/kg BW Composition and/or combination | $1.48 \pm 0.2^b$ | $2.41 \pm 0.3^b$ |

Data are presented as mean ± standard deviation. Means in the same column with different superscript are significantly different from each other ($p < 0.05$)

Figure 61:
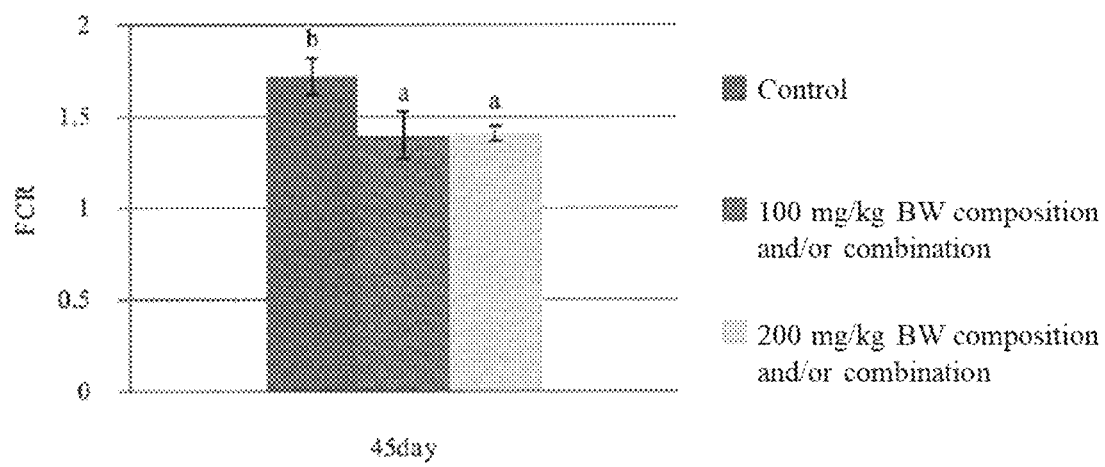
FIG. 61 is a graph of feed conversion ratio (FCR) at day 45, illustrating the feed conversion rate at day 45 of shrimp that are fed one embodiment of the disclosed composition and/or combination at different inclusion rates compared to control shrimp.

The average feed conversion ratio (FCR) is shown in Table 4 and FIG. 61. Shrimp fed with 100 mg/kg BW and 200 mg/kg BW of the composition and/or combination had a lower feed conversion ratios (FCR) of 1.40±0.1 and 1.41±0.04, respectively compared with the control group (1.72±0.10) (p<0.05).

TABLE 4

Feed conversion ratios of Pacific white shrimp after 45 day of feeding with different diets

| Treatment | FCR |
|---|---|
| Control | $1.72 \pm 0.1^b$ |
| 100 mg/kg BW Composition and/or combination | $1.4 \pm 0.1^a$ |
| 200 mg/kg BW Composition and/or combination | $1.41 \pm 0.04^a$ |

Data are presented as mean ± standard deviation. Means in the same column with different superscript are significantly different from each other ($p < 0.05$)

The water qualities of the groups were not significantly different from each other. The water qualities in each tank were controlled within the suitable range for shrimp cultured throughout the feeding trial (Table 5).

TABLE 5

Average water qualities of each treatment group throughout the trial

| | Treatment | | |
|---|---|---|---|
| Parameter | Control | 100 mg/kg BW | 200 mg/kg BW |
| Temperature (° C.) | $28.83 \pm 1.1^a$ | $29.41 \pm 0.1^a$ | $28.62 \pm 1.2^a$ |
| Dissolved oxygen (ppm) | $6.35 \pm 0.3^a$ | $6.3 \pm 0.2^a$ | $6.18 \pm 0.3^a$ |
| pH | $8.16 \pm 0.2^a$ | $8.03 \pm 0.1^a$ | $8.14 \pm 0.4^a$ |
| Total alkalinity (ppm of $CaCO_3$) | $150.0 \pm 11^a$ | $146.67 \pm 16.5^a$ | $150.0 \pm 11^a$ |
| Total ammonia-nitrogen (ppm) | $2.71 \pm 0.9^a$ | $1.50 \pm 0.7^a$ | $1.59 \pm 0.5^a$ |
| Nitrate-nitrogen (ppm) | $0.68 \pm 0.6^a$ | $0.25 \pm 0.2^a$ | $0.84 \pm 0.5^a$ |

Data are presented as mean ± standard deviation. Means in the same row with different superscript are significantly different from each other ($p < 0.05$)

Example 11

The Effect of the Composition and/or Combination on Growth and Survival of White Shrimp (*Litopenaeus vannamei*) Juvenile Challenged with Pathogenic Bacteria (*Vibrio parahaemolyticus*)

Objective

To determine the effect of the composition and/or combination on growth and survival of white shrimp (*Litopenaeus vannamei*) juvenile challenged with pathogenic bacteria (*Vibrio harveyi*) in laboratory conditions. In this trial, the composition and/or combination was administered as a composition comprising between 15% and 40% silica, between 50% and 81% mineral clay, between 1.0% and 5.0% β-glucans, between 0.05% and 3.0% β-1,3 (4)-endo-glucanohydrolase and between 1% and 8.0% mannans.

Early Mortality Syndrome (EMS) cause by *V. parahaemolyticus* is a common occurrence during the growout period between 40-60 days post-stocking. This trial was carried out to determine the composition and/or combination's effect on growth and survival of shrimp challenged with pathogenic bacteria (*V. parahaemolyticus*).

Experimental Animals

Juvenile white shrimp weighing 2 g (45 days) from the trial 1 were used in this study. A total of 30 healthy shrimp were sampled and acclimated in fiberglass tanks for 7 days before the trial. A total of 12 500-liter tanks were used in the trial. Salinity during the acclimation period and subsequent trial was maintained 20-25 ppt., and temperature was maintained constantly at 29±1° C. A virulent strain of *V. parahaemolyticus* that had been cultured in Tryptic Soy Agar (TSA) with 1.5% NaCl (w/v) was added into the tanks at the dose of 104 CFU/mL before stocking. This number of bacteria *Vibrio* is commonly found in pond-reared white shrimp during the culture period.

Two experimental groups with six replicates each were used as in the trial 1. Five tanks from each group were used for growth and survival study. Another one tank from each group was used for histological study.

Growth and Survival Study

Shrimp were fed four times daily at the satiation rate. Feeding rate was adjusted according to shrimp weight throughout the 30 days experimental period. Water quality parameters such as pH, dissolved oxygen (DO), alkalinity, ammonia and nitrite were maintained at optimal levels for rearing shrimp and analyzed weekly throughout the experiment. Survival rate was recorded every 10 days. Shrimp were weighed at days 15 and 30. Mortality and other behavioral responses were recorded throughout the 30 days experimental period.

Immune Parameters Study

The immune parameters, comprising phenoloxidase, bacterial activity, phagocytosis activity and total hemocytes, were measured at the end of the feeding trial. At least 10 shrimp per treatment were used for the immunological tests. Blood samples of 0.5 mL per sample were withdrawn from the base of the third walking leg of the shrimp by a syringe containing 1.5 mL anticoagulant (K-199+5% L-cysteine).

1. Total Hemocytes

After collected hemolymph, hemocytes were counted using a hemocytometer and calculated for number blood cells (total hemocytes per cubic millimeter).

2. Phenoloxidase Activity Assay

After the blood was withdrawn, the hemocytes were washed three times with shrimp saline (1,000 rpm at 4° C. for 10 minutes). Hemocyte lysate (HLS) was prepared from hemocytes in a cacodylate buffer at pH 7.4 using a sonicator at 30 amplitude for 5 seconds followed by centrifuging the suspension at 10,000 rpm at 4° C. for 20 minutes.

The supernatant was collected as HLS. Then 200 µl of 0.1% trypsin in cacodylate buffer was mixed with the 200 mL HLS followed by 200 µl of L-dihydroxyphenylalanine (L-DOPA) at 4 mg/mL as a substrate. Enzyme activity was measured as the absorbance of dopachrome at a wavelength of 490 nm, and the protein content in HLS was measured. The phenoloxidase activity was calculated as the increasing of optimum density (OD) per minute per mg of protein as:

1 unit of phenoloxidase $\Delta OD490/min/mg$ protein.

3. Bactericidal Activity

Serum was separated from blood of each shrimp sample and diluted by 2.6% NaCl at 1:2, 1:4; 1:8, 1:16 and 1:32. 0.5 mL of each serum dilution and 0.5 mL of NaCl as the control were used in the study. 0.5 mL *V. parahaemolyticus* suspension (prepared from the method as in 2) was put into each serum dilution and the control. The treatments were incubated at room temperature for 3 hours before enumerating the number of bacteria by a spread plate technique, and $EC_{50}$ values were recorded.

4. Phagocytosis

Two hundred microliters of hemolymph was collected from the base of the third walking leg of the shrimp and mixed with 800 µL of sterile anticoagulant. Collected shrimp hemocytes were rinsed with shrimp saline and the viable cell number adjusted to $1 \times 10^6$ cells/mL. The cell suspension (200 was inoculated into a cover slip. After 20 minutes. the cell suspension was removed, and rinsed with shrimp saline three times. Heat-killed yeast was added and incubation for 2 hours. After the incubation, the heat-killed yeast was removed, rinsed with shrimp saline five times, and fixed with 100% methanol. Then, this cover slip was stained with Giemsa stain and mounted with permount.

Two hundred hemocytes were counted. Phagocytic activity, defined as percentage phagocytosis, was expressed as $$\text{Percentage phagocytosis} = \frac{\text{phagocytic hemocytes}}{\text{total hemocytes}} \times 100$$

Intestinal Bacterial Study and Histological Study

One tank from each group was used for intestinal bacterial and histological studies. Five shrimp were sampled from each group at 10, 20 and 30 days of the trial. The intestine of each shrimp was removed, homogenized and spread on thiosulfate citrate bile salts sucrose agar (TCBS; selective media for *Vibrio* spp. culture)) or nutrient agar (NA; general media for most bacteria culture) by the spreading method, then incubated at 37° C. for 24 hours. Then all colonies of bacteria were counted. and the CFU/g was calculated.

The head of each shrimp was fixed with Davidson's fixative and processed for histological study to observe the quality of the hepatopancreas and the sign of bacterial infection.

Results

Figure 62:
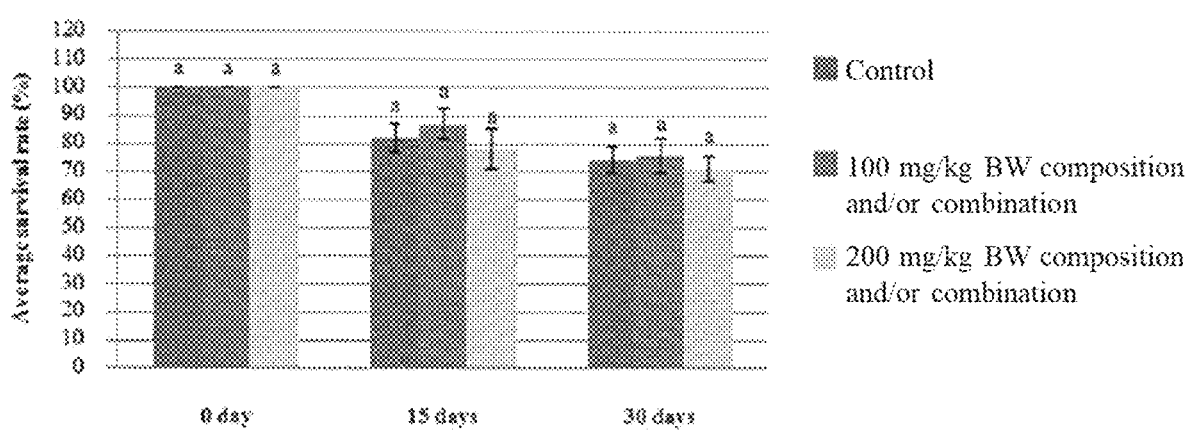
FIG. 62 is a graph of average survival rate versus time, illustrating the average survival of shrimp that are fed one embodiment of the disclosed composition and/or combination at different inclusion rates at days 0, 15 and 30.

The average survival rate of Pacific white shrimp in all groups after challenged with *Vibrio parahaemolyticus* causing Early Mortality Syndrome are shown in Table 6 and FIG. 62.

TABLE 6

Average survival rates of Pacific white shrimp at 0, 15 and 30 days

| Treatment | Average survival rate (%) | | |
|---|---|---|---|
| | Day 0 | Day 15 | Day 30 |
| Control | $100^a$ | $81.88 \pm 5.2^a$ | $74.38 \pm 4.7^a$ |
| 100 mg/kg BW Composition and/or combination | $100^a$ | $86.96 \pm 5.6^a$ | $75.68 \pm 6.1^a$ |
| 200 mg/kg BW Composition and/or combination | $100^a$ | $78.05 \pm 7.0^a$ | $71.33 \pm 4.3^a$ |

Data are presented as mean ± standard deviation. Means in the same column with different superscript are significantly different from each other (p < 0.05)

Figure 63:
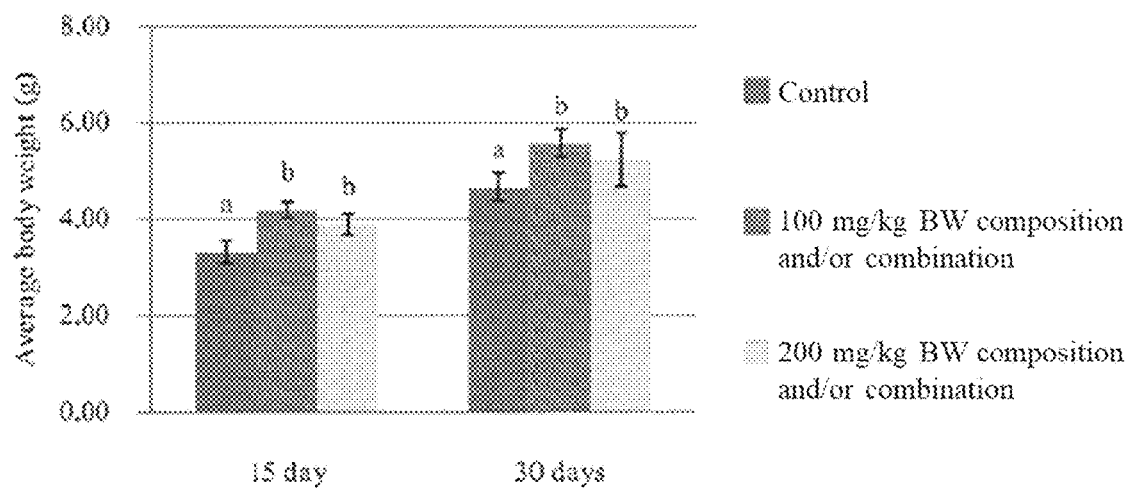
FIG. 63 is a graph of average body weight versus time, illustrating the average body weight of shrimp that are fed one embodiment of the disclosed composition and/or combination at different inclusion rates on days 15 and 30 of the challenge trial.

The average body weight of shrimp in all groups after 30 days are provided in Table 7 and FIG. 63. Shrimp in the control group had a lower average body weight of $3.31 \pm 0.2$ g (at 15 day) and $4.67 \pm 0.3$ g (at 30 day) compared with the two treatment groups (P<0.05) throughout the trial.

TABLE 7

Average body weight of Pacific white shrimp at days 15 and 30

| Treatment | Average body weight (g) | |
|---|---|---|
| | 15 days | 30 days |
| Control | $3.31 \pm 0.2^a$ | $4.67 \pm 0.3^a$ |
| 100 mg/kg BW Composition and/or combination | $4.19 \pm 0.2^b$ | $5.57 \pm 0.3^b$ |
| 200 mg/kg BW Composition and/or combination | $3.89 \pm 0.2^b$ | $5.24 \pm 0.6^b$ |

Data are presented as mean ± standard deviation. Means in the same column with different superscript are significantly different from each other (p < 0.05)

Figure 64:
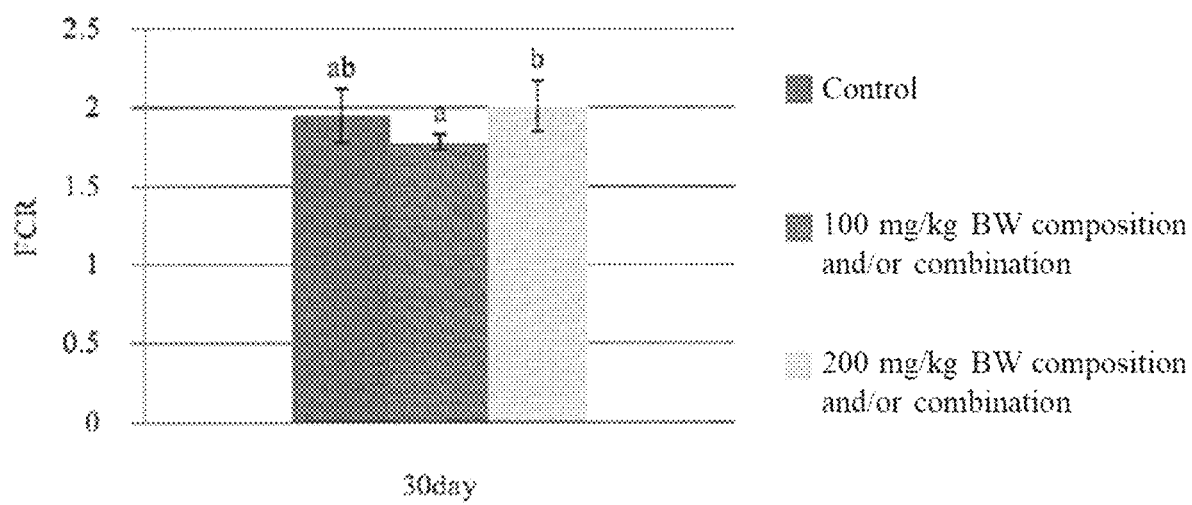
FIG. 64 is a graph of feed conversion ratio (FCR) at day 30, illustrating the feed conversion rate at day 30 of shrimp that are fed one embodiment of the disclosed composition and/or combination at different inclusion rates compared to control shrimp in a challenge trial.

The average feed conversion ratio (FCR) of shrimp in all groups after 30 days of the challenge trail are provided in Table 8 and FIG. 64.

TABLE 8

FCR of Pacific white shrimp after 30
day of feeding with different diets

| Treatment | FCR |
| --- | --- |
| Control | $1.95 \pm 0.2^{ab}$ |
| 100 mg/kg BW Composition and/or combination | $1.78 \pm 0.05^{a}$ |
| 200 mg/kg BW Composition and/or combination | $2.01 \pm 0.2^{b}$ |

Data are presented as mean ± standard deviation. Means in the same column with different superscript are significantly different from each other ($p < 0.05$)

The water qualities in each tank were controlled within the suitable range for shrimp cultured throughout the challenged trial (Table 9).

TABLE 9

Average water qualities of each treatment
group throughout the trial

| | Treatment | | |
| --- | --- | --- | --- |
| Parameter | Control | 100 mg/kg BW | 200 mg/kg BW |
| Temperature (° C.) | $28.72 \pm 0.6^{a}$ | $28.71 \pm 0.6^{a}$ | $28.79 \pm 0.6^{a}$ |
| Dissolved oxygen (ppm) | $6.35 \pm 0.3^{a}$ | $6.3 \pm 0.2^{a}$ | $6.1 \pm 0.3^{a}$ |
| pH | $8.15 \pm 0.2^{a}$ | $8.03 \pm 0.1^{a}$ | $8.03 \pm 0.1^{a}$ |
| Total alkalinity (ppm of $CaCO_3$) | $150.0 \pm 21.8^{a}$ | $153.33 \pm 19.6^{a}$ | $150.0 \pm 11^{a}$ |
| Total ammonia-nitrogen (ppm) | $1.34 \pm 0.6^{a}$ | $0.56 \pm 0.2^{a}$ | $1.02 \pm 0.9^{a}$ |
| Nitrate-nitrogen (ppm) | $0.09 \pm 0.05^{a}$ | $0.07 \pm 0.03^{a}$ | $0.1 \pm 0.03^{a}$ |

Data are presented as mean ± standard deviation. Means in the same row with different superscript are significantly different from each other ($p < 0.05$)

Figure 65:
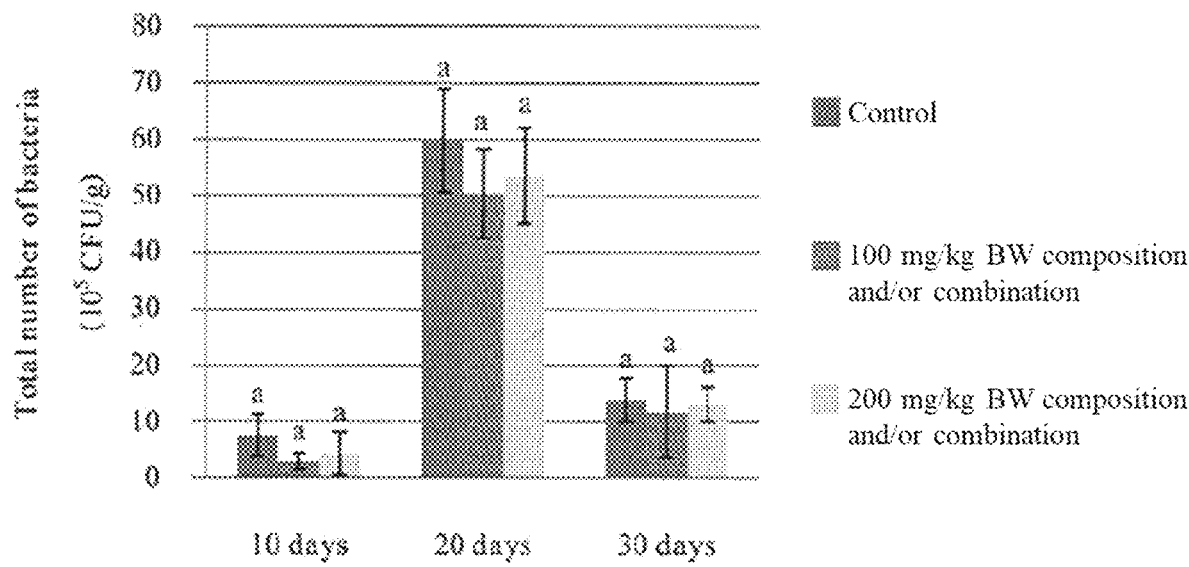
FIG. 65 is a graph of number of bacteria versus time, illustrating the total number of bacteria in the intestine of shrimp that are fed different diets.
Figure 66:
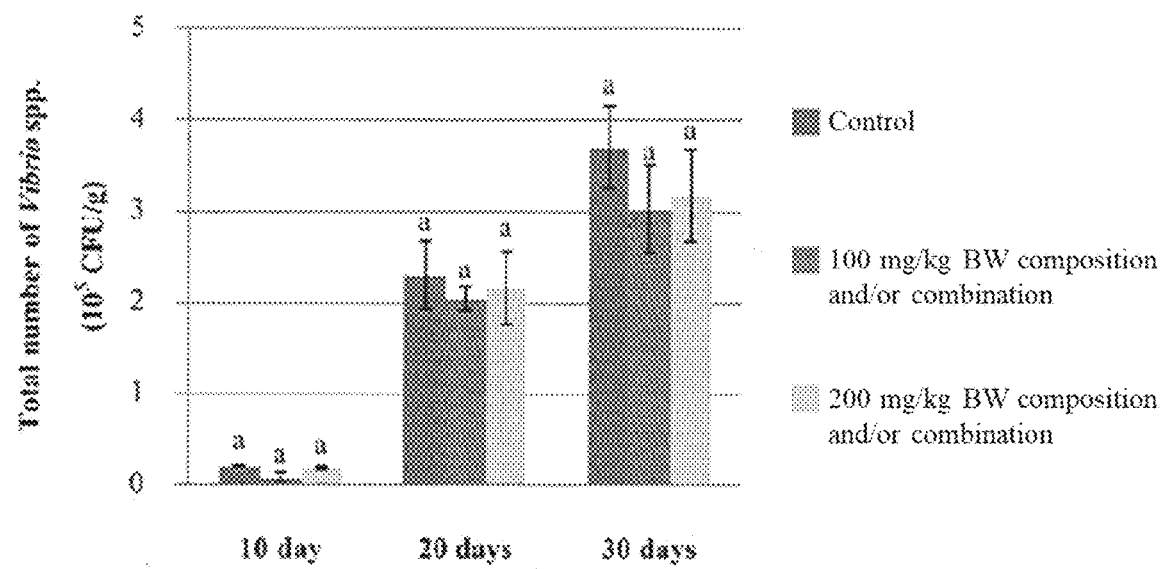
FIG. 66 is a graph of number of *Vibrio* species versus time, illustrating the total number of *Vibrio* species in the shrimp that are fed different diets.
Figure 67:
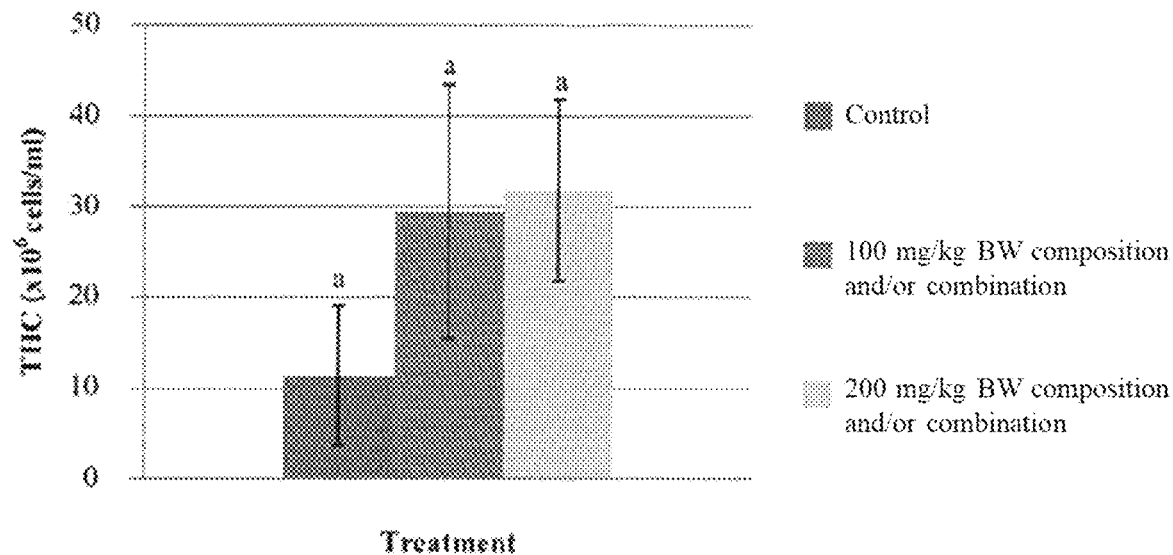
FIG. 67 is a graph of total hemocyte count versus treatment, illustrating the hemocyte count in shrimp administered different amounts of the composition and/or combination.
Figure 68:
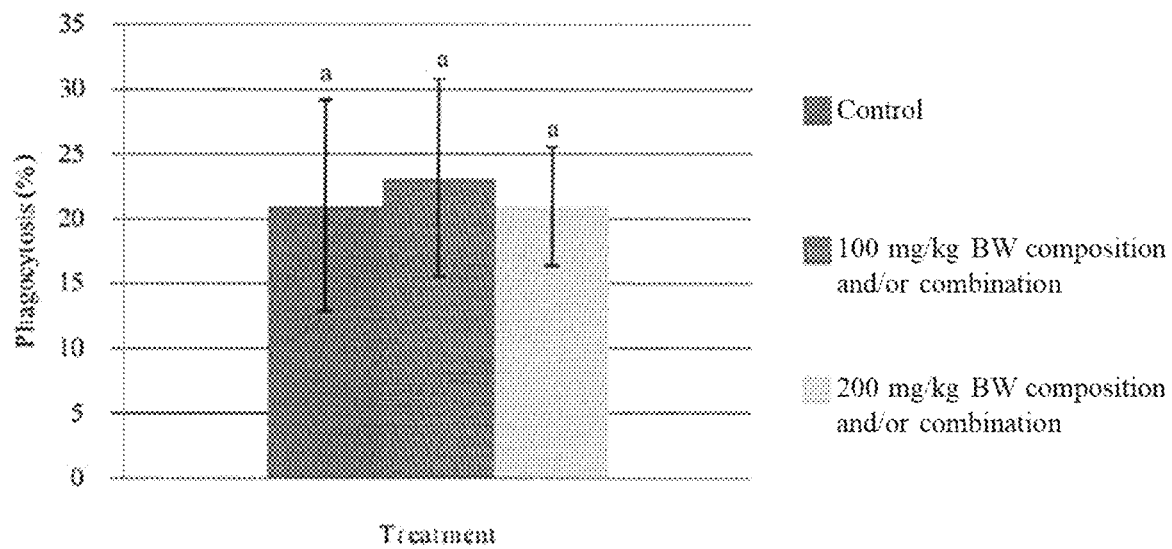
FIG. 68 is a graph of phagocytosis activity versus treatment, illustrating the phagocytosis activity count in shrimp administered different amounts of the composition and/or combination.
Figure 69:
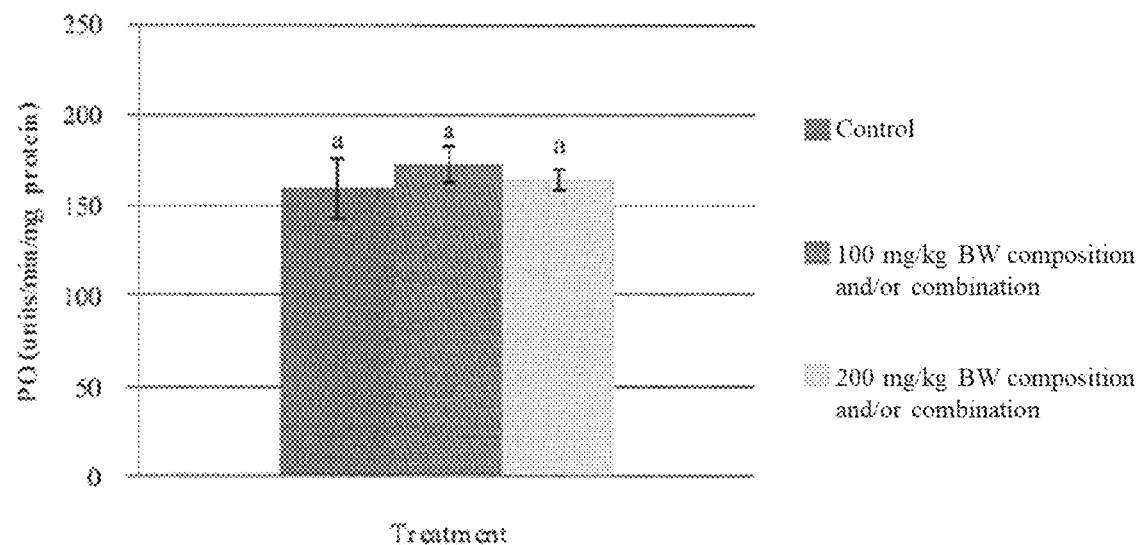
FIG. 69 is a graph of phenoloxidase activity versus treatment, illustrating the phenoloxidase activity in shrimp administered different amounts of the composition and/or combination.
Figure 70:
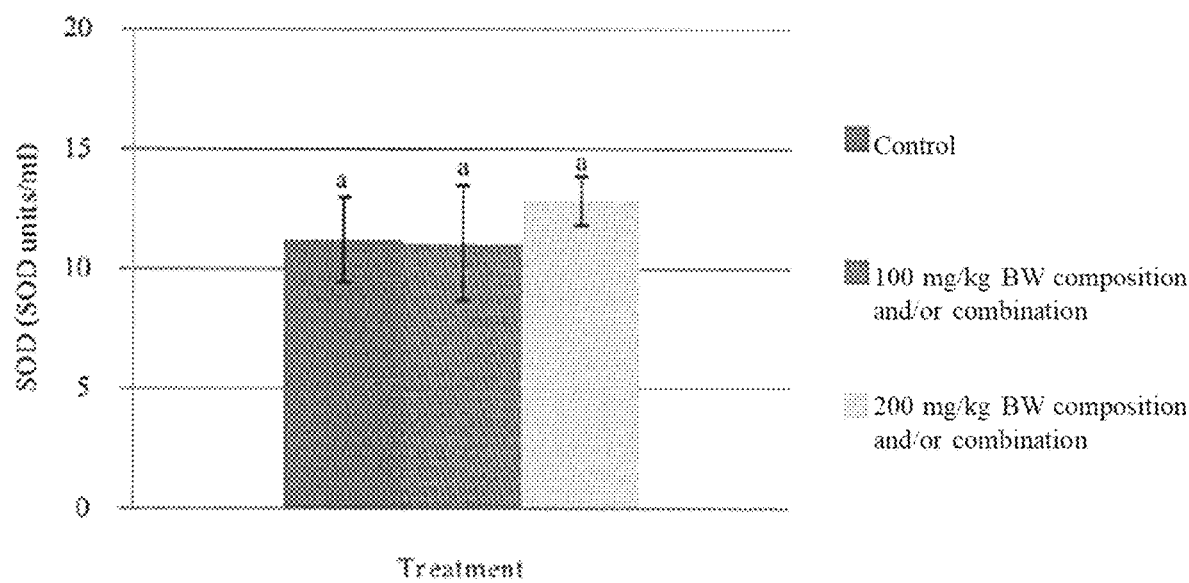
FIG. 70 is a graph of superoxide dismutase activity versus treatment, illustrating the superoxide dismutase activity in shrimp administered different amounts of the composition and/or combination.
Figure 71:
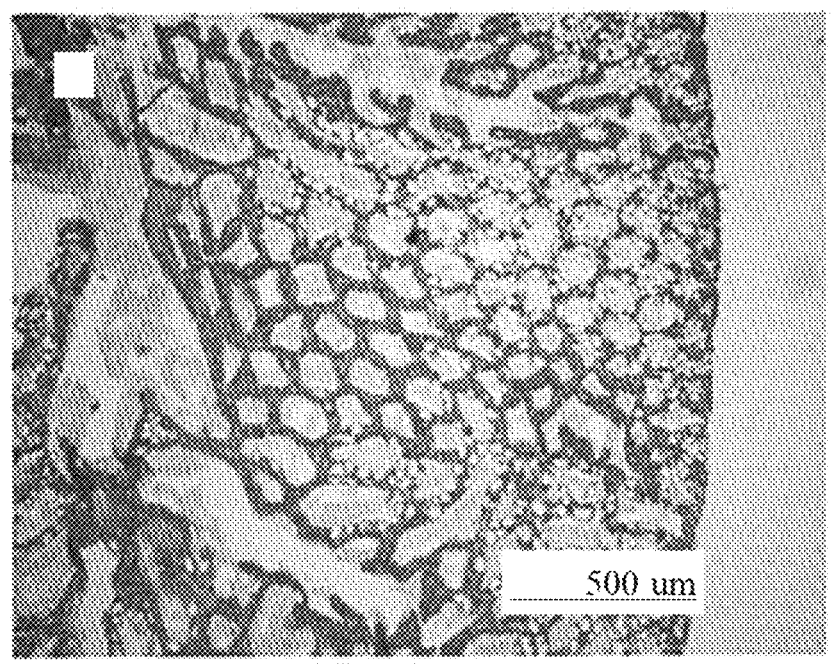
FIG. 71 is a digital image of a portion of the hepatopancreas of control shrimps, illustrating about 30% cell necrosis.
Figure 72:
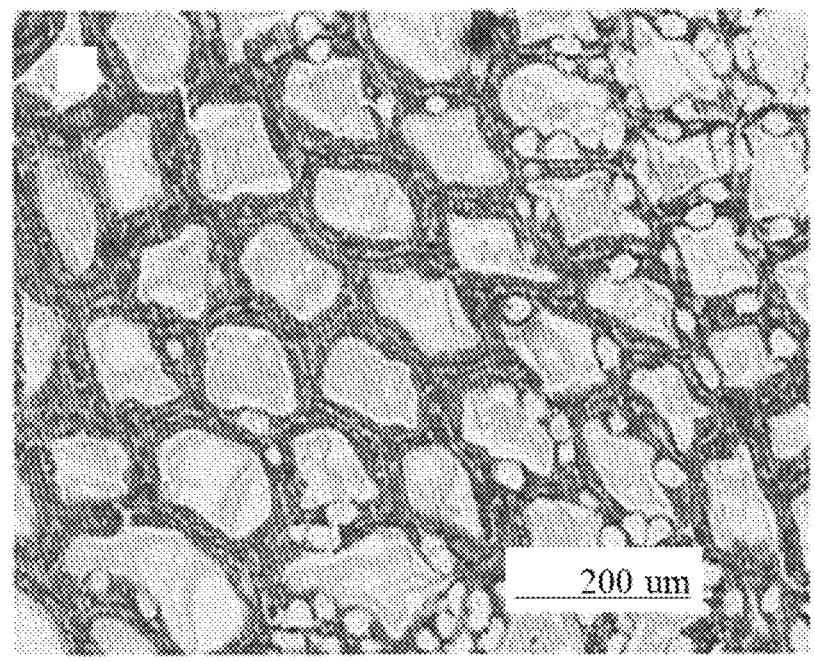
FIG. 72 is a digital image providing an expanded view of the hepatopancreas shown in FIG. 71.
Figure 73:
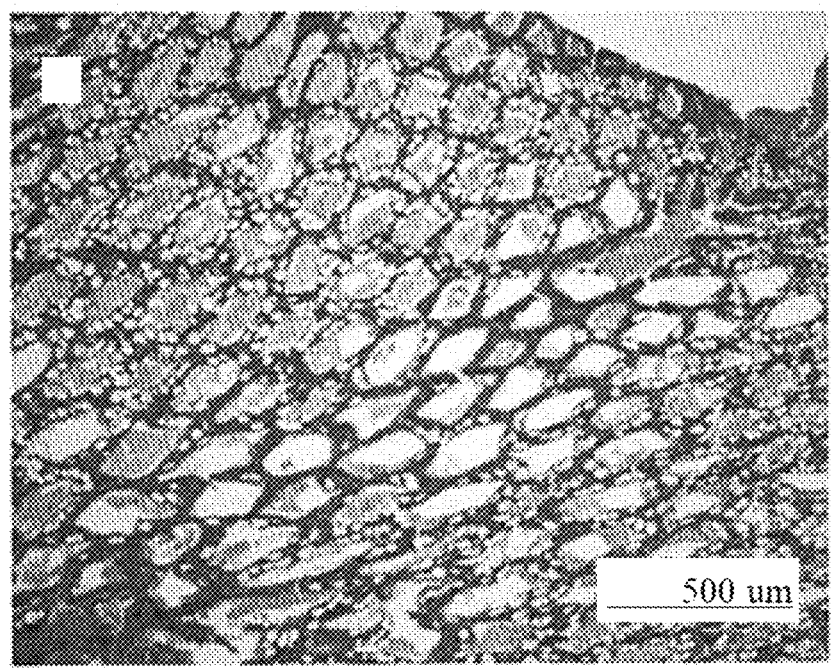
FIG. 73 is a digital image of a portion of the hepatopancreas of shrimps administered 100 mg/kg BW of one embodiment of the disclosed composition and/or combination, illustrating about 25% cell necrosis.
Figure 74:
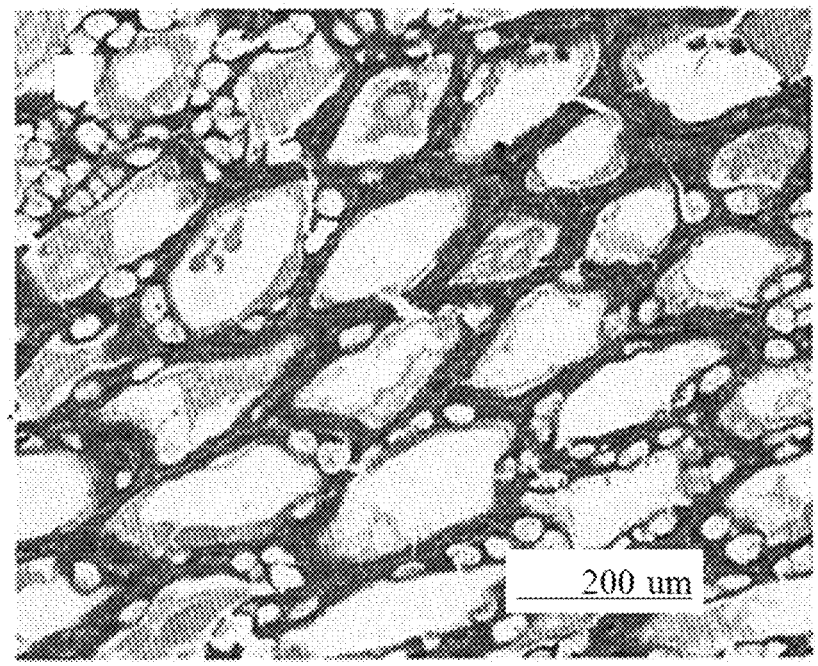
FIG. 74 is a digital image providing an expanded view of the hepatopancreas shown in FIG. 73.
Figure 75:
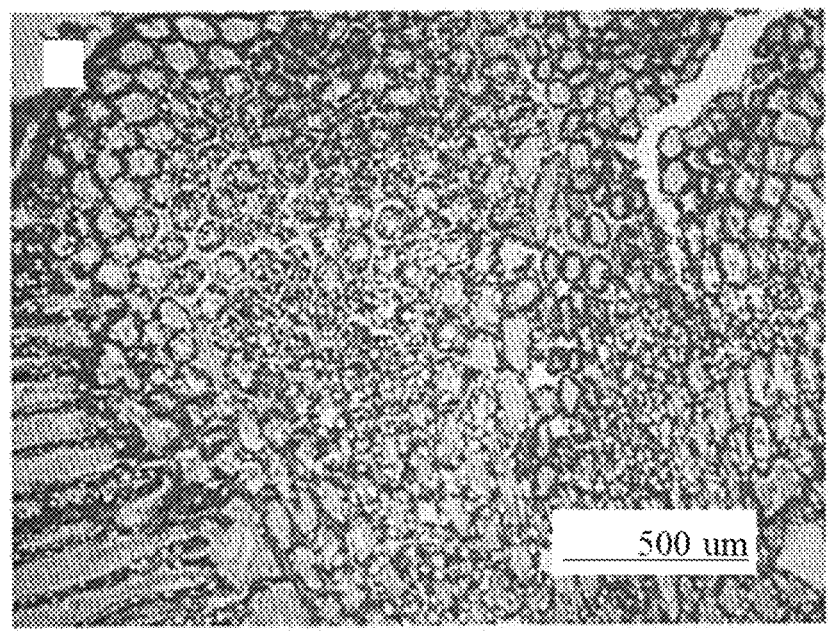
FIG. 75 is a digital image of a portion of the hepatopancreas of shrimps administered 200 mg/kg BW of one embodiment of the disclosed composition and/or combination, illustrating about 25% cell necrosis.
Figure 76:
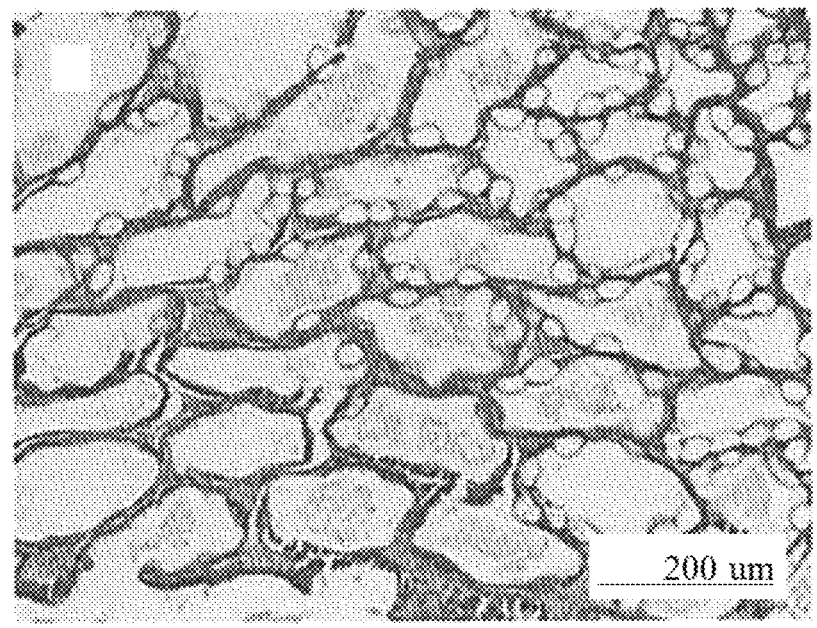
FIG. 76 is a digital image providing an expanded view of the hepatopancreas shown in FIG. 75.

The average total number of bacteria in the intestine of shrimp are shown in Table it) and FIG. 65. And the average total number of *Vibrio parahaemolyticus* in the intestine of shrimp is shown in Table 11 and Flea. 66. And immunological results are provided by Tables 12-16 and FIGS. 67-70.

TABLE 10

Average number of bacteria ($10^5$ CFU/g) in the intestine
of Pacific white shrimp after a challenge with *V. parahaemolyticus*
($10^4$ CFU/g) for 30 days

| | Total number of bacteria ($10^5$ CFU/g) in the intestine | | |
| --- | --- | --- | --- |
| Treatment | 10 days | 20 days | 30 days |
| Control | $7.69 \pm 3.8^{a}$ | $59.83 \pm 9.2^{a}$ | $13.88 \pm 4^{a}$ |
| 100 mg/kg BW Composition and/or combination | $3.01 \pm 1.4^{a}$ | $50.32 \pm 7.9^{a}$ | $11.80 \pm 8.2^{a}$ |
| 200 mg/kg BW Composition and/or combination | $4.38 \pm 3.9^{a}$ | $53.54 \pm 8.6^{a}$ | $13.06 \pm 3.1^{a}$ |

Data are presented as mean ± standard deviation. Means in the same column with different superscript are significantly different from each other ($p < 0.05$)

TABLE 11

Average number of *Vibrio* spp. ($10^5$ CFU/g) in the
intestine of Pacific white shrimp after a challenge with
*V. parahaemolyticus* ($10^4$ CFU/g) for 30 days

| | Total number of *Vibrio* spp. ($10^5$ CFU/g) in the intestine | | |
| --- | --- | --- | --- |
| Treatment | 10 days | 20 days | 30 days |
| Control | $0.20 \pm 0.01^{a}$ | $2.29 \pm 0.4^{a}$ | $3.70 \pm 5^{a}$ |
| 100 mg/kg BW Composition and/or combination | $0.08 \pm 0.06^{a}$ | $2.04 \pm 0.1^{a}$ | $3.03 \pm 0.5^{a}$ |
| 200 mg/kg BW Composition and/or combination | $0.18 \pm 0.02^{a}$ | $2.16 \pm 0.4^{a}$ | $3.17 \pm 0.5^{a}$ |

Data are presented as mean ± standard deviation. Means in the same column with different superscript are significantly different from each other ($p < 0.05$)

TABLE 12

Total hemocyte count ($10^7$ cells/mL) of Pacific white shrimp after
challenge with *V. parahaemolyticus* ($10^4$ CFU/g) for 30 days

| Treatment | THC ($10^6$ cells/mL) |
| --- | --- |
| Control | $11.3 \pm 7.7^{a}$ |
| 100 mg/kg BW Composition and/or combination | $29.5 \pm 14^{a}$ |
| 200 mg/kg BW Composition and/or combination | $31.8 \pm 10^{a}$ |

Data are presented as mean ± standard deviation. Means in the same column with different superscript are significantly different from each other ($p < 0.05$)

TABLE 13

The phagocytosis activity (%) of Pacific white shrimp after
challenge with *V. parahaemolyticus* ($10^4$ CFU/g) for 30 days

| Treatment | Phagocytosis (%) |
| --- | --- |
| Control | $21.00 \pm 8.2^{a}$ |
| 100 mg/kg BW Composition and/or combination | $23.17 \pm 7.7^{a}$ |
| 200 mg/kg BW Composition and/or combination | $21.00 \pm 4.6^{a}$ |

Data are presented as mean ± standard deviation. Means in the same column with different superscript are significantly different from each other ($p < 0.05$)

TABLE 14

The phenoloxidase activity (units/min/mg protein)
of Pacific white shrimp after challenge with *V. parahaemolyticus*
($10^4$ CFU/g) for 30 days

| Treatment | Phenoloxidase (units/min/mg protein) |
| --- | --- |
| Control | $159.33 \pm 16.5^{a}$ |
| 100 mg/kg BW Composition and/or combination | $172.11 \pm 10^{a}$ |
| 200 mg/kg BW Composition and/or combination | $164.04 \pm 5.8^{a}$ |

Data are presented as mean ± standard deviation. Means in the same column with different superscript are significantly different from each other ($p < 0.05$)

TABLE 15

The superoxide dismutase activity (SOD units/mL)
of Pacific white shrimp after challenge with *V. parahaemolyticus*
($10^4$ CFU/g) for 30 days

| Treatment | SOD (SOD units/mL) |
|---|---|
| Control | 11.22 ± 1.8[a] |
| 100 mg/kg BW Composition and/or combination | 11.05 ± 2.4[a] |
| 200 mg/kg BW Composition and/or combination | 12.84 ± 1[a] |

Data are presented as mean ± standard deviation. Means in the same column with different superscript are significantly different from each other ($p < 0.05$)

TABLE 16

The bactericidal activity of Pacific white shrimp after challenge
with *V. parahaemolyticus* ($10^4$ CFU/g) for 30 days

| Treatment | Bactericidal activity |
|---|---|
| Control | 1:8 |
| 100 mg/kg BW Composition and/or combination | 1:8 |
| 200 mg/kg BW Composition and/or combination | 1:8 |

Histopathological study of the hepatopancreas of the studies shrimp revealed signs of cell necrosis in the hepatopancreas, caused by toxin from *Vibrio parahaemolyticus* infections. The percentage of necrosis cell in the hepatopancreas of the shrimp from each group was similar at about 25-30% (FIGS. 71-76).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A particulate composition formulated for administration to a fish, crustacean, or mollusk, comprising a particulate feedstuff for a fish, crustacean, or mollusk, an adhesive agent, and a first composition comprising:
    glucan, silica, mineral clay, mannans and endoglucanohydrolase; or
    glucan, silica, mineral clay, mannans, endoglucanohydrolase, *yucca* and *quillaja*; wherein
    each particle of the particulate composition comprises a core comprising a feedstuff particle wherein the feedstuff is a feedstuff for fish, crustaceans, or mollusks, the adhesive agent forms a first layer that at least partially covers the feedstuff particle, and the first composition forms a second layer that at least partially covers the first layer;
    each particle of the particulate composition is formulated for administration to the fish, crustacean, or mollusk, such that each dimension of the particle is no more than 3 mm, and therefore the particle has a particle size of from greater than 0 mm to 3 mm; and
    the first composition is present in the particulate composition at an amount of from 500 mg to 7,500 mg per kg of feedstuff.

2. The particulate composition of claim 1, wherein the first composition comprises glucan, silica, mineral clay, mannans, and endoglucanohydrolase, and the first composition is adhered to the feedstuff for a fish, crustacean, or mollusk by a first adhesive agent to produce a first solid material having a first particle size of from greater than 0 mm to 3 mm.

3. The particulate composition of claim 1, wherein the particulate composition comprises from greater than zero to at least 10% adhesive agent by weight.

4. The particulate composition of claim 1, wherein the adhesive agent is an oil or a syrup.

5. The particulate composition of claim 4, wherein the adhesive agent is selected from soy oil, linseed oil, tung oil, dehydrated castor oil, canola oil, olive oil, palm oil, cottonseed oil, Naskole oil, molasses, sugar syrup, sorghum, honey or a combination thereof.

6. The particulate composition of claim 4, wherein the adhesive agent comprises at least 2 wt % soy oil.

7. The particulate composition of claim 2, wherein the first composition comprises between 15% and 40% silica, between 50% and 81% mineral clay, between 1.0% and 5.0% β-glucans, and between 1% and 8.0% mannans.

8. The particulate composition of claim 2, wherein the particulate composition further comprises *yucca, quillaja*, or *yucca* and *quillaja*.

9. The particulate composition of claim 1, wherein the particulate composition further comprises at least one *Bacillus* species.

10. The particulate composition of claim 2, wherein the first composition consists essentially of between 15% and 40% silica, between 50% and 81% mineral clay, between 1.0% and 5.0% β-glucans, between 0.05% and 3.0% β-1,3(4)-endoglucanohydrolase, between 1% and 8.0% mannans, and/or at least 2% of the first adhesive agent.

11. The particulate composition of claim 1, wherein the feedstuff is a feed ration, a mineral supplement, a protein supplement, a premix, or any combination thereof.

12. The particulate composition of claim 1, wherein each particle in the particulate composition comprises the feedstuff, at least 2% soy oil, and from 15% to 40% silica, from 50% to 81% mineral clay, from 1.0% to 5.0% β-glucans, from 0.05% to 3.0% β-1,3(4)-endoglucanohydrolase, and from 1% to 8.0% mannans in amounts relative to each other.

13. The particulate composition of claim 1, wherein the feedstuff is a feedstuff for hatchery fish, crustaceans or mollusks, and the particle size is from greater than 0 mm to 2 mm.

14. The particulate composition of claim 1, wherein the feedstuff is a feedstuff for nursery fish, crustaceans or mollusks, and the particle size is from greater than 2 mm to 3 mm.

15. The particulate composition of claim 1, wherein the adhesive agent and the first composition each form a complete layer around the feedstuff.

16. The particulate composition of claim 1, formulated for administration to a hatchery fish, crustacean, or mollusk, comprising:
    a hatchery feedstuff for a hatchery fish, crustacean, or mollusk;
    from 2% to 10% of an adhesive agent at least partially coating the hatchery feedstuff; and
    from 500 mg to 1,000 mg per kg of the hatchery feedstuff of the first composition comprising between 15% and 40% silica, between 50% and 81% mineral clay, between 1.0% and 5.0% β-glucans, and between 1% and 8.0% mannans in amounts relative to each other, the first composition contacting the adhesive agent and forming at least a partial layer on the feedstuff;

wherein the particles in the particulate composition have a particle size of from greater than 0 mm to 2 mm.

17. The particulate composition of claim 1, formulated for administration to a nursery fish, crustacean, or mollusk, comprising:
a nursery feedstuff for a nursery fish, crustacean, or mollusk;
from 2% to 10% of an adhesive agent at least partially coating the nursery feedstuff; and
from greater than 1,000 mg to 2,000 mg per kg of the nursery feedstuff of the first composition comprising between 15% and 40% silica, between 50% and 81% mineral clay, between 1.0% and 5.0% β-glucans, and between 1% and 8.0% mannans in amounts relative to each other, the first composition contacting the adhesive agent and forming at least a partial layer on the feedstuff;
wherein the particles in the particulate composition have a particle size of from greater than 2 mm to 3 mm.

18. A method, comprising administering the particulate composition of claim 1 to an aquatic animal selected from a fish, crustacean, or mollusk.

19. The method of claim 18, wherein the particulate composition is administered to the animal to promote growth, to reduce its feed conversion ratio, or both.

20. The method of claim 18, wherein administering the particulate composition enhances a feed conversion ratio of the aquatic animal by from 0.5% to 20%, compared to a feed conversion ratio of an aquatic animal that is not administered the composition.

21. The method of claim 18, wherein the particulate composition is administered to the animal to prevent, delay or ameliorate at least one deleterious symptom or sign.

22. The method of claim 18, wherein the particulate composition is administered to the animal in an amount from 50 mg/kg of body weight per day to 250 mg/kg of body weight per day.

23. The method of claim 18, wherein:
the fish is selected from salmon, trout, tilapia, sea bream, carp, cod, halibut, snapper, herring, catfish, flounder, hake, smelt, anchovy, lingcod, moi, perch, orange roughy, bass, tuna, mahi mahi, mackerel, eel, barracuda, marlin, Atlantic ocean perch, Nile perch, Arctic char, haddock, hoki, Alaskan Pollock, turbot, freshwater drum, walleye, skate, sturgeon, Dover sole, common sole, wolfish, sablefish, American shad, John Dory, grouper, monkfish, pompano, lake whitefish, tilefish, wahoo, cusk, bowfin, kingklip, opah, mako shark, swordfish, cobia, croaker, or hybrids thereof;
the crustacean is selected from shrimp, crab, lobster, crayfish, krill, copepods, barnacles, or hybrids thereof; or
the mollusk is selected from squid, octopus, clam, oyster, mussel, abalone, conch, rock snail, whelk, cockle, or hybrids thereof.

24. The method of claim 23, wherein:
the fish is selected from Nile tilapia, blue tilapia, Mozambique tilapia, tilapiine cichlids, sheepshead, scup, yellowfin bream, gilt-head bream, Saucereye porgies, red sea bream, common carp, Asian carp, Indian carp, black carp, grass carp, silver carp, bighead carp, pink salmon, chum salmon, sockeye salmon, coho salmon, Atlantic salmon, chinook salmon, masu salmon, rainbow trout, Adriatic trout, Bonneville cutthroat trout, brook trout, steelhead trout, Atlantic northeast cod, Atlantic northwest cod, Pacific cod, Pacific halibut, Atlantic halibut, red snapper, bluefish, Atlantic herring, Pacific herring, channel catfish, walking catfish, shark catfish, Corydoras, basa, banjo catfish, talking catfish, long-whiskered catfish, armoured suckermouth catfish, blue catfish, or hybrids thereof;
the crustacean is selected from Chinese white shrimp, pink shrimp, black tiger shrimp, freshwater shrimp, gulf shrimp, Pacific white shrimp, whiteleg shrimp, giant tiger shrimp, rock shrimp, Akiama paste shrimp, Southern rough shrimp, fleshy prawn, banana prawn, Northern prawn, blue crab, peekytoe crab, spanner crab, Jonah crab, snow crab, king crab, stone crab, Dungeness crab, soft-shell crab, Cromer crab, American lobster, spiny lobster, squat lobster, goose barnacle, picoroco barnacle, or hybrids thereof; or
the mollusk is selected from common squid, Patagonian squid, longfin inshore squid, neon flying squid, Argentine shortfin squid, Humboldt squid, Japanese flying squid, Wellington squid, common octopus, hard clam, soft-shell clam, ocean quahog, surf clam, Asari, Hamaguri, Vongola, Cozza, Tellina, Pacific oyster, rock oyster, European flat oyster, Portuguese oyster, blue mussel, freshwater mussel, green-lipped mussel, Asian green mussel, Mediterranean mussel, Baltic mussel, or hybrids thereof.

* * * * *